(12) United States Patent
Connor

(10) Patent No.: US 9,084,859 B2
(45) Date of Patent: Jul. 21, 2015

(54) ENERGY-HARVESTING RESPIRATORY METHOD AND DEVICE

(75) Inventor: Robert A. Connor, Forest Lake, MN (US)

(73) Assignee: Sleepnea LLC, Forest Lake, MN (US)

( * ) Notice: Subject to any disclaimer, the term of this patent is extended or adjusted under 35 U.S.C. 154(b) by 707 days.

(21) Appl. No.: 13/374,708

(22) Filed: Jan. 9, 2012

(65) Prior Publication Data
US 2012/0234323 A1 Sep. 20, 2012

Related U.S. Application Data

(60) Provisional application No. 61/465,196, filed on Mar. 14, 2011.

(51) Int. Cl.
*A61M 16/06* (2006.01)
*A61M 16/00* (2006.01)

(52) U.S. Cl.
CPC ........... *A61M 16/0066* (2013.01); *A61M 16/06* (2013.01); *A61M 16/0666* (2013.01); *A61M 2205/3375* (2013.01); *A61M 2205/825* (2013.01); *A61M 2205/8206* (2013.01); *A61M 2205/8237* (2013.01)

(58) Field of Classification Search
CPC ............ A61M 16/0066; A61M 16/06; A61M 2205/825; A61M 2205/3375; A61M 205/82062; A61M 16/0666; A61F 5/56; H02N 2/18; H02N 2/185; H02N 2/186; H02N 11/008; F03D 9/002
USPC .................. 128/200.24, 848, 205.24, 205.25, 128/206.21, 206.28, 207.12, 207.18, 128/204.18, 204.21; 606/199; 290/1 R, 54, 290/43
See application file for complete search history.

(56) References Cited

U.S. PATENT DOCUMENTS

| 746,869 | A | | 12/1903 | Moulton |
|---|---|---|---|---|
| 3,268,845 | A | | 8/1966 | Whitmore |
| 3,305,399 | A | | 2/1967 | Davis |
| 3,421,512 | A | | 1/1969 | Frasier |
| 3,456,134 | A | | 7/1969 | Ko |
| 3,563,245 | A | | 2/1971 | McLean et al. |
| 3,693,625 | A | | 9/1972 | Auphan |
| 3,774,243 | A | | 11/1973 | Ng et al. |
| 3,837,337 | A | | 9/1974 | LaViolette |
| 3,861,397 | A | | 1/1975 | Rao et al. |
| 3,906,960 | A | | 9/1975 | Lehr |
| 3,908,987 | A | | 9/1975 | Boehringer |
| 3,941,135 | A | | 3/1976 | von Sturm et al. |
| 3,943,936 | A | | 3/1976 | Rasor et al. |
| 4,091,302 | A | * | 5/1978 | Yamashita ..................... 310/339 |

(Continued)

*Primary Examiner* — Annette Dixon
*Assistant Examiner* — Elliot S Ruddie

(57) ABSTRACT

This invention is a method, device, and system to provide respiratory assistance to people with Obstructive Sleep Apnea (OSA), or other respiratory conditions, comprising harvesting and storing energy from gas outflow during exhalation and using that stored energy to increase gas inflow during inhalation. In an example, this invention may provide Positive End-Expiratory Pressure (PEEP) or Continuous positive Airway Pressure (CPAP). This invention can be embodied in a self-contained energy-harvesting positive airway pressure mask, nasal inserts, or mouth appliance. This invention offers a combination of the following five benefits for Obstructive Sleep Apnea (OSA) treatment: minimally-invasive; energy self-sufficient; freedom of movement; hypercapnia avoidance; and adjustable energy harvesting over multiple respiratory cycles.

3 Claims, 12 Drawing Sheets

(56) References Cited

U.S. PATENT DOCUMENTS

Figure 1:
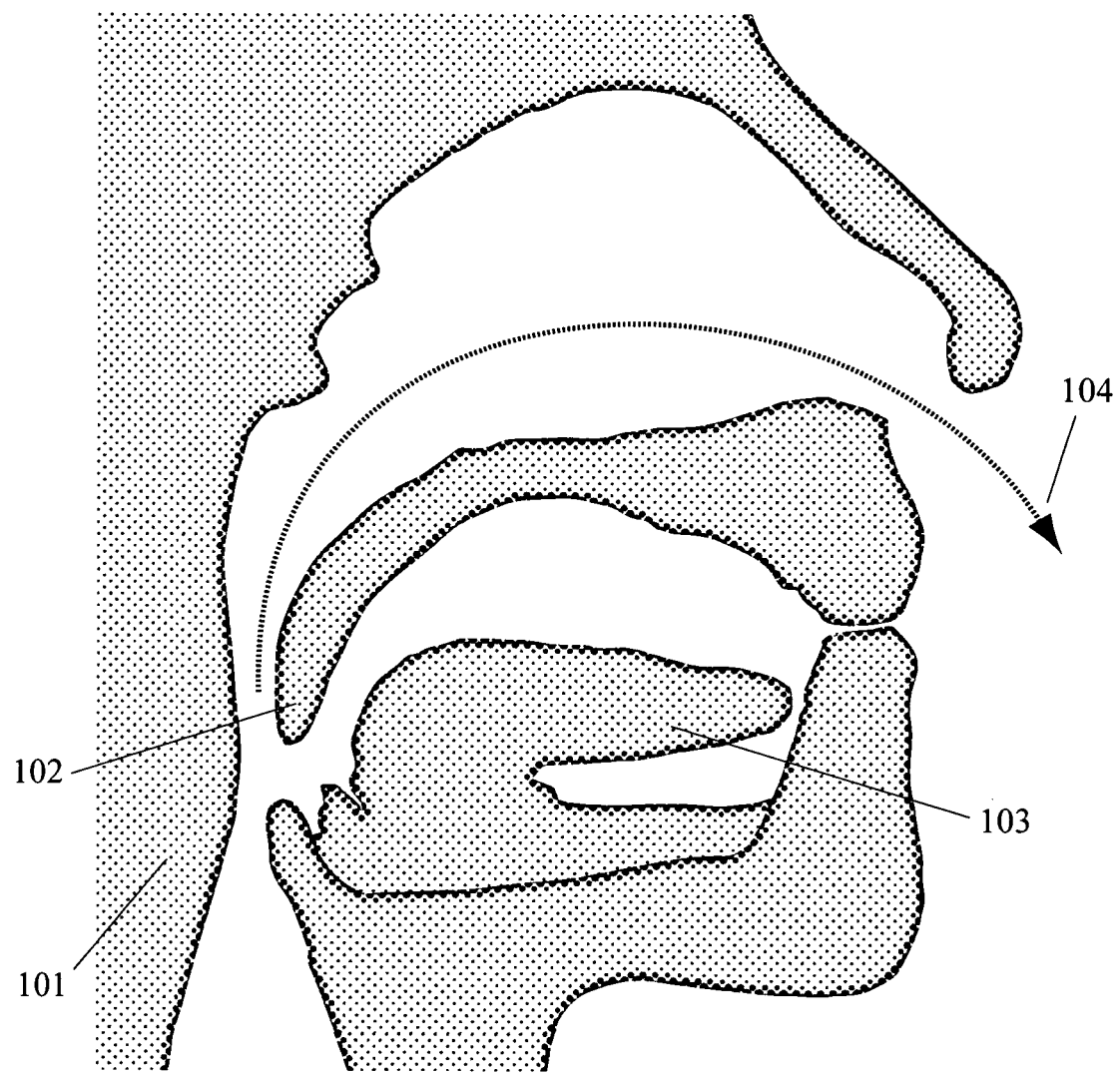

| | | |
|---|---|---|
| 4,140,132 A | 2/1979 | Dahl |
| 4,233,972 A | 11/1980 | Hauff et al. |
| 4,245,640 A | 1/1981 | Hunt |
| 4,453,537 A | 6/1984 | Spitzer |
| 4,506,666 A | 3/1985 | Durkan |
| 4,549,542 A | 10/1985 | Chien |
| 4,690,143 A | 9/1987 | Schroeppel |
| 4,798,206 A | 1/1989 | Maddison et al. |
| 4,821,712 A | 4/1989 | Gossett |
| 4,823,788 A | 4/1989 | Smith et al. |
| 4,886,056 A | 12/1989 | Simpson |
| 4,944,310 A | 7/1990 | Sullivan |
| 5,018,517 A | 5/1991 | Liardet |
| 5,035,239 A | 7/1991 | Edwards |
| 5,048,517 A | 9/1991 | Pasternack |
| 5,123,425 A | 6/1992 | Shannon et al. |
| 5,134,995 A | 8/1992 | Gruenke et al. |
| 5,148,802 A | 9/1992 | Sanders et al. |
| 5,199,424 A | 4/1993 | Sullivan et al. |
| 5,203,343 A | 4/1993 | Axe et al. |
| 5,239,995 A | 8/1993 | Estes et al. |
| 5,245,995 A | 9/1993 | Sullivan et al. |
| 5,259,373 A | 11/1993 | Gruenke et al. |
| 5,301,689 A | 4/1994 | Wennerholm |
| 5,303,701 A | 4/1994 | Heins et al. |
| 5,344,385 A | 9/1994 | Buck et al. |
| 5,372,130 A * | 12/1994 | Stern et al. ............... 128/205.25 |
| 5,431,694 A | 7/1995 | Snaper et al. |
| 5,443,504 A | 8/1995 | Hill |
| 5,479,946 A | 1/1996 | Trumble |
| 5,535,738 A | 7/1996 | Estes et al. |
| 5,540,729 A | 7/1996 | Weijand |
| 5,553,454 A | 9/1996 | Mortner |
| 5,645,054 A | 7/1997 | Cotner et al. |
| 5,649,533 A | 7/1997 | Oren |
| 5,653,676 A | 8/1997 | Buck et al. |
| 5,658,221 A | 8/1997 | Hougen |
| 5,664,562 A | 9/1997 | Bourdon |
| 5,678,567 A | 10/1997 | Thornton et al. |
| 5,687,715 A | 11/1997 | Landis et al. |
| 5,701,919 A | 12/1997 | Buck et al. |
| 5,718,248 A | 2/1998 | Trumble et al. |
| 5,810,015 A | 9/1998 | Flaherty |
| 5,826,579 A | 10/1998 | Remmers et al. |
| 5,845,636 A | 12/1998 | Gruenke et al. |
| 5,868,133 A | 2/1999 | DeVries et al. |
| 5,884,625 A | 3/1999 | Hart |
| 5,888,186 A | 3/1999 | Trumble et al. |
| 5,890,998 A | 4/1999 | Hougen |
| 5,918,597 A | 7/1999 | Jones et al. |
| 5,921,942 A | 7/1999 | Remmers et al. |
| 5,950,624 A | 9/1999 | Hart |
| 5,953,713 A | 9/1999 | Behbehani et al. |
| 5,954,048 A | 9/1999 | Thornton |
| 5,954,058 A | 9/1999 | Flaherty |
| 5,957,133 A | 9/1999 | Hart |
| 5,969,429 A | 10/1999 | Rudolph et al. |
| 5,983,892 A | 11/1999 | Thornton |
| 5,984,857 A | 11/1999 | Buck et al. |
| 6,055,986 A | 5/2000 | Meade |
| 6,085,747 A | 7/2000 | Axe et al. |
| 6,131,581 A | 10/2000 | Leysieffer et al. |
| 6,155,262 A | 12/2000 | Thornton et al. |
| 6,253,764 B1 | 7/2001 | Calluaud |
| 6,257,235 B1 | 7/2001 | Bowen |
| 6,273,859 B1 | 8/2001 | Remmers et al. |
| 6,283,119 B1 | 9/2001 | Bourdon |
| 6,294,281 B1 | 9/2001 | Heller |
| 6,302,105 B1 | 10/2001 | Wickham et al. |
| 6,305,376 B1 | 10/2001 | Thornton |
| 6,349,724 B1 * | 2/2002 | Burton et al. ............ 128/204.18 |
| 6,371,112 B1 | 4/2002 | Bibi |
| 6,371,120 B1 | 4/2002 | Chiu et al. |
| 6,374,824 B1 | 4/2002 | Thornton |
| 6,386,201 B1 | 5/2002 | Fard |
| 6,401,714 B1 | 6/2002 | Giorgini |
| 6,405,729 B1 | 6/2002 | Thornton |
| 6,411,852 B1 | 6/2002 | Danek et al. |
| 6,425,393 B1 | 7/2002 | Lurie et al. |
| 6,427,689 B1 | 8/2002 | Estes et al. |
| 6,433,465 B1 | 8/2002 | McKnight et al. |
| 6,435,184 B1 | 8/2002 | Ho |
| 6,457,471 B1 | 10/2002 | Bibi |
| 6,470,212 B1 | 10/2002 | Weijand et al. |
| 6,484,719 B1 | 11/2002 | Berthon-Jones |
| 6,494,209 B2 | 12/2002 | Kulick |
| 6,500,571 B2 | 12/2002 | Liberatore et al. |
| 6,503,648 B1 | 1/2003 | Wang |
| 6,510,846 B1 | 1/2003 | O'Rourke |
| 6,526,970 B2 | 3/2003 | DeVries et al. |
| 6,531,239 B2 | 3/2003 | Heller |
| 6,532,957 B2 | 3/2003 | Berthon-Jones |
| 6,546,286 B2 | 4/2003 | Olson |
| 6,581,598 B1 | 6/2003 | Foran et al. |
| 6,595,212 B1 | 7/2003 | Arnott |
| 6,629,527 B1 | 10/2003 | Estes et al. |
| 6,629,529 B2 | 10/2003 | Arnott |
| 6,640,137 B2 | 10/2003 | MacDonald |
| 6,659,100 B2 | 12/2003 | O'Rourke |
| 6,705,314 B1 | 3/2004 | O'Dea |
| 6,722,360 B2 | 4/2004 | Doshi |
| 6,763,828 B2 | 7/2004 | Arnott |
| 6,772,762 B2 | 8/2004 | Piesinger |
| 6,786,216 B2 | 9/2004 | O'Rourke |
| 6,792,942 B1 | 9/2004 | Ho et al. |
| 6,810,876 B2 | 11/2004 | Berthon-Jones |
| 6,822,343 B2 | 11/2004 | Estevez |
| 6,827,682 B2 | 12/2004 | Bugge et al. |
| 6,828,908 B2 | 12/2004 | Clark |
| 6,845,774 B2 | 1/2005 | Gaskell |
| 6,854,464 B2 | 2/2005 | Mukaiyama et al. |
| 6,877,511 B2 | 4/2005 | DeVries et al. |
| 6,877,513 B2 | 4/2005 | Scarberry et al. |
| 6,883,518 B2 | 4/2005 | Mittelstadt et al. |
| 6,895,959 B2 | 5/2005 | Lukas |
| 6,895,962 B2 | 5/2005 | Kullik et al. |
| 6,895,964 B2 | 5/2005 | McAuliffe et al. |
| 6,945,926 B2 | 9/2005 | Trumble |
| 6,948,497 B2 | 9/2005 | Zdrojkowski et al. |
| 6,970,744 B1 | 11/2005 | Shelchuk |
| 6,988,994 B2 | 1/2006 | Rapoport et al. |
| 6,990,980 B2 | 1/2006 | Richey |
| 6,997,177 B2 | 2/2006 | Wood |
| 7,018,735 B2 | 3/2006 | Heller |
| 7,025,730 B2 | 4/2006 | Cho et al. |
| 7,032,589 B2 | 4/2006 | Kerechanin et al. |
| 7,036,506 B2 | 5/2006 | McAuliffe et al. |
| 7,044,129 B1 | 5/2006 | Truschel et al. |
| 7,059,324 B2 | 6/2006 | Pelerossi et al. |
| 7,066,177 B2 | 6/2006 | Pittaway et al. |
| 7,080,645 B2 | 7/2006 | Genger et al. |
| 7,080,646 B2 | 7/2006 | Wiesmann et al. |
| 7,081,683 B2 | 7/2006 | Ariav |
| 7,100,607 B2 | 9/2006 | Zdrojkowski et al. |
| 7,114,497 B2 | 10/2006 | Aylsworth et al. |
| 7,127,293 B2 | 10/2006 | MacDonald |
| 7,128,069 B2 | 10/2006 | Farrugia et al. |
| 7,152,598 B2 | 12/2006 | Morris et al. |
| 7,160,637 B2 | 1/2007 | Chiao et al. |
| 7,188,621 B2 | 3/2007 | DeVries et al. |
| 7,195,014 B2 | 3/2007 | Hoffman |
| 7,195,015 B2 | 3/2007 | Kuriyama |
| 7,203,551 B2 | 4/2007 | Houben et al. |
| 7,218,009 B2 | 5/2007 | Hendrickson et al. |
| 7,222,623 B2 | 5/2007 | DeVries et al. |
| 7,238,442 B2 | 7/2007 | Heller |
| 7,246,619 B2 | 7/2007 | Truschel et al. |
| 7,275,542 B2 | 10/2007 | Lurie et al. |
| 7,284,554 B2 | 10/2007 | Shaw |
| 7,320,321 B2 | 1/2008 | Pranger et al. |
| 7,334,581 B2 | 2/2008 | Doshi |
| 7,340,304 B2 | 3/2008 | MacDonald |
| 7,345,407 B2 | 3/2008 | Tanner |
| 7,368,190 B2 | 5/2008 | Heller et al. |

(56) References Cited

U.S. PATENT DOCUMENTS

| | | |
|---|---|---|
| 7,370,650 B2 | 5/2008 | Nadjafizadeh et al. |
| 7,387,608 B2 | 6/2008 | Dunlop et al. |
| 7,406,963 B2 | 8/2008 | Chang et al. |
| 7,406,966 B2 | 8/2008 | Wondka |
| 7,414,351 B2 | 8/2008 | Ulm et al. |
| 7,448,383 B2 | 11/2008 | Delache et al. |
| 7,451,766 B2 | 11/2008 | Miller |
| 7,464,705 B2 | 12/2008 | Tanizawa et al. |
| 7,469,697 B2 | 12/2008 | Lee et al. |
| 7,506,649 B2 | 3/2009 | Doshi et al. |
| 7,516,743 B2 | 4/2009 | Hoffman |
| 7,527,055 B2 | 5/2009 | McAuliffe et al. |
| 7,533,670 B1 | 5/2009 | Freitag et al. |
| 7,560,856 B2 | 7/2009 | Chen et al. |
| 7,562,657 B2 | 7/2009 | Blanch et al. |
| 7,562,659 B2 | 7/2009 | Matarasso |
| 7,575,005 B2 | 8/2009 | Mumford et al. |
| 7,644,714 B2 | 1/2010 | Atkinson et al. |
| 7,650,885 B2 | 1/2010 | Paoluccio et al. |
| 7,658,192 B2 | 2/2010 | Harrington |
| 7,686,013 B2 | 3/2010 | Chang et al. |
| 7,694,679 B2 | 4/2010 | McAuliffe et al. |
| 7,699,054 B2 | 4/2010 | Pelerossi et al. |
| 7,709,134 B2 | 5/2010 | Minteer et al. |
| 7,715,918 B2 | 5/2010 | Melvin |
| 7,716,988 B2 | 5/2010 | Ariav et al. |
| 7,721,736 B2 | 5/2010 | Urias et al. |
| 7,725,195 B2 | 5/2010 | Lima et al. |
| RE41,394 E | 6/2010 | Bugge et al. |
| 7,726,305 B2 | 6/2010 | Chang et al. |
| 7,729,767 B2 | 6/2010 | Baker et al. |
| 7,729,768 B2 | 6/2010 | White et al. |
| 7,735,491 B2 | 6/2010 | Doshi et al. |
| 7,735,492 B2 | 6/2010 | Doshi et al. |
| 7,762,263 B2 | 7/2010 | Aarestad et al. |
| 7,779,841 B2 | 8/2010 | Dunsmore et al. |
| 7,789,837 B2 | 9/2010 | Lehrman et al. |
| 7,793,660 B2 | 9/2010 | Kimmel et al. |
| 7,793,661 B2 | 9/2010 | Macken |
| 7,798,148 B2 | 9/2010 | Doshi et al. |
| 7,800,278 B2 | 9/2010 | Ujihara et al. |
| 7,806,120 B2 | 10/2010 | Loomas et al. |
| 7,809,442 B2 | 10/2010 | Bolea et al. |
| 7,811,689 B2 | 10/2010 | Heller |
| 7,813,810 B2 | 10/2010 | Cernasov |
| 7,823,590 B2 | 11/2010 | Bibi et al. |
| 7,835,529 B2 | 11/2010 | Hernandez et al. |
| 7,841,343 B2 | 11/2010 | Deane et al. |
| 7,849,854 B2 | 12/2010 | DeVries et al. |
| 7,856,979 B2 | 12/2010 | Doshi et al. |
| 7,866,212 B2 | 1/2011 | Ariav et al. |
| 7,866,318 B2 | 1/2011 | Bassin |
| 7,866,944 B2 | 1/2011 | Kenyon et al. |
| 7,874,290 B2 | 1/2011 | Chalvignac |
| 7,875,048 B2 | 1/2011 | Dillard et al. |
| 7,901,361 B2 | 3/2011 | Rapoport et al. |
| 7,902,727 B1 | 3/2011 | Sham et al. |
| 7,909,035 B2 | 3/2011 | Thornton |
| 7,909,038 B2 | 3/2011 | Hegde et al. |
| 7,913,692 B2 | 3/2011 | Kwok |
| 7,921,850 B2 | 4/2011 | Nelson et al. |
| 7,927,749 B2 | 4/2011 | Swift et al. |
| 7,934,506 B2 | 5/2011 | Woodson et al. |
| 7,937,159 B2 | 5/2011 | Lima et al. |
| 7,942,380 B2 | 5/2011 | Bertinetti et al. |
| 7,942,824 B1 | 5/2011 | Kayyali et al. |
| 7,951,357 B2 | 5/2011 | Gross et al. |
| 7,954,494 B1 | 6/2011 | Connor |
| 7,958,895 B2 | 6/2011 | Nelson et al. |
| 7,958,896 B2 | 6/2011 | Nelson et al. |
| 7,967,014 B2 | 6/2011 | Heidmann et al. |
| 7,975,700 B2 | 7/2011 | Frazier et al. |
| 7,976,968 B2 | 7/2011 | Siu et al. |
| 7,977,807 B1 | 7/2011 | Connor |
| 7,987,852 B2 | 8/2011 | Doshi et al. |
| 7,992,563 B2 | 8/2011 | Doshi |
| 7,992,564 B2 | 8/2011 | Doshi et al. |
| 7,992,566 B2 | 8/2011 | Pflueger et al. |
| 7,997,266 B2 | 8/2011 | Frazier et al. |
| 7,998,624 B2 | 8/2011 | Heller |
| 7,998,625 B2 | 8/2011 | Heller |
| 8,003,879 B2 | 8/2011 | Erbstoeszer et al. |
| 8,011,362 B2 | 9/2011 | Adams |
| 8,011,365 B2 | 9/2011 | Douglas et al. |
| 8,015,974 B2 | 9/2011 | Christopher et al. |
| 8,020,556 B2 | 9/2011 | Hayek |
| 8,020,557 B2 | 9/2011 | Bordewick et al. |
| 8,020,558 B2 | 9/2011 | Christopher et al. |
| 8,020,700 B2 | 9/2011 | Doshi et al. |
| 8,024,044 B2 | 9/2011 | Kirby et al. |
| 8,025,054 B2 | 9/2011 | Dunsmore et al. |
| 8,028,705 B2 | 10/2011 | Li |
| 8,037,885 B2 | 10/2011 | Metzger et al. |
| 8,039,727 B2 | 10/2011 | Erbstoeszer et al. |
| 8,047,206 B2 | 11/2011 | Boucher et al. |
| 8,048,547 B2 | 11/2011 | Ringeisen et al. |
| 8,051,850 B2 | 11/2011 | Kwok et al. |
| 8,051,853 B2 | 11/2011 | Berthon-Jones |
| 8,061,357 B2 | 11/2011 | Pierce et al. |
| 8,068,904 B2 | 11/2011 | Sun et al. |
| 8,069,853 B2 | 12/2011 | Tilley |
| 8,074,647 B2 | 12/2011 | Truitt et al. |
| 8,074,655 B2 | 12/2011 | Sanders |
| 8,074,656 B2 | 12/2011 | Vaska et al. |
| 2001/0011825 A1* | 8/2001 | de Vega .......................... 290/55 |
| 2002/0050719 A1* | 5/2002 | Caddell et al. .................. 290/54 |
| 2002/0104541 A1 | 8/2002 | Bibi et al. |
| 2003/0066527 A1 | 4/2003 | Chen |
| 2003/0167018 A1 | 9/2003 | Wyckoff |
| 2003/0172930 A1 | 9/2003 | Kullik et al. |
| 2004/0021322 A1 | 2/2004 | Ariav |
| 2004/0073267 A1 | 4/2004 | Holzer |
| 2004/0079373 A1 | 4/2004 | Mukaiyama et al. |
| 2004/0093041 A1 | 5/2004 | MacDonald |
| 2004/0158294 A1 | 8/2004 | Thompson |
| 2004/0168689 A1 | 9/2004 | Kuriyama |
| 2004/0216741 A1* | 11/2004 | Arnott ...................... 128/204.18 |
| 2004/0237965 A1 | 12/2004 | Bibi et al. |
| 2005/0027332 A1 | 2/2005 | Avrahami et al. |
| 2005/0034724 A1 | 2/2005 | O'Dea |
| 2005/0081859 A1 | 4/2005 | Scarberry et al. |
| 2005/0171580 A1 | 8/2005 | MacDonald |
| 2005/0236003 A1 | 10/2005 | Meader |
| 2006/0096596 A1 | 5/2006 | Occhialini et al. |
| 2006/0144398 A1 | 7/2006 | Doshi et al. |
| 2006/0150978 A1 | 7/2006 | Doshi et al. |
| 2006/0150979 A1 | 7/2006 | Doshi et al. |
| 2006/0180149 A1 | 8/2006 | Matarasso |
| 2006/0213516 A1 | 9/2006 | Hoffman |
| 2006/0237013 A1 | 10/2006 | Kwok |
| 2007/0000493 A1 | 1/2007 | Cox |
| 2007/0173893 A1 | 7/2007 | Pitts |
| 2007/0215156 A1 | 9/2007 | Kwok |
| 2007/0246045 A1 | 10/2007 | Hoffman |
| 2007/0251244 A1 | 11/2007 | Erbstoeszer et al. |
| 2007/0251527 A1 | 11/2007 | Sleeper |
| 2007/0253227 A1 | 11/2007 | James et al. |
| 2007/0277827 A1 | 12/2007 | Bordewick et al. |
| 2007/0277832 A1 | 12/2007 | Doshi et al. |
| 2007/0283962 A1 | 12/2007 | Doshi et al. |
| 2007/0295338 A1 | 12/2007 | Loomas et al. |
| 2008/0029098 A1 | 2/2008 | Ottestad |
| 2008/0041373 A1 | 2/2008 | Doshi et al. |
| 2008/0053438 A1 | 3/2008 | DeVries et al. |
| 2008/0060649 A1 | 3/2008 | Veliss et al. |
| 2008/0060660 A1 | 3/2008 | Nelson et al. |
| 2008/0109047 A1 | 5/2008 | Pless |
| 2008/0135044 A1 | 6/2008 | Freitag et al. |
| 2008/0142013 A1 | 6/2008 | Hallett et al. |
| 2008/0142018 A1 | 6/2008 | Doshi et al. |
| 2008/0173309 A1 | 7/2008 | Doshi |
| 2008/0178874 A1 | 7/2008 | Doshi et al. |
| 2008/0178879 A1 | 7/2008 | Roberts et al. |
| 2008/0196720 A1 | 8/2008 | Kollmeyer et al. |

(56) References Cited

U.S. PATENT DOCUMENTS

| | | |
|---|---|---|
| 2008/0216831 A1 | 9/2008 | McGinnis et al. |
| 2008/0216835 A1 | 9/2008 | McGinnis et al. |
| 2008/0221470 A1 | 9/2008 | Sather et al. |
| 2008/0251079 A1 | 10/2008 | Richey |
| 2009/0020121 A1 | 1/2009 | Bassin |
| 2009/0050144 A1 | 2/2009 | Pierce et al. |
| 2009/0078273 A1 | 3/2009 | Bhat et al. |
| 2009/0120446 A1 | 5/2009 | Vaska et al. |
| 2009/0145441 A1 | 6/2009 | Doshi et al. |
| 2009/0152990 A1 | 6/2009 | Brown et al. |
| 2009/0165799 A1 | 7/2009 | Duquette et al. |
| 2009/0188493 A1 | 7/2009 | Doshi et al. |
| 2009/0194100 A1 | 8/2009 | Minagi |
| 2009/0194109 A1 | 8/2009 | Doshi et al. |
| 2009/0216292 A1 | 8/2009 | Pless et al. |
| 2009/0241965 A1 | 10/2009 | Sather et al. |
| 2009/0308398 A1 | 12/2009 | Ferdinand et al. |
| 2009/0320842 A1 | 12/2009 | Doherty et al. |
| 2010/0000543 A1 | 1/2010 | Berthon-Jones et al. |
| 2010/0006097 A1 | 1/2010 | Frater et al. |
| 2010/0043796 A1 | 2/2010 | Meynink et al. |
| 2010/0063557 A1 | 3/2010 | Imran |
| 2010/0076517 A1 | 3/2010 | Imran |
| 2010/0078016 A1 | 4/2010 | Andrieux et al. |
| 2010/0078017 A1 | 4/2010 | Andrieux et al. |
| 2010/0108070 A1 | 5/2010 | Kwok |
| 2010/0114142 A1 | 5/2010 | Albrecht et al. |
| 2010/0121406 A1 | 5/2010 | Libbus et al. |
| 2010/0132708 A1 | 6/2010 | Martin et al. |
| 2010/0132719 A1 | 6/2010 | Jacobs et al. |
| 2010/0137905 A1 | 6/2010 | Weadock et al. |
| 2010/0139668 A1 | 6/2010 | Harrington |
| 2010/0147302 A1 | 6/2010 | Selvarajan et al. |
| 2010/0163043 A1 | 7/2010 | Hart et al. |
| 2010/0163046 A1 | 7/2010 | Fisher et al. |
| 2010/0170513 A1* | 7/2010 | Bowditch et al. ........ 128/204.23 |
| 2010/0171394 A1 | 7/2010 | Glenn et al. |
| 2010/0180895 A1 | 7/2010 | Kwok et al. |
| 2010/0198306 A1 | 8/2010 | Lima et al. |
| 2010/0199985 A1 | 8/2010 | Hamilton et al. |
| 2010/0242967 A1 | 9/2010 | Burbank et al. |
| 2010/0252042 A1 | 10/2010 | Kapust et al. |
| 2010/0269834 A1 | 10/2010 | Freitag et al. |
| 2010/0275910 A1 | 11/2010 | Aarestad et al. |
| 2010/0280626 A1 | 11/2010 | Shalon et al. |
| 2010/0298720 A1 | 11/2010 | Potkay |
| 2010/0307487 A1 | 12/2010 | Dunsmore et al. |
| 2010/0313898 A1 | 12/2010 | Richard et al. |
| 2010/0317977 A1 | 12/2010 | Piaget et al. |
| 2010/0317978 A1 | 12/2010 | Maile et al. |
| 2010/0319711 A1 | 12/2010 | Hegde et al. |
| 2010/0326447 A1 | 12/2010 | Loomas et al. |
| 2010/0331877 A1 | 12/2010 | Li et al. |
| 2011/0005520 A1 | 1/2011 | Doshi et al. |
| 2011/0005529 A1 | 1/2011 | Doshi et al. |
| 2011/0005530 A1 | 1/2011 | Doshi et al. |
| 2011/0056499 A1 | 3/2011 | Doshi et al. |
| 2011/0066086 A1 | 3/2011 | Aarestad et al. |
| 2011/0067708 A1 | 3/2011 | Doshi et al. |
| 2011/0067709 A1 | 3/2011 | Doshi et al. |
| 2011/0071591 A1 | 3/2011 | Bolea et al. |
| 2011/0073110 A1 | 3/2011 | Kenyon et al. |
| 2011/0073119 A1 | 3/2011 | Chen et al. |
| 2011/0079224 A1 | 4/2011 | Arnott |
| 2011/0112601 A1 | 5/2011 | Meadows et al. |
| 2011/0152966 A1 | 6/2011 | Bolea et al. |
| 2011/0166598 A1 | 7/2011 | Gonazles et al. |
| 2011/0180075 A1 | 7/2011 | Chen et al. |
| 2011/0180076 A1 | 7/2011 | Hegde et al. |
| 2011/0192404 A1 | 8/2011 | Chen |
| 2011/0196445 A1 | 8/2011 | Bolea et al. |
| 2011/0202106 A1 | 8/2011 | Bolea et al. |
| 2011/0203587 A1 | 8/2011 | Bertinetti et al. |
| 2011/0203592 A1 | 8/2011 | Adams |
| 2011/0203598 A1 | 8/2011 | Favet et al. |
| 2011/0208010 A1 | 8/2011 | McKenna |
| 2011/0214673 A1 | 9/2011 | Masionis |
| 2011/0218451 A1 | 9/2011 | Lai et al. |
| 2011/0220123 A1 | 9/2011 | Robson |
| 2011/0220124 A1 | 9/2011 | Vaska et al. |
| 2011/0232652 A1 | 9/2011 | Levendowski et al. |
| 2011/0240038 A1 | 10/2011 | Doshi et al. |
| 2011/0259346 A1 | 10/2011 | Tsuiki et al. |
| 2011/0264164 A1 | 10/2011 | Christopherson et al. |
| 2011/0270031 A1 | 11/2011 | Frazier et al. |
| 2011/0270043 A1 | 11/2011 | McKenna |
| 2011/0275947 A1 | 11/2011 | Feldman et al. |
| 2011/0277765 A1 | 11/2011 | Christopher et al. |
| 2011/0284003 A1 | 11/2011 | Douglas et al. |
| 2011/0290256 A1 | 12/2011 | Sather et al. |
| 2011/0290258 A1 | 12/2011 | Pflueger et al. |
| 2011/0295083 A1 | 12/2011 | Doelling et al. |
| 2011/0301679 A1 | 12/2011 | Rezai et al. |
| 2011/0308529 A1 | 12/2011 | Gillis et al. |
| 2011/0308530 A1 | 12/2011 | Gillis et al. |

* cited by examiner

ENERGY-HARVESTING RESPIRATORY METHOD AND DEVICE

CROSS-REFERENCE TO RELATED APPLICATIONS

This patent application claims the priority benefit of U.S. Provisional Patent Application No. 61/465,196 entitled "Energy-Harvesting Respiratory Device" filed on Mar. 14, 2011 by Robert A. Connor.

FEDERALLY SPONSORED RESEARCH

Not Applicable

SEQUENCE LISTING OR PROGRAM

Not Applicable

BACKGROUND

Field of Invention

This invention relates to treating respiratory conditions such as Obstructive Sleep Apnea (OSA).

INTRODUCTION TO OBSTRUCTIVE SLEEP APNEA (OSA)

Obstructive Sleep Apnea (OSA) is intermittent blockage of a person's airway while they sleep. Such blockages can occur hundreds of times each night, causing poor sleep and oxygen deprivation. Obstructive sleep apnea can cause serious long-term harmful effects. These harmful effects include: disrupted sleep; chronic fatigue; morning headaches; irritability; brain damage; cognitive dysfunction; impotency; high blood pressure; heart attacks; congestive heart failure; motor vehicle crashes; job-site accidents; and even death. Despite these harmful effects, it is estimated that only 5% to 8% of the affected population are treated. Approximately 20 million Americans and 35 million people worldwide have obstructive sleep apnea and the number is growing rapidly.

Positive airway pressure is a common therapy for OSA. Positive airway pressure can help to keep soft tissue from collapsing into the airway. Variations on positive airway pressure include Continuous Positive Airway Pressure (CPAP) and Positive End Expiratory Pressure (PEEP). CPAP provides virtually continuous positive airway pressure. PEEP provides positive airway pressure at selected times, primarily between exhalation and inhalation. Positive airway pressure can also be useful for other respiratory conditions. Positive airway pressure can be provided by an active energy-using air-moving device such as an electricity-powered air pump. Virtually all such air pumps in the prior art require either a direct connection to an external power source or have a battery that must be repeatedly recharged. Generally air from a bedside air pump unit is channeled via an air tube into a mask, or nasal inserts, which a person wears while they sleep.

However, there are millions people around the world with Obstructive Sleep Apnea (OSA) who are not receiving positive airway pressure treatment. Many of these people do not have access to dependable external power for direct operation of an air pump or for repeatedly recharging the battery thereof. For them, an energy-harvesting device that does not require an external source of power would be a tremendous breakthrough. Also, even among people who have access to external power, many people cannot tolerate being tethered to a bedside unit by an air tube while they sleep. They get tangled up in the tube as they toss and turn during sleep. Rolling over onto the tube can cut off their air supply. Finally, an energy self-sufficient positive airway pressure option would be extremely useful for camping, for travel, and for emergency conditions (hurricanes, earthquakes, etc) during which external power is not available. The invention that is disclosed herein can meet these needs. This invention can provide a novel, unique, and advantageous positive airway pressure treatment option for the millions of people with Obstructive Sleep Apnea (OSA) who are not currently receiving positive airway pressure therapy.

CATEGORIZATION AND REVIEW OF THE PRIOR ART

It can often be challenging to classify prior art into discrete categories. That is the case in this field. There are several hundred examples of potentially-relevant prior art related to this invention, ranging from prior art concerning harvesting energy from the human body to prior art that provides respiratory support for people with Obstructive Sleep Apnea (OSA) and other respiratory conditions.

However, classification of the prior art into categories, even if imperfect, can be an invaluable tool for reviewing the prior art, identifying its limitations, and setting the stage for discussion of the advantages of the present invention that is disclosed in subsequent sections. Towards this end, I have identified 17 general categories of prior art (and a final miscellaneous category), identified examples of prior art which appear to be best classified into these categories, and then identified key limitations of the prior art which should be addressed. These limitations are addressed by the invention which is disclosed in subsequent sections.

The 18 categories of prior art that I will now discuss are as follows: (1) energy harvested from muscle motion; (2) energy harvested from internal fluid flow; (3) energy harvested from internal biological source; (4) energy harvested from internal thermal energy; (5) energy harvested from external pressurized gas; (6) air pump/blower: wearable; (7) air pump/blower: portable, but not wearable; (8) air pump/blower: sensor interactive and variable pressure; (9) passive exhalation resistance device; (10) tongue engaging device: suction/friction; (11) tongue engaging device: implant/anchor; (12) tongue engaging device: nerve stimulation; (13) airway engaging device: stent or magnet; (14) outward force on body surface: external negative pressure; (15) mouth insert/appliance; (16) one-way valve in lung; (17) external response to sensor; and (18) other potentially-relevant art.

1. Energy Harvested from Muscle Motion

This first category of prior art includes methods, devices, and systems that harvest energy from the motion of human muscles. Some of these methods and devices harvest energy directly by connection to human muscles. Other devices in this category harvest energy indirectly, by connection with tissues of the human body that are, in turn, moved by human muscles. Most of this prior art transduces energy from movement of human muscles into electricity. This electricity is generally intended to power implanted medical devices, such as pacemakers, in order to eliminate the need for recharging a battery from an external power source.

For the purposes of this review, almost all of the examples of prior art that are included in this category are implanted devices that harvest energy from within the human body. A few external energy-harvesting devices (such as those attached to the surface of a human body) are included, but I have not included the wide range of external devices (hand cranks, shoe-based generators, etc.) that harvest energy from human motion.

Examples of methods and devices in the prior art that appear to involve energy harvested from muscle motion include the following: U.S. Pat. No. 3,456,134 (Ko 1969, "Piezoelectric Energy Converter for Electronic Implants"); U.S. Pat. No. 3,906,960 (Lehr 1975, "Medical Energy Converter"); U.S. Pat. No. 4,140,132 (Dahl 1979, "Variable Rate Timer for a Cardiac Pacemaker"); U.S. Pat. No. 4,245,640 (Hunt 1981, "Chest Motion Electricity Generating Device"); U.S. Pat. No. 4,690,143 (Schroeppel 1987, "Pacing Lead with Piezoelectric Power Generating Means"); U.S. Pat. No. 4,798,206 (Maddison et al. 1989, "Implanted Medical System Including a Self-Powered Sensing System"); U.S. Pat. No. 5,344,385 (Buck et al. 1994, "Step-Down Skeletal Muscle Energy Conversion System"); U.S. Pat. No. 5,431,694 (Snaper et al. 1995, "Bio-Operable Power Source"); U.S. Pat. No. 5,443,504 (Hill 1995, "Basic Skeletal Muscle Energy Conversion System"); U.S. Pat. No. 5,479,946 (Trumble 1996, "Muscle Energy Converter"); U.S. Pat. No. 5,540,729 (Weijand 1996, "Movement Powered Medical Pulse Generator Having a Full-Wave Rectifier with Dynamic Bias"); U.S. Pat. No. 5,653,676 (Buck et al. 1997, "Step-Down Skeletal Muscle Energy Conversion Method"); U.S. Pat. No. 5,701,919 (Buck et al. 1997, "Step-Down Skeletal Muscle Energy Conversion System"); U.S. Pat. No. 5,718,248 (Trumble et al. 1998, "Muscle Energy Converter Pump and Method of Pumping Fluid of a Patient"); U.S. Pat. No. 5,810,015 (Flaherty 1998, "Power Supply for Implantable Device"); U.S. Pat. No. 5,888,186 (Trumble et al. 1999, "Muscle Energy Converter Activated Assist System and Method"); U.S. Pat. No. 5,954,058 (Flaherty 1999, "Power Supply for Implantable Device"); U.S. Pat. No. 5,984,857 (Buck et al. 1999, "Step-Down Skeletal Muscle Energy Conversion System"); and U.S. Pat. No. 6,433,465 (McKnight et al. 2002, "Energy-Harvesting Device Using Electrostrictive Polymers").

Examples of prior art in this category also include: U.S. Pat. No. 6,546,286 (Olson 2003, "Battery-Less, Human-Powered Electrotherapy Device"); U.S. Pat. No. 6,828,908 (Clark 2004, "Locator System with an Implanted Transponder Having an Organically-Rechargeable Battery"); U.S. Pat. No. 6,945,926 (Trumble 2005, "Muscle Energy Converter"); U.S. Pat. No. 7,203,551 (Houben et al. 2007, "Implantable Lead-Based Sensor Powered by Piezoelectric Transformer"); U.S. Pat. No. 7,345,407 (Tanner 2008, "Human Powered Piezoelectric Power Generating Device"); U.S. Pat. No. 7,414,351 (Ulm et al. 2008, "Energy Harvesting Device Manufactured by Print Forming Processes"); U.S. Pat. No. 7,715,918 (Melvin 2010, "Muscle Energy Converter with Smooth Continuous Tissue Interface"); U.S. Pat. No. 7,729,767 (Baker et al. 2010, "Implantable Generating System"); U.S. Pat. No. 7,729,768 (White et al. 2010, "Implantable Cardiac Motion Powered Piezoelectric Energy Source"); U.S. Pat. No. 7,800,278 (Ujihara et al. 2010, "Energy Harvesting By Means Of Thermo-Mechanical Device Utilizing Bistable Ferromagnets"); U.S. Pat. No. 7,902,727 (Sham et al. 2011, "Apparatus and Method for Generating Electricity Using Piezoelectric Material"); and U.S. Pat. No. 7,977,807 (Connor 2011, "Wearable Device to Generate Electricity from Human Movement");

Examples of prior art in this category also include: U.S. Patent Applications 20040073267 (Holzer 2004, "Micro-Generator Implant"); 20040158294 (Thompson 2004, "Self-Powered Implantable Element"); 20090152990 (Brown et al. 2009, "Apparatus for In Vivo Energy Harvesting"); 20090216292 (Pless et al. 2009, "Devices, Methods, and Systems for Harvesting Energy in the Body"); 20100063557 (Imran 2010, "Energy Harvesting Mechanism"); 20100076517 (Imran 2010, "Energy Harvesting Mechanism for Medical Devices"); 20100114142 (Albrecht et al. 2010, "Powering Implantable Distension Systems Using Internal Energy Harvesting Means"); 20100171394 (Glenn et al. 2010, "Energy Harvesting for Implanted Medical Devices"); 20100298720 (Potkay 2010, "In Situ Energy Harvesting Systems for Implanted Medical Devices"); 20100317977 (Piaget et al. 2010, "Implantable Medical Device with Internal Piezoelectric Energy Harvesting"); 20100317978 (Maile et al. 2010, "Implantable Medical Device Housing Modified for Piezoelectric Energy Harvesting"); 20110208010 (McKenna 2011, "Motion Energy Harvesting with Wireless Sensors"); and 20110275947 (Feldman et al. 2011, "Cardiovascular Power Source for Automatic Implantable Cardioverter Defibrillators").

2. Energy Harvested from Internal Fluid Flow

This category of prior art includes methods, devices, and systems that harvest energy from flowing fluid within the human body. Some of this prior art harvests energy directly from a flowing fluid. Other examples of art in this category harvest energy indirectly, from tissue movement caused by variation in fluid pressure such as pulsation of the walls of a blood vessel. Devices in the prior art in this category are generally implanted within the human body. They are generally intended to power an implantable medical device such as a pacemaker.

In some respects, this category could be viewed as a subset of the previous category concerning harvesting energy from the movement of human muscles. Fluid flow within the body can generally be traced back to muscle movement, especially the beating of the heart muscle. However, I have listed energy harvesting from fluid flow as a separate category because harvesting energy from fluid flow can be seen as being closer to harvesting energy from gas flow than to harvesting energy from movement of solid body members.

Examples of methods and devices in the prior art that appear to involve harvesting energy from internal fluid flow include the following: U.S. Pat. No. 3,563,245 (McLean et al. 1971, "Biologically Implantable and Energized Power Supply"); U.S. Pat. No. 3,693,625 (Auphan 1972, "Heart Stimulator and Heart-Powered Energy Supply Therefor"); U.S. Pat. No. 3,943,936 (Rasor et al. 1976, "Self Powered Pacers And Stimulators"); U.S. Pat. No. 4,453,537 (Spitzer 1984, "Apparatus for Powering a Body Implant Device"); U.S. Pat. No. 6,822,343 (Estevez 2004, "Generating Electric Power in Response to Activity of a Biological System"); U.S. Pat. No. 6,827,682 (Bugge et al. 2004, "Implantable Device for Utilization of the Hydraulic Energy of the Heart"); U.S. Pat. No. 7,081,683 (Ariav 2006, "Method and Apparatus for Body Generation of Electrical Energy"); U.S. Pat. No. 7,560,856 (Chen et al. 2009, "Harvesting Energy from Flowing Fluid"); U.S. Pat. No. 7,813,810 (Cernasov 2010, "Apparatus and Method for Supplying Power to Subcutaneously Implanted Devices"); and RE41394 (Bugge et al. 2010, "Implantable Device for Utilization of the Hydraulic Energy of the Heart"); and U.S. Patent Application 20040021322 (Ariav 2004, "Method and Apparatus for Body Generation of Electrical Energy").

3. Energy Harvested from Internal Biological Source

This category of prior art includes methods, devices, and systems that harvest energy from biological and/or chemical processes within the human body. This category includes implanted biological fuel cells and chemical fuel cells that generate electricity within the human body. Devices in this category are generally intended to power an implanted medical device such as a pacemaker. In an example, methods and devices in this category may use a person's own body tissue and biochemical processes to generate power. In other examples, methods and devices in this category may implant a biological fuel cell that contains foreign biological members or chemicals that are used to generate power.

Examples of methods and devices in the prior art that appear to involve harvesting energy from an internal biological source include the following: U.S. Pat. No. 3,305,399 (Davis 1967, "Microbial Process of Producing Electricity"); U.S. Pat. No. 3,421,512 (Frasier 1969, "Implanted Electrical Device with Biological Power Supply"); U.S. Pat. No. 3,774,243 (Ng et al. 1973, "Implantable Power System for an Artificial Heart"); U.S. Pat. No. 3,861,397 (Rao et al. 1975, "Implantable Fuel Cell"); U.S. Pat. No. 3,941,135 (von Sturm et al. 1976, "Pacemaker with Biofuel Cell"); U.S. Pat. No. 5,810,015 (Flaherty 1998, "Power Supply for Implantable Device"); U.S. Pat. No. 5,954,058 (Flaherty 1999, "Power Supply for Implantable Device"); U.S. Pat. No. 6,294,281 (Heller 2001, "Biological Fuel Cell and Method"); U.S. Pat. No. 6,500,571 (Liberatore et al. 2002, "Enzymatic Fuel Cell"); U.S. Pat. No. 6,503,648 (Wang 2003, "Implantable Fuel Cell"); U.S. Pat. No. 6,531,239 (Heller 2003, "Biological Fuel Cell and Methods"); U.S. Pat. No. 6,970,744 (Shelchuk 2005, "Bioenergy Generator"); U.S. Pat. No. 7,018,735 (Heller 2006, "Biological Fuel Cell and Methods"); U.S. Pat. No. 7,160,637 (Chiao et al. 2007, "Implantable, Miniaturized Microbial Fuel Cell"); U.S. Pat. No. 7,238,442 (Heller 2007, "Biological Fuel Cell and Methods"); U.S. Pat. No. 7,368,190 (Heller et al. 2008, "Miniature Biological Fuel Cell that is Operational Under Physiological Conditions, and Associated Devices and Methods"); U.S. Pat. No. 7,709,134 (Minteer et al. 2010, "Microfluidic Biofuel Cell"); U.S. Pat. No. 7,811,689 (Heller 2010, "Biological Fuel Cell and Methods"); U.S. Pat. No. 7,927,749 (Swift et al. 2011, "Microbial Fuel Cell and Method"); U.S. Pat. No. 7,976,968 (Siu et al. 2011, "Microbial Fuel Cell With Flexible Substrate and Micro-Pillar Structure"); U.S. Pat. No. 7,998,624 (Heller 2011, "Biological Fuel Cell and Methods"); U.S. Pat. No. 7,998,625 (Heller 2011, "Biological Fuel Cell and Methods"); and U.S. Pat. No. 8,048,547 (Ringeisen et al. 2011, "Biological Fuel Cells with Nanoporous Membranes"); and U.S. Patent Application 20050027332 (Avrahami et al. 2005, "Implanted Autonomic Energy Source").

4. Energy Harvested from Internal Thermal Energy

This category of prior art includes methods and devices that harvest energy from thermal energy within the human body. Generally these devices use an energy differential to generate electricity. Devices in this category are generally intended to power implanted medical devices.

Examples of methods and devices in the prior art that appear to involve harvesting energy from internal thermal energy include the following: U.S. Pat. No. 6,131,581 (Leysieffer et al. 2000, "Process and Device for Supply of an at Least Partially Implanted Active Device with Electric Power"); U.S. Pat. No. 6,470,212 (Weijand et al. 2002, "Body Heat Powered Implantable Medical Device"); U.S. Pat. No. 6,640,137 (MacDonald 2003, "Biothermal Power Source for Implantable Devices"); U.S. Pat. No. 7,127,293 (MacDonald 2006, "Biothermal Power Source for Implantable Devices"); U.S. Pat. No. 7,340,304 (MacDonald 2008, "Biothermal Power Source for Implantable Devices"); U.S. Pat. No. 8,003,879 (Erbstoeszer et al. 2011, "Method and Apparatus for In Vivo Thermoelectric Power System"); and U.S. Pat. No. 8,039,727 (Erbstoeszer et al. 2011, "Method and Apparatus for Shunt for In Vivo Thermoelectric Power System"); and U.S. Patent Applications 20040093041 (MacDonald 2004, "Biothermal Power Source for Implantable Devices"); 20050171580 (MacDonald 2005, "Biothermal Power Source for Implantable Devices"); 20070251244 (Erbstoeszer et al. 2007, "Method and Apparatus for In Vivo Thermoelectric Power System"); 20070253227 (James et al. 2007, "Power Converter for Use with Implantable Thermoelectric Generator"); and 20100114142 (Albrecht et al. 2010, "Powering Implantable Distension Systems Using Internal Energy Harvesting Means").

5. Energy Harvested from External Pressurized Gas

This category of prior art includes methods, devices, and systems that harvest energy from external pressurized gas that is outside the human body, such as a cylinder of compressed air or some other source of pressurized gas. In an example, a device in this category can use the force of pressurized air from a cylinder, or some other external source of pressurized gas, to power the operation of a blower for a mask. There are few devices in this category in the prior art. The few examples that were found appear to be primarily directed toward creating a portable ventilation system driven by a canister of pressurized gas.

Examples of methods and devices in the prior art that appear to be best classified in this category include the following: U.S. Pat. No. 5,553,454 (Mortner 1996, "Compressed Air Engine System and Method for Generating Electrical Energy from the Controlled Release of Compressed Air"); U.S. Pat. No. 5,969,429 (Rudolph et al. 1999, "Breathing Apparatus Having Electrical Power Supply Arrangement with Turbine-Generator Assembly"); and U.S. Pat. No. 7,218,009 (Hendrickson et al. 2007, "Devices, Systems and Methods for Generating Electricity from Gases Stored in Containers Under Pressure"); and U.S. Patent Applications 20100163046 (Fisher et al. 2010, "Method and Apparatus for Ventilation Assistance"); and 20100199985 (Hamilton et al. 2010, "Portable Gas Powered Positive Pressure Breathing Apparatus and Method").

6. Air Pump/Blower: Wearable

This category of prior art includes methods, devices, and systems that feature an active energy-powered air-moving member (such as an electric air pump or blower) that is integrated into a member (such as a mask or vest) that is worn on the human body. Integration of an active energy-powered air-moving member into a mask, or other member that can be worn, helps to make a system of respiratory support more portable. Also, such a system does not require a tube connected to a separate air-moving member. For the purposes of this review, this category is viewed broadly. Masks have been included that serve various purposes, not just those that provide positive airway pressure for Obstructive Sleep Apnea (OSA). Masks have also been included that serve other functions such as air filtration (including gas masks), gas channeling, and respiratory ventilation.

Examples of methods and devices in the prior art that appear to include an active energy-powered air-moving member in a mask, or other member, that is worn on the human body include the following: U.S. Pat. No. 4,233,972 (Hauff et al. 1980, "Portable Air Filtering and Breathing Assist Device"); U.S. Pat. No. 4,549,542 (Chien 1985, "Multiple-Effect Respirator"); U.S. Pat. No. 4,886,056 (Simpson 1989, "Breathing Apparatus"); U.S. Pat. No. 4,944,310 (Sullivan 1990, "Device for Treating Snoring Sickness"); U.S. Pat. No. 5,035,239 (Edwards 1991, "Powered Respirators"); U.S. Pat. No. 5,303,701 (Heins et al. 1994, "Blower-Supported Gas Mask And Breathing Equipment With An Attachable Control Part"); U.S. Pat. No. 5,372,130 (Stern et al. 1994, "Face Mask Assembly and Method Having a Fan and Replaceable Filter"); U.S. Pat. No. 6,257,235 (Bowen 2001, "Face Mask with Fan Attachment"); U.S. Pat. No. 6,371,112 (Bibi 2002, "Device, System and Method for Preventing Collapse of the Upper Airway"); U.S. Pat. No. 6,435,184 (Ho 2002, "Gas Mask Structure"); U.S. Pat. No. 6,595,212 (Arnott 2003, "Method and Apparatus for Maintaining Airway Patency"); U.S. Pat. No. 6,629,529 (Arnott 2003, "Method for Maintaining Airway Patency"); U.S. Pat. No. 6,705,314 (O'Dea 2004, "Apparatus and Method for Relieving Dyspnoea"); U.S. Pat. No. 6,763,828 (Arnott 2004, "Apparatus for Maintaining Airway Patency"); U.S. Pat. No. 6,854,464 (Mukaiyama et al. 2005, "Respiration Protecting Apparatus"); U.S. Pat. No. 6,895,959 (Lukas 2005, "Gas Mask and Breathing Equipment with a Compressor"); U.S. Pat. No. 6,895,962 (Kullik et al. 2005, "Device for Supporting Respiration"); U.S. Pat. No. 7,195,014 (Hoffman 2007, "Portable Continuous Positive Airway Pressure System"); U.S. Pat. No. 7,195,015 (Kuriyama 2007, "Breathing Apparatus"); U.S. Pat. No. 7,464,705 (Tanizawa et al. 2008, "Powered Respirator"); U.S. Pat. No. 7,516,743 (Hoffman 2009, "Continuous Positive Airway Pressure Device and Configuration For Employing Same"); U.S. Pat. No. 7,823,590 (Bibi et al. 2010, "Devices for Preventing Collapse of the Upper Airway Methods for Use Thereof and Systems and Articles of Manufacture Including Same"); U.S. Pat. No. 7,874,290 (Chalvignac 2011, "Breathing Assistance Device"); U.S. Pat. No. 7,913,692 (Kwok 2011, "CPAP Mask and System"); U.S. Pat. No. 8,020,556 (Hayek 2011, "Respiratory Apparatus"); U.S. Pat. No. 8,020,557 (Bordewick et al. 2011, "Apparatus and Methods for Administration of Positive Airway Pressure Therapies"); and U.S. Pat. No. 8,069,853 (Tilley 2011, "Breath Responsive Powered Air-Purifying Respirator").

Examples of prior art in this category also include: U.S. Patent Applications 20020104541 (Bibi et al. 2002, "Devices, Systems and Methods for Preventing Collapse of the Upper Airway and Sensors for Use Therein"); 20030066527 (Chen 2003, "Face Mask Having Device For Drawing Air Into The Mask"); 20030172930 (Kullik et al. 2003, "Device For Supporting Respiration"); 20040079373 (Mukaiyama et al. 2004, "Respiration Protecting Apparatus"); 20040168689 (Kuriyama 2004, "Respirator"); 20040216741 (Arnott 2004, "Apparatus for Maintaining Airway Patency"); 20040237965 (Bibi et al. 2004, "Devices for Preventing Collapse of the Upper Airway Methods for Use Thereof and Systems and Articles of Manufacture Including Same"); 20050034724 (O'Dea 2005, "Apparatus and Method for Relieving Dyspnoea"); 20060096596 (Occhialini et al. 2006, "Wearable System for Positive Airway Pressure Therapy"); 20060213516 (Hoffman 2006, "Portable Continuous Positive Airway Pressure System"); 20060237013 (Kwok 2006, "Ventilator Mask and System"); 20070000493 (Cox 2007, "Apparatus for Maintaining Airway Patency"); 20070246045 (Hoffman 2007, "Continuous Positive Airway Pressure Device and Configuration For Employing Same"); 20070251527 (Sleeper 2007, "Self-Contained Respiratory Therapy Apparatus for Enhanced Patient Compliance"); 20070277827 (Bordewick et al. 2007, "Apparatus and Methods for Administration of Positive Airway Pressure Therapies"); 20080029098 (Ottestad 2008, "Portable Breathing Apparatus"); 20080178879 (Roberts et al. 2008, "Impeller for a Wearable Positive Airway Pressure Device"); 20080216831 (McGinnis et al. 2008, "Standalone CPAP Device and Method of Using"); 20080216835 (McGinnis et al. 2008, "Standalone CPAP Device and Method of Using"); 20080251079 (Richey 2008, "Apparatus and Method for Providing Positive Airway Pressure"); 20100108070 (Kwok 2010, "Ventilator Mask and System"); 20100163043 (Hart et al. 2010, "Self-Contained Oral Ventilation Device"); and 20100170513 (Bowditch et al. 2010, "Self-Contained, Intermittent Positive Airway Pressure Systems and Methods for Treating Sleep Apnea, Snoring, and Other Respiratory Disorders").

7. Air Pump/Blower: Portable, but not Wearable

This category of prior art includes methods, devices, and systems that have an active energy-powered air-moving member (such as an air pump or blower) that is relatively portable, but wherein the air-moving member does not appear to be integrated into a mask, or other member, that is worn on the human body as was the case in the previous category. Methods and devices in this category generally include a separate air-moving member that is connected, via an air tube, to a mask or other member that is worn on the human body. For example, the air pump or blower may be a bedside unit. The boundary of this category is relatively imprecise because almost all positive airway pressure devices are portable to some extent. For the purposes of this review, we have included only those devices in the prior art that appear to be specifically designed to be portable with features such as: being battery-powered, being energy efficient, being lightweight, and/or being compact.

Examples of methods and devices in the prior art that appear to have an air pump or blower that is portable, but not wearable, include the following: U.S. Pat. No. 6,526,970 (DeVries et al. 2003, "Portable Drag Compressor Powered Mechanical Ventilator"); U.S. Pat. No. 6,877,511 (DeVries et al. 2005, "Portable Drag Compressor Powered Mechanical Ventilator"); U.S. Pat. No. 7,032,589 (Kerechanin et al. 2006, "Portable Ventilator"); U.S. Pat. No. 7,080,646 (Wiesmann et al. 2006, "Self-Contained Micromechanical Ventilator"); U.S. Pat. No. 7,188,621 (DeVries et al. 2007, "Portable Ventilator System"); U.S. Pat. No. 7,222,623 (DeVries et al. 2007, "Portable Drag Compressor Powered Mechanical Ventilator"); U.S. Pat. No. 7,320,321 (Pranger et al. 2008, "Self-Contained Micromechanical Ventilator"); U.S. Pat. No. 7,721,736 (Urias et al. 2010, "Self-Contained Micromechanical Ventilator"); U.S. Pat. No. 7,849,854 (DeVries et al. 2010, "Portable Drag Compressor Powered Mechanical Ventilator"); U.S. Pat. No. 7,866,944 (Kenyon et al. 2011, "Compact Low Noise Efficient Blower for CPAP Devices"); U.S. Pat. No. 7,942,380 (Bertinetti et al. 2011, "Portable Positive Airway Pressure Device Accessories and Methods for Use Thereof"); and U.S. Pat. No. 8,011,362 (Adams 2011, "Compact Continuous Positive Airway Pressure Apparatus and Method"); and U.S. Patent Applications 20080053438 (DeVries et al. 2008, "Portable Ventilator System"); 20080196720 (Kollmeyer et al. 2008, "Mobile Medical Ventilator"); 20100132708 (Martin et al. 2010, "Positive Airway Pressure Device"); 20100307487 (Dunsmore et al. 2010, "Respiratory Therapy Device and Method"); 20110203587 (Bertinetti et al. 2011, "Portable Positive Airway Pressure Device Accessories and Methods for Use Thereof"); 20110203592 (Adams 2011, "Compact Continuous Positive Airway Pressure Apparatus and Method"); and 20110214673 (Masionis 2011, "Portable Life Support Apparatus Ventilator").

8. Air Pump/Blower: Sensor Interactive and Variable Pressure

This category of prior art includes methods, devices, and systems that use an active energy-powered air-moving member to provide respiratory support in an interactive and sophisticated manner that is based on a person's natural respiratory cycle or the occurrence (or prediction) of an adverse respiratory event. For example, positive airway pressure devices in this category can vary the amount of positive airway pressure over time, in an interactive manner, in synchronization with a person's natural breathing cycle. In other examples, a device in this category may increase the amount of pressure, in an interactive manner, in response to airway closure that is detected by a respiratory sensor or is predicted by an algorithm. This category is potentially very broad. For the purposes of this review, we have sought to include only those methods, devices, and systems in the prior art that appear to be most relevant to the present invention, such as those that provide Positive End Expiratory Pressure (PEEP) for Obstructive Sleep Apnea (OSA).

Examples of methods, devices, and systems in the prior art that appear to use an active energy-powered air-moving member to provide respiratory support in an interactive and sophisticated manner include the following: U.S. Pat. No. 4,506,666 (Durkan 1985, "Method and Apparatus for Rectifying Obstructive Apnea"); U.S. Pat. No. 4,823,788 (Smith et al. 1989, "Demand Oxygen Controller and Respiratory Monitor"); U.S. Pat. No. 5,134,995 (Gruenke et al. 1992, "Inspiratory Airway Pressure System with Admittance Determining Apparatus and Method"); U.S. Pat. No. 5,148,802 (Sanders et al. 1992, "Method and Apparatus for Maintaining Airway Patency to Treat Sleep Apnea and Other Disorders"); U.S. Pat. No. 5,199,424 (Sullivan et al. 1993, "Device for Monitoring Breathing During Sleep and Control of CPAP Treatment that is Patient Controlled"); U.S. Pat. No. 5,203,343 (Axe et al. 1993, "Method and Apparatus for Controlling Sleep Disorder Breathing"); U.S. Pat. No. 5,239,995 (Estes et al. 1993, "Sleep Apnea Treatment Apparatus"); U.S. Pat. No. 5,245,995 (Sullivan et al. 1993, "Device and Method for Monitoring Breathing During Sleep, Control of CPAP Treatment, and Preventing of Apnea"); U.S. Pat. No. 5,259,373 (Gruenke et al. 1993, "Inspiratory Airway Pressure System Controlled by the Detection and Analysis of Patient Airway Sounds"); U.S. Pat. No. 5,301,689 (Wennerholm 1994, "Device for Temporary Artificial Respiration Assistance for Persons Having Snore Problems"); U.S. Pat. No. 5,535,738 (Estes et al. 1996, "Method and Apparatus for Providing Proportional Positive Airway Pressure to Treat Sleep Disordered Breathing"); U.S. Pat. No. 5,645,054 (Cotner et al. 1997, "Device and Method for the Treatment of Sleep Apnea Syndrome"); U.S. Pat. No. 5,649,533 (Oren 1997, "Therapeutic Respiration Device"); U.S. Pat. No. 5,664,562 (Bourdon 1997, "Breathing Aid Device"); U.S. Pat. No. 5,845,636 (Gruenke et al. 1998, "Method and Apparatus for Maintaining Patient Airway Patency"); U.S. Pat. No. 5,868,133 (DeVries et al. 1999, "Portable Drag Compressor Powered Mechanical Ventilator"); U.S. Pat. No. 5,884,625 (Hart 1999, "Oral Appliance for Delivering Gas to the Retroglossal Area"); U.S. Pat. No. 5,918,597 (Jones et al. 1999, "PEEP Control in a Piston Ventilator"); U.S. Pat. No. 5,950,624 (Hart 1999, "Oral Appliance Having Hollow Body"); U.S. Pat. No. 5,953,713 (Behbehani et al. 1999, "Method and Apparatus for Treatment of Sleep Disorder Breathing Employing Artificial Neural Network"); and U.S. Pat. No. 6,085,747 (Axe et al. 2000, "Method and Apparatus for Controlling Sleep Disorder Breathing").

Examples of prior art in this category also include: U.S. Pat. No. 6,253,764 (Calluaud 2001, "Control of Delivery Pressure in CPAP Treatment or Assisted Respiration"); U.S. Pat. No. 6,283,119 (Bourdon 2001, "Breathing Aid Apparatus in Particular for Treating Sleep Apnoea"); U.S. Pat. No. 6,349,724 (Burton et al. 2002, "Dual-Pressure Blower for Positive Air Pressure Device"); U.S. Pat. No. 6,427,689 (Estes et al. 2002, "Sleep Apnea Treatment Apparatus"); U.S. Pat. No. 6,484,719 (Berthon-Jones 2002, "Method for Providing Ventilatory Assistance in a Spontaneously Breathing Subject"); U.S. Pat. No. 6,532,957 (Berthon-Jones 2003, "Assisted Ventilation to Match Patient Respiratory Need"); U.S. Pat. No. 6,629,527 (Estes et al. 2003, "Sleep Apnea Treatment Apparatus"); U.S. Pat. No. 6,810,876 (Berthon-Jones 2004, "Assisted Ventilation to Match Patient Respiratory Need"); U.S. Pat. No. 6,895,964 (McAuliffe et al. 2005, "Flow Diverter for Controlling the Pressure and Flow Rate in CPAP Device"); U.S. Pat. No. 6,948,497 (Zdrojkowski et al. 2005, "Breathing Gas Delivery Method and Apparatus"); U.S. Pat. No. 6,988,994 (Rapoport et al. 2006, "Positive Airway Pressure System and Method for Treatment of Sleeping Disorder in Patient"); U.S. Pat. No. 6,990,980 (Richey 2006, "Carbon Dioxide-Based Bi-Level CPAP Control"); U.S. Pat. No. 7,036,506 (McAuliffe et al. 2006, "Flow Diverter for Controlling the Pressure and Flow Rate in CPAP Device"); U.S. Pat. No. 7,044,129 (Truschel et al. 2006, "Pressure Support System and Method"); U.S. Pat. No. 7,100,607 (Zdrojkowski et al. 2006, "Breathing Gas Delivery Method and Apparatus"); U.S. Pat. No. 7,128,069 (Farrugia et al. 2006, "Method and Apparatus for Improving the Comfort of CPAP"); U.S. Pat. No. 7,152,598 (Morris et al. 2006, "System and Method for Providing a Breathing Gas"); U.S. Pat. No. 7,246,619 (Truschel et al. 2007, "Snore Detecting Method and Apparatus"); U.S. Pat. No. 7,284,554 (Shaw 2007, "Continuous Positive Airway Pressure Device"); U.S. Pat. No. 7,370,650 (Nadjafizadeh et al. 2008, "Gas Supply Device for Sleep Apnea"); and U.S. Pat. No. 7,448,383 (Delache et al. 2008, "Air Assistance Apparatus Providing Fast Rise And Fall Of Pressure Within One Patient's Breath").

Examples of prior art in this category further include: U.S. Pat. No. 7,469,697 (Lee et al. 2008, "Feedback System and Method for Sleep Disordered Breathing Therapy"); U.S. Pat. No. 7,527,055 (McAuliffe et al. 2009, "Flow Diverter for Controlling the Pressure and Flow Rate in CPAP Device"); U.S. Pat. No. 7,533,670 (Freitag et al. 2009, "Systems, Methods and Apparatus for Respiratory Support of a Patient"); U.S. Pat. No. 7,562,657 (Blanch et al. 2009, "Method And Apparatus For Non-Invasive Prediction of Intrinsic Positive End-Expiratory Pressure (PEEPi) in Patients Receiving Ventilator Support"); U.S. Pat. No. 7,575,005 (Mumford et al. 2009, "Mask Assembly with Integrated Sensors"); U.S. Pat. No. 7,694,679 (McAuliffe et al. 2010, "Flow Diverter for Controlling the Pressure and Flow Rate in CPAP Device"); U.S. Pat. No. 7,793,660 (Kimmel et al. 2010, "Method of Treating Obstructive Sleep Apnea"); U.S. Pat. No. 7,841,343 (Deane et al. 2010, "Systems and Methods for Delivering Therapeutic Gas to Patients"); U.S. Pat. No. 7,866,318 (Bassin 2011, "Methods For Providing Expiratory Pressure Relief In Positive Airway Pressure Therapy"); U.S. Pat. No. 7,901,361 (Rapoport et al. 2011, "Method and Apparatus for Optimizing the Continuous Positive Airway Pressure for Treating Obstructive Sleep Apnea"); U.S. Pat. No. 7,942,824 (Kayyali et al. 2011, "Integrated Sleep Diagnostic and Therapeutic System and Method"); U.S. Pat. No. 8,011,365 (Douglas et al. 2011, "Mechanical Ventilation in the Presence of Sleep Disordered Breathing"); U.S. Pat. No. 8,015,974 (Christopher et al. 2011, "System for Providing Flow-Targeted Ventilation Synchronized to a Patient's Breathing Cycle"); U.S. Pat. No. 8,020,558 (Christopher et al. 2011, "System for Providing Flow-Targeted Ventilation Synchronized to a Patient's Breathing Cycle"); U.S. Pat. No. 8,051,853 (Berthon-Jones 2011, "Method and Apparatus for Providing Ventilatory Assistance"); and U.S. Pat. No. 8,068,904 (Sun et al. 2011, "Devices and Methods for Monitoring Physiological Information Relating to Sleep with an Implantable Device").

Examples of prior art in this category further include: U.S. Patent Applications 20070215156 (Kwok 2007, "Snoring Treatment Apparatus and Methods of Managing Snorers"); 20080142013 (Hallett et al. 2008, "Exhaust Apparatus for Use in Administering Positive Pressure Therapy Through the Nose or Mouth"); 20090020121 (Bassin 2009, "Methods for Providing Expiratory Pressure Relief in Positive Airway Pressure Therapy"); 20100180895 (Kwok et al. 2010, "Methods and Apparatus for Controlling Mask Leak in CPAP Treatment"); 20100252042 (Kapust et al. 2010, "Methods, Systems and Devices for Non-Invasive Open Ventilation for Treating Airway Obstructions"); 20100269834 (Freitag et al. 2010, "Systems, Methods and Apparatus for Respiratory Support of a Patient"); 20100313898 (Richard et al. 2010, "Apparatus and Methods for Treating Sleep Related Disorders"); 20110073110 (Kenyon et al. 2011, "Compact Low Noise Efficient Blower for CPAP Devices"); 20110079224 (Arnott 2011, "System, Apparatus and Method for Maintaining Airway Patency and Pressure Support Ventilation"); 20110284003 (Douglas et al. 2011, "Mechanical Ventilation in the Presence of Sleep Disordered Breathing"); and 20110295083 (Doelling et al. 2011, "Devices, Systems, and Methods for Monitoring, Analyzing, and/or Adjusting Sleep Conditions").

9. Passive Exhalation Resistance Device

This category of prior art includes methods, devices, and systems that provide passive resistance to exhalation. They do not use an active energy-powered air-moving member such as an air pump or blower. Passive resistance to exhalation can be used to provide Positive End Expiratory Pressure (PEEP) for respiratory conditions such as Obstructive Sleep Apnea (OSA). This category includes devices that are integrated into a member (such as a mask, nasal insert, or mouth appliance) that is attached to the human body and/or covers a person's nasal and/or oral openings. Some such devices have an airflow valve that offers greater resistance to gas outflow, during exhalation, and less resistance to gas inflow, during inhalation.

Devices in this category are more portable than devices to provide positive airway pressure that require a connection to an external power source. Over time, devices in this category are also more portable than battery-powered positive airway pressure devices because the batteries of the latter devices must be repeatedly recharged. Other potential advantages of devices in this category include their simplicity of operation, reduced noise compared to energy-powered blowers, and the freedom of movement that they offer to people who would otherwise be tethered to an air tube while sleeping. One could argue that handheld devices that can be held against a person's face in order to cover nasal and/or oral openings should not be included here because they are not helpful for providing respiratory support while a person sleeps. However, in this review, handheld devices are included in this category for the sake of completeness.

Examples of methods and devices in the prior art that appear to provide respiratory support through passive resistance to exhalation include the following: U.S. Pat. No. 746,869 (Moulton 1903, "Device for Preventing Snoring"); U.S. Pat. No. 3,908,987 (Boehringer 1975, "Controlled Positive End Pressure Expiratory Device"); U.S. Pat. No. 5,018,517 (Liardet 1991, "Expiration-Resisting Apparatus Designed for Improving Pulmonary Ventilation"); U.S. Pat. No. 5,658,221 (Hougen 1997, "Portable Personal Breathing Apparatus and Method of Using Same"); U.S. Pat. No. 5,890,998 (Hougen 1999, "Portable Personal Breathing Apparatus"); U.S. Pat. No. 6,425,393 (Lurie et al. 2002, "Automatic Variable Positive Expiratory Pressure Valve And Methods"); U.S. Pat. No. 6,510,846 (O'Rourke 2003, "Sealed Back Pressure Breathing Device"); U.S. Pat. No. 6,581,598 (Foran et al. 2003, "Positive Expiratory Pressure Device"); U.S. Pat. No. 6,659,100 (O'Rourke 2003, "Sealed Back Pressure Breathing Device"); U.S. Pat. No. 6,722,360 (Doshi 2004, "Methods and Devices for Improving Breathing in Patients with Pulmonary Disease"); U.S. Pat. No. 6,786,216 (O'Rourke 2004, "Sealed Back Pressure Breathing Device"); U.S. Pat. No. 6,883,518 (Mittelstadt et al. 2005, "Unidirectional Respirator Valve"); U.S. Pat. No. 6,997,177 (Wood 2006, "Ventilation Interface for Sleep Apnea Therapy"); U.S. Pat. No. 7,059,324 (Pelerossi et al. 2006, "Positive Expiratory Pressure Device with Bypass"); U.S. Pat. No. 7,334,581 (Doshi 2008, "Methods and Devices for Improving Breathing in Patients with Pulmonary Disease"); U.S. Pat. No. 7,506,649 (Doshi et al. 2009, "Nasal Devices"); U.S. Pat. No. 7,699,054 (Pelerossi et al. 2010, "Positive Expiratory Pressure Device"); U.S. Pat. No. 7,735,491 (Doshi et al. 2010, "Methods of Treating Respiratory Disorders"); U.S. Pat. No. 7,735,492 (Doshi et al. 2010, "Nasal Respiratory Devices"); U.S. Pat. No. 7,779,841 (Dunsmore et al. 2010, "Respiratory Therapy Device and Method"); U.S. Pat. No. 7,798,148 (Doshi et al. 2010, "Respiratory Devices"); U.S. Pat. No. 7,806,120 (Loomas et al. 2010, "Nasal Respiratory Devices for Positive End-Expiratory Pressure"); U.S. Pat. No. 7,856,979 (Doshi et al. 2010, "Nasal Respiratory Devices"); U.S. Pat. No. 7,987,852 (Doshi et al. 2011, "Nasal Devices"); U.S. Pat. No. 7,992,563 (Doshi 2011, "Methods and Devices for Improving Breathing in Patients with Pulmonary Disease"); U.S. Pat. No. 7,992,564 (Doshi et al. 2011, "Respiratory Devices"); U.S. Pat. No. 8,020,700 (Doshi et al. 2011, "Packaging and Dispensing Nasal Devices"); U.S. Pat. No. 8,025,054 (Dunsmore et al. 2011, "Passive Respiratory Therapy Device"); and U.S. Pat. No. 8,061,357 (Pierce et al. 2011, "Adhesive Nasal Respiratory Devices").

Examples of prior art in this category also include: U.S. Patent Applications 20060144398 (Doshi et al. 2006, "Respiratory Devices"); 20060150978 (Doshi et al. 2006, "Methods of Treating Respiratory Disorders"); 20060150979 (Doshi et al. 2006, "Nasal Respiratory Devices"); 20070277832 (Doshi et al. 2007, "Nasal Respiratory Devices"); 20070283962 (Doshi et al. 2007, "Layered Nasal Devices"); 20070295338 (Loomas et al. 2007, "Nasal Respiratory Devices For Positive End-Expiratory Pressure"); 20080041373 (Doshi et al. 2008, "Nasal Devices"); 20080173309 (Doshi 2008, "Methods and Devices for Improving Breathing in Patients with Pulmonary Disease"); 20080178874 (Doshi et al. 2008, "Adjustable Nasal Devices"); 20090050144 (Pierce et al. 2009, "Adhesive Nasal Respiratory Devices"); 20090145441 (Doshi et al. 2009, "Delayed Resistance Nasal Devices and Methods of Use"); 20090188493 (Doshi et al. 2009, "Nasal Devices"); 20090194100 (Minagi 2009, "Nostril Plug for Improving Articulatory Disorder"); 20090194109 (Doshi et al. 2009, "CPAP Interface and Backup Devices"); 20090241965 (Sather et al. 2009, "Nasal Devices with Noise-Reduction and Methods of Use"); 20090308398 (Ferdinand et al. 2009, "Adjustable Resistance Nasal Devices"); 20100326447 (Loomas et al. 2010, "Nasal Respiratory Devices for Positive End-Expiratory Pressure"); 20100331877 (Li et al. 2010, "Airflow Restriction System"); 20110005520 (Doshi et al. 2011, "Quiet Nasal Respiratory Devices"); 20110005529 (Doshi et al. 2011, "Methods of Treating a Sleeping Subject"); 20110005530 (Doshi et al. 2011, "Methods of Treating a Disorder by Inhibiting Expiration"); 20110056499 (Doshi et al. 2011, "Sealing Nasal Devices for Use While Sleeping"); 20110067708 (Doshi et al. 2011, "Nasal Devices for Use While Sleeping"); 20110067709 (Doshi et al. 2011, "Nasal Respiratory Devices"); 20110203598 (Favet et al. 2011, "Nasal Devices Including Layered Nasal Devices and Delayed Resistance Adapters for Use with Nasal Devices"); 20110218451 (Lai et al. 2011, "Nasal Devices, Systems and Methods"); 20110220123 (Robson 2011, "Anti-Snoring Device Using Naturally Generated Positive Pressure"); 20110240038 (Doshi et al. 2011, "Nasal Devices"); and 20110290256 (Sather et al. 2011, "Layered Nasal Respiratory Devices").

10. Tongue Engaging Device: Suction/Friction

This category of prior art includes methods, devices, and systems that engage the exterior surface of the tongue in order to draw it forward and keep it from blocking the airway. Such devices can be useful when the tongue would otherwise slide backwards and block the airway during sleep. This can be one cause of Obstructive Sleep Apena (OSA). Some of the methods and devices in this category involve engaging the exterior of the tongue using suction. For example, some devices are mouth appliances with suction tubes that engage the tongue. Other methods and devices in this category involve engaging the exterior of the tongue through other means such as clamps, elastic bands, or even peristaltic motion.

Examples of methods and devices in the prior art that appear to engage the exterior of the tongue to draw it forward and keep it out of the airway include the following: U.S. Pat. No. 5,957,133 (Hart 1999, "Oral Appliance with Negative Air Supply for Reducing Sleep Apnea and Snoring"); U.S. Pat. No. 6,055,986 (Meade 2000, "Apparatus and Method for the Reduction of Snoring"); U.S. Pat. No. 6,494,209 (Kulick 2002, "Method and Apparatus for Treatment of Snoring, Hypopnea and Apnea"); U.S. Pat. No. 6,877,513 (Scarberry et al. 2005, "Intraoral Apparatus for Enhancing Airway Patency"); U.S. Pat. No. 7,954,494 (Connor 2011, "Device with Actively-Moving Members that Hold or Move the Tongue"); U.S. Pat. No. 8,028,705 (Li 2011, "Tongue Retention System"); and U.S. Pat. No. 8,074,656 (Vaska et al. 2011, "Methods and Systems for Creating Pressure Gradients to Improve Airway Patency"); and U.S. Patent Applications 20090120446 (Vaska et al. 2009, "Methods and Systems for Improving Airway Patency"); 20100139668 (Harrington 2010, "Method and Device for Treatment of Obstructive Sleep Apnea"); 20110073119 (Chen et al. 2011, "Negative Pressure Oral Apparatus"); 20110180075 (Chen et al. 2011, "Adjustable Oral Interface and Method to Maintain Upper Airway Patency"); 20110180076 (Hegde et al. 2011, "Wearable Tissue Retention Device"); 20110192404 (Chen 2011, "Automated Negative Pressure Oral Apparatus"); 20110220124 (Vaska et al. 2011, "Methods and Systems for Improving Airway Patency"); and 20110259346 (Tsuiki et al. 2011, "Tongue Position Controller").

11. Tongue Engaging Device: Implant/Anchor

This category of prior art includes methods, devices, and systems that involve implanting tongue-restraining or tongue-moving members inside the tongue in order to keep it, or move it, forward and out of the airway. Such implants can useful when the tongue would otherwise slide backwards and block the airway during sleep in Obstructive Sleep Apnea (OSA). Some of these methods and devices involve implantation of a tissue anchor in the posterior portion of the tongue and then connecting this anchor to an anterior structure such as the jaw bone or a dental appliance. The tissue anchor pulls the tongue forward. Other methods and devices in this category involve implantation of magnets in the tongue. These magnets, when engaged by a magnetic field, move the tongue forward by magnetic attraction or repulsion.

Examples of methods and devices in the prior art that appear to involve implants within the tongue to pull the tongue forward include the following: U.S. Pat. No. 7,644,714 (Atkinson et al. 2010, "Devices and Methods for Treating Sleep Disorders"); U.S. Pat. No. 7,658,192 (Harrington 2010, "Method and Device for Treatment of Obstructive Sleep Apnea"); U.S. Pat. No. 7,909,038 (Hegde et al. 2011, "Tongue Stabilization Device and Methods of Using the Same"); U.S. Pat. No. 7,921,850 (Nelson et al. 2011, "Systems and Methods for Moving and/or Restraining Tissue in the Upper Respiratory System"); U.S. Pat. No. 7,934,506 (Woodson et al. 2011, "System and Method for Temporary Tongue Suspension"); U.S. Pat. No. 7,975,700 (Frazier et al. 2011, "System for Adjustable Tissue Anchors"); U.S. Pat. No. 8,047,206 (Boucher et al. 2011, "Magnetic Devices, Systems, and Methods Placed In or On a Tongue"); and U.S. Pat. No. 8,074,655 (Sanders 2011, "Methods and Devices for Treating Sleep Apnea and Snoring"); and U.S. Patent Applications 20080060660 (Nelson et al. 2008, "Systems and Methods for Moving and/or Restraining Tissue in the Upper Respiratory System"); 20100132719 (Jacobs et al. 2010, "Implant Systems and Methods for Treating Obstructive Sleep Apnea"); 20100137905 (Weadock et al. 2010, "Implant Systems and Methods for Treating Obstructive Sleep Apnea"); 20110166598 (Gonazles et al. 2011, "Devices and Methods for Tongue Stabilization"); 20110308529 (Gillis et al. 2011, "Systems and Methods for Treatment of Sleep Apnea"); and 20110308530 (Gillis et al. 2011, "Systems and Methods for Treatment of Sleep Apnea").

12. Tongue Engaging Device: Nerve Stimulation

This category of prior art includes methods, devices, and systems that use electrical impulses to stimulate nerves that innervate the muscles that control movement of the tongue or other soft tissue along the airway. Stimulation of these nerves causes the tongue, or other soft tissue, to move out of the airway. For example, some methods and devices in this category involve stimulation of the HypoGlossal Nerve (HGN) that controls the tongue and soft palate muscles. Generally, although not always, the device that provides nerve stimulation is implanted within the body in a manner similar to the way in which a pacemaker is implanted. This can be a useful approach for treating Obstructive Sleep Apnea (OSA).

Examples of methods and devices in the prior art that appear to involve stimulation of nerves to move the tongue or other soft tissue out of the airway include include the following: U.S. Pat. No. 5,123,425 (Shannon et al. 1992, "Obstructive Sleep Apnea Collar"); U.S. Pat. No. 7,025,730 (Cho et al. 2006, "System and Method for Automatically Monitoring and Delivering Therapy for Sleep-Related Disordered Breathing"); U.S. Pat. No. 7,809,442 (Bolea et al. 2010, "Obstructive Sleep Apnea Treatment Devices, Systems and Methods"); U.S. Pat. No. 7,937,159 (Lima et al. 2011, "Apparatus, System and Method for Therapeutic Treatment of Obstructive Sleep Apnea"); and U.S. Pat. No. 8,024,044 (Kirby et al. 2011, "Method and Apparatus for Hypoglossal Nerve Stimulation"); and U.S. Patent Applications 20070173893 (Pitts 2007, "Method and Apparatus for Preventing Obstructive Sleep Apnea"); 20080109047 (Pless 2008, "Apnea Treatment Device"); 20100121406 (Libbus et al. 2010, "Neural Stimulator to Treat Sleep Disordered Breathing"); 20100198306 (Lima et al. 2010, "Apparatus, System and Method for Therapeutic Treatment of Obstructive Sleep Apnea"); 20110071591 (Bolea et al. 2011, "Obstructive Sleep Apnea Treatment Devices, Systems and Methods"); 20110112601 (Meadows et al. 2011, "System for Stimulating a Hypoglossal Nerve for Controlling the Position of a Patient's Tongue"); 20110152966 (Bolea et al. 2011, "Obstructive Sleep Apnea Treatment Devices, Systems and Methods"); 20110196445 (Bolea et al. 2011, "Obstructive Sleep Apnea Treatment Devices, Systems and Methods");

20110202106 (Bolea et al. 2011, "Obstructive Sleep Apnea Treatment Devices, Systems and Methods"); 20110264164 (Christopherson et al. 2011, "Method of Treating Sleep Disordered Breathing"); and 20110301679 (Rezai et al. 2011, "Apparatus and Method for Treating Pulmonary Conditions").

13. Airway Engaging Device: Stent or Magnet

This category of prior art includes methods and devices that involve implanting a tissue-supporting scaffold (such as a stent) or some other implant in the airway in order to physically prop the airway open. One example of devices in this category are stents that are implanted in the tissue surrounding the airway to prop the airway open regardless of the pressure level in the airway. Another example of devices in this category are magnets that are implanted in the tissue surrounding the airway methods. In the case of magnets, electromagnetic repulsion or attraction provides the force to keep the airway open.

Examples of methods and devices in the prior art that appear to involve implantation of stents, magnets, or other members in airway tissue to keep the airway open include the following: U.S. Pat. No. 7,958,895 (Nelson et al. 2011, "Magnetic Force Devices, Systems, and Methods for Resisting Tissue Collapse within the Pharyngeal Conduit"); U.S. Pat. No. 7,958,896 (Nelson et al. 2011, "Magnetic Force Devices, Systems, and Methods for Resisting Tissue Collapse within the Pharyngeal Conduit"); U.S. Pat. No. 7,992,566 (Pflueger et al. 2011, "Apparatus and Methods for Treating Sleep Apnea") and U.S. Pat. No. 7,997,266 (Frazier et al. 2011, "System and Method for Airway Manipulation"); and U.S. Patent Applications 20100280626 (Shalon et al. 2010, "Devices and Methods for Treating Sleep Disordered Breathing"); 20100319711 (Hegde et al. 2010, "Airway Implant and Methods of Making and Using"); and 20110290258 (Pflueger et al. 2011, "Apparatus and Methods for Treating Sleep Apnea").

14. Outward Force on Body Surface

This category of prior art includes methods, devices, and system that seek to keep the airway open by applying outward force on neck tissue or some other portion of the body surface. The intent is to pull soft tissue near the body's exterior outward from the core of the body, which pulls soft tissue near the airway outward, which keeps the airway open. Some methods and devices in this category use negative pressure (such as suction) to engage the exterior surface of the neck, or some other portion of the body exterior, and pull it outwards. Other methods and devices in this category use adhesion to engage the exterior surface of the neck, or some other portion of the body, and draw it outwards. There are relatively few examples of this approach in the prior art.

Examples of methods and devices in the prior art that appear to seek to treat respiratory conditions by exerting outward force on a body surface including the following: U.S. Pat. No. 7,762,263 (Aarestad et al. 2010, "Device and Method for Opening an Airway") and U.S. Pat. No. 7,793,661 (Macken 2010, "Method and Apparatus for Treatment of Snoring and Sleep Apnea"); and U.S. Patent Applications 20030167018 (Wyckoff 2003, "Sleep Apnea Device and Method Thereof"); 20100275910 (Aarestad et al. 2010, "Device and Method for Opening an Airway"); and 20110066086 (Aarestad et al. 2011, "Device and Method for Opening an Airway").

15. Mouth Insert/Appliance

This category of prior art includes methods, devices, and systems that are inserted into the mouth in order to address a respiratory condition such as Obstructive Sleep Apnea (OSA) or snoring. Some of the devices in this category engage the teeth to move the jaw forward. Moving the jaw forward is intended to move the tongue, or other soft tissue, forward and away from the airway. Other methods and devices in this category seek to address respiratory conditions by changing the air pressure in the oral cavity. Other methods and devices in this category are simply designed to keep the mouth closed and prevent airflow through the mouth. There are a few examples of advanced mouth inserts that include an air pump or blower that is integrated into a mouth insert that a person wears. Advanced devices with an active energy-using air moving member that are worn have been included in the "Air Pump/Blower: Wearable" category above (category 6) because such integration is their dominant feature with respect to this review of the prior art.

Examples of methods and devices in the prior art that appear to include a mouth insert or mouth appliance to treat a respiratory condition, without an integrated active air-moving member, include the following: U.S. Pat. No. 5,678,567 (Thornton et al. 1997, "Method and Apparatus for Adjusting a Dental Device"); U.S. Pat. No. 5,826,579 (Remmers et al. 1998, "Remote-Controlled Mandibular Positioning Device and Method of Using the Device"); U.S. Pat. No. 5,921,942 (Remmers et al. 1999, "Adaptively Controlled Mandibular Positioning Device and Method of Using the Device"); U.S. Pat. No. 5,954,048 (Thornton 1999, "Device and Method for Improving Breathing"); U.S. Pat. No. 5,983,892 (Thornton 1999, "Device for Improving Breathing"); U.S. Pat. No. 6,155,262 (Thornton et al. 2000, "Method and Apparatus for Adjusting a Dental Device"); U.S. Pat. No. 6,273,859 (Remmers et al. 2001, "Adaptively Controlled Mandibular Positioning Device and Method of Using the Device"); U.S. Pat. No. 6,305,376 (Thornton 2001, "Device and Method for Improving Breathing"); U.S. Pat. No. 6,374,824 (Thornton 2002, "Device for Improving Breathing"); U.S. Pat. No. 6,405,729 (Thornton 2002, "Oral Appliance for Improving Breathing and Method of Constructing Same"); U.S. Pat. No. 6,845,774 (Gaskell 2005, "Dental Device"); and U.S. Pat. No. 7,650,885 (Paoluccio et al. 2010, "Mouthpiece and Mask for Ventilation Assistance and Connector for Joining Objects"); and U.S. Patent Applications 20050081859 (Scarberry et al. 2005, "Intraoral Apparatus for Enhancing Airway Patency"); 20050236003 (Meader 2005, "Apnea Nipple and Oral Airway and Mandibular Advancement Device"); 20090078273 (Bhat et al. 2009, "Smart Mandibular Repositioning System"); and 20110232652 (Levendowski et al. 2011, "Systems and Methods for Optimizing Oral Appliance Therapy for the Treatment of Sleep Apnea").

16. One-Way Valve in Lung

This category of prior art includes methods, devices, and systems that involve implanting a one-way valve (partial or complete) into an air passage within a lung. Although counter-intuitive in some respects, this approach can help in the treatment of Chronic Obstructive Pulmonary Disease (COPD). The valve serves to isolate a diseased portion of the lung from the good portions of the lung. This can prevent the disease from spreading from the bad sections of the lung to the good sections of the lung. To date, implantation of a one-way valve somewhere along the interior airway does not appear to have been proposed to treat Obstructive Sleep Apnea (OSA), but we include this category in this review for the sake of completeness.

Examples of methods and devices in the prior art that appear to involve implanting a one-way valve into a lung (or elsewhere in the central airway) include the following: U.S. Pat. No. 7,406,963 (Chang et al. 2008, "Variable Resistance Pulmonary Ventilation Bypass Valve and Method"); U.S. Pat. No. 7,686,013 (Chang et al. 2010, "Variable Resistance Pulmonary Ventilation Bypass Valve"); U.S. Pat. No. 7,726,305 (Chang et al. 2010, "Variable Resistance Pulmonary Ventilation Bypass Valve") and U.S. Pat. No. 7,875,048 (Dillard et al. 2011, "One-Way Valve Devices for Anchored Implantation in a Lung").

17. External Response to Sensor

This category of prior art includes methods, devices, and systems that involve external (generally non-therapeutic) responses, such as alarms, to respiratory events. There are exceptions, but these responses are generally not directly therapeutic in themselves. These responses are generally intended to provoke a therapeutic response on the part of a person who hears an alarm. Some methods and devices in this category involve an alarm that sounds in response to an adverse respiratory event. Other methods and devices in this category involve prompting a change in body position in response to an adverse respiratory event. In the latter case, the hope is that prompting a change in body position will help to correct the adverse respiratory event.

Examples of methods and devices in the prior art that appear to involve external (generally non-therapeutic) responses to respiratory events include the following: U.S. Pat. No. 6,371,120 (Chiu et al. 2002, "Snore Elimination Device"); U.S. Pat. No. 6,386,201 (Fard 2002, "Apparatus for Preventing Snoring"); U.S. Pat. No. 7,387,608 (Dunlop et al. 2008, "Apparatus and Method for the Treatment of Sleep Related Disorders"); U.S. Pat. No. 7,716,988 (Ariav et al. 2010, "Apparatus for Use in Controlling Snoring and Sensor Unit Particularly Useful Therein"); U.S. Pat. No. 7,725,195 (Lima et al. 2010, "RFID-Based Apparatus, System, and Method for Therapeutic Treatment of Obstructive Sleep Apnea"); U.S. Pat. No. 7,789,837 (Lehrman et al. 2010, "System and Method for Treating Obstructive Sleep Apnea"); and U.S. Pat. No. 7,866,212 (Ariav et al. 2011, "High-Sensitivity Sensors for Sensing Various Physiological Phenomena, Particularly Useful in Anti-Snoring Apparatus and Methods"); and U.S. Patent Applications 20080221470 (Sather et al. 2008, "Respiratory Sensor Adapters for Nasal Devices") and 20100078017 (Andrieux et al. 2010, "Wireless Communications for a Breathing Assistance System").

18. Other Potentially-Relevant Art

This last category of prior art is a miscellaneous category. This category includes a variety of methods, devices, and systems related to energy harvesting and/or providing respiratory support that are not easy to classify, but may nonetheless be relevant to the present invention. Examples of methods, devices, and systems in the prior art that have been included in this miscellaneous category are as follows: U.S. Pat. No. 3,268,845 (Whitmore 1966, "Respiration and Movement Transducer"); U.S. Pat. No. 3,837,337 (LaViolette 1974, "Self-Contained Closed Circuit Breathing Apparatus"); U.S. Pat. No. 4,821,712 (Gossett 1989, "Breathing Apparatus"); U.S. Pat. No. 5,048,517 (Pasternack 1991, "Recirculating Positive-Pressure Respirator"); U.S. Pat. No. 5,687,715 (Landis et al. 1997, "Nasal Positive Airway Pressure Apparatus and Method"); U.S. Pat. No. 5,810,015 (Flaherty 1998, "Power Supply for Implantable Device"); U.S. Pat. No. 6,302,105 (Wickham et al. 2001, "Apparatus for Supplying Breathable Gas"); U.S. Pat. No. 6,401,714 (Giorgini 2002, "Self Contained Breathing Apparatus"); U.S. Pat. No. 6,411,852 (Danek et al. 2002, "Modification of Airways by Application of Energy"); U.S. Pat. No. 6,457,471 (Bibi 2002, "Dual-Purpose Medical Device for Upper Airway Treatment and Methods for Using Same"); U.S. Pat. No. 6,772,762 (Piesinger 2004, "Personal Powered Air Filtration, Sterilization, and Conditioning System"); U.S. Pat. No. 6,792,942 (Ho et al. 2004, "Sleep Silencer"); U.S. Pat. No. 7,066,177 (Pittaway et al. 2006, "Exhalation Valves"); U.S. Pat. No. 7,080,645 (Genger et al. 2006, "Anti-Snoring Device, Method for Reducing Snoring, and a Nasal Air Cannula"); U.S. Pat. No. 7,114,497 (Aylsworth et al. 2006, "Method and System of Individually Controlling Airway Pressure of a Patient's Nares"); U.S. Pat. No. 7,275,542 (Lurie et al. 2007, "Bag-Valve Resuscitation for Treatment of Hypotension, Head Trauma, and Cardiac Arrest"); U.S. Pat. No. 7,406,966 (Wondka 2008, "Method and Device for Non-Invasive Ventilation with Nasal Interface"); U.S. Pat. No. 7,451,766 (Miller 2008, "Enhanced Breathing Device"); U.S. Pat. No. 7,562,659 (Matarasso 2009, "Respiratory Aid Apparatus and Method"); U.S. Pat. No. 7,835,529 (Hernandez et al. 2010, "Sound Canceling Systems and Methods"); U.S. Pat. No. 7,909,035 (Thornton 2011, "Multi-Chamber Mask and Method of Forming the Same"); U.S. Pat. No. 7,951,357 (Gross et al. 2011, "Implantable Power Sources and Sensors"); U.S. Pat. No. 7,967,014 (Heidmann et al. 2011, "Application Device for Breathing Mask Arrangement"); U.S. Pat. No. 8,037,885 (Metzger et al. 2011, "Treatment for Sleep Apnea or Snoring"); U.S. Pat. No. 8,051,850 (Kwok et al. 2011, "Nasal Dilator"); and U.S. Pat. No. 8,074,647 (Truitt et al. 2011, "Impeller and a Pressure Support System and Method Using Such a Method").

Examples of prior art in this miscellaneous category also include: U.S. Patent Applications 20060180149 (Matarasso 2006, "A Respiratory Aid System and Method"); 20080060649 (Veliss et al. 2008, "Delivery of Respiratory Therapy"); 20080135044 (Freitag et al. 2008, "Methods and Devices for Minimally Invasive Respiratory Support"); 20080142018 (Doshi et al. 2008, "Nasal Device Applicators"); 20090165799 (Duquette et al. 2009, "Continuous Positive Airway Pressure Device"); 20090320842 (Doherty et al. 2009, "Mask and Flow Generator System"); 20100000543 (Berthon-Jones et al. 2010, "Mask and Components Thereof"); 20100006097 (Frater et al. 2010, "Quiet Blower Apparatus and System and Method for Reducing Blower Noise"); 20100043796 (Meynink et al. 2010, "Systems for Reducing Exhalation Pressure in a Mask System"); 20100078016 (Andrieux et al. 2010, "Battery Management for a Breathing Assistance System"); 20100147302 (Selvarajan et al. 2010, "Ventless Mask CPAP System"); 20100242967 (Burbank et al. 2010, "Sleep Apnea Therapy with Naso-Phyrangeal Bypass"); 20110270031 (Frazier et al. 2011, "System and Method for Airway Manipulation"); 20110270043 (McKenna 2011, "Air Movement Energy Harvesting with Wireless Sensors"); and 20110277765 (Christopher et al. 2011, "System for Providing Flow-Targeted Ventilation Synchronized to a Patient's Breathing Cycle").

SUMMARY AND LIMITATIONS OF THE PRIOR ART

To summarize the prior art, there are many methods and devices for harvesting energy from the human body in the prior art. There are also many methods and devices in the prior art for providing respiratory support for Obstructive Sleep Apnea (OSA) and other respiratory conditions such as snoring and Chronic Obstructive Pulmonary Disease (COPD). However, there are still millions people around the world who have Obstructive Sleep Apnea (OSA), and other respiratory conditions, who are not being adequately treated by the treatment options that are available in the prior art. Some of these people do not have access to dependable electrical power. They need an energy self-sufficient treatment option. Even among people who do have access to dependable electrical power, many people cannot tolerate being tethered to a machine while they sleep. They get tangled up in the air tube as they toss and turn. This can be hazardous as well as annoying. There remains a large unmet clinical need for alternative treatment options for OSA.

None of the prior art methods, devices, and systems for treatment of Obstructive Sleep Apnea (OSA), or for respiratory support in general, appear to provide all five of the following benefits: (1) minimally-invasive—no need for surgery or implantation of a device into the body; (2) energy self-sufficient and portable—no need for an external power source for direct operation or for recharging battery; (3) freedom of movement during sleep—no need to be tethered to an air pump or getting tangled up in an air tube as one tosses and turns while sleeping; (4) lots of fresh air to reduce the chances of hypercapnia—less carbon dioxide compared to passive exhalation resistance devices because energy harvested from gas outflow during exhalation is used to increase gas inflow during inhalation; and (5) provides the consumer and/or health care provider with the ability to adjust energy harvesting and positive airway pressure over multiple respiratory cycles—energy can be stored during the span of multiple respiratory cycles before it is used to provide positive airway pressure to correct, or avoid, an adverse respiratory event. The invention that will be disclosed herein can provide all five of these benefits for treatment of Obstructive Sleep Apnea (OSA) and possibly other respiratory conditions as well.

SUMMARY AND ADVANTAGES OF THIS INVENTION

This invention is a method, device, and system to provide respiratory assistance to people with Obstructive Sleep Apnea (OSA). It may also be helpful for people with Chronic Obstructive Pulmonary Disease (COPD) or for reduction of snoring. This invention can be embodied as a method of providing respiratory assistance comprising: harvesting energy from gas outflow during exhalation; and using that energy to increase gas inflow during inhalation, or during the period between exhalation and inhalation. In various examples, gas inflow can be an inflow of normal air or oxygen-enriched air. In an example, it may be used while a person sleeps. This invention can also be embodied as a device and a system to provide respiratory assistance comprising: one or more energy-harvesting members that harvest energy from gas outflow during exhalation; and one or more energy-using members that use the harvested energy to increase gas inflow during inhalation, or during the period between exhalation and inhalation.

Increased airway pressure can be therapeutic for respiratory conditions such as Obstructive Sleep Apnea (OSA). Positive pressure can help to keep a sleeping person's airway open. This positive airway pressure can be continuous. Alternatively, positive airway pressure can applied selectively during certain phases of the respiratory cycle, applied therapeutically to correct adverse respiratory events, or applied prophylactically to avoid adverse respiratory events. Positive pressure at the end of exhalation or during inhalation can be particularly beneficial for treating Obstructive Sleep Apnea (OSA). In various examples, this invention can provide Positive End-Expiratory Pressure (PEEP) or Continuous Positive Airway Pressure (CPAP).

This invention can be embodied in a self-contained energy-self-sufficient mask that does not require an air tube connection to a bedside blower or connection to an external power source. This can be a breakthrough treatment option for the millions of people around the world who have OSA, and who would benefit from positive airway pressure, but who live in areas that do not have a dependable source of electrical power and thus cannot use conventional CPAP systems.

This invention can also be an important positive airway pressure option for people who like to go camping or traveling where external electrical power is not available and battery life in a portable CPAP device is limited. This invention can also be a great improvement for people for whom being tethered by an air tube to a bedside unit is annoying or even hazardous. People who toss and turn in their sleep can get tangled up in the air tube from a mask to a bedside blower unit. Such behavior can also compress the tube and block airflow to the sleeping person, which can be hazardous. Also, people who like to sleep on their side and press their face against a pillow may adversely dislodge or compress an air tube connected to a conventional CPAP mask. All of these problems can be avoided with this invention.

Although there is a wide variety of methods, devices, and systems for treating Obstructive Sleep Apnea (OSA) in the prior art, there remains an unmet clinical need. This present invention fills this unmet need. Unlike any example in the prior art, this present invention offers the following five benefits for treatment of OSA: (1) minimally-invasive—no need for surgery to implant a device; (2) energy self-sufficient—no need for an external power source for direct operation or recharging a battery; (3) freedom of movement—no need to be tethered to an air pump during sleep; (4) avoid hypercapnia—less carbon dioxide compared to passive exhalation resistance devices because gas inflow is increased during inhalation; and (5) adjustable energy harvesting over multiple respiratory cycles—energy can be stored during multiple respiratory cycles before being used to correct, or avoid, an adverse respiratory event. This invention may also prove useful for treating other respiratory conditions such as snoring and Chronic Obstructive Pulmonary Disease (COPD).

INTRODUCTION TO THE FIGURES

These figures collectively show examples of how this invention may be embodied, but they do not limit the full generalizability of the claims.

Figure 2:
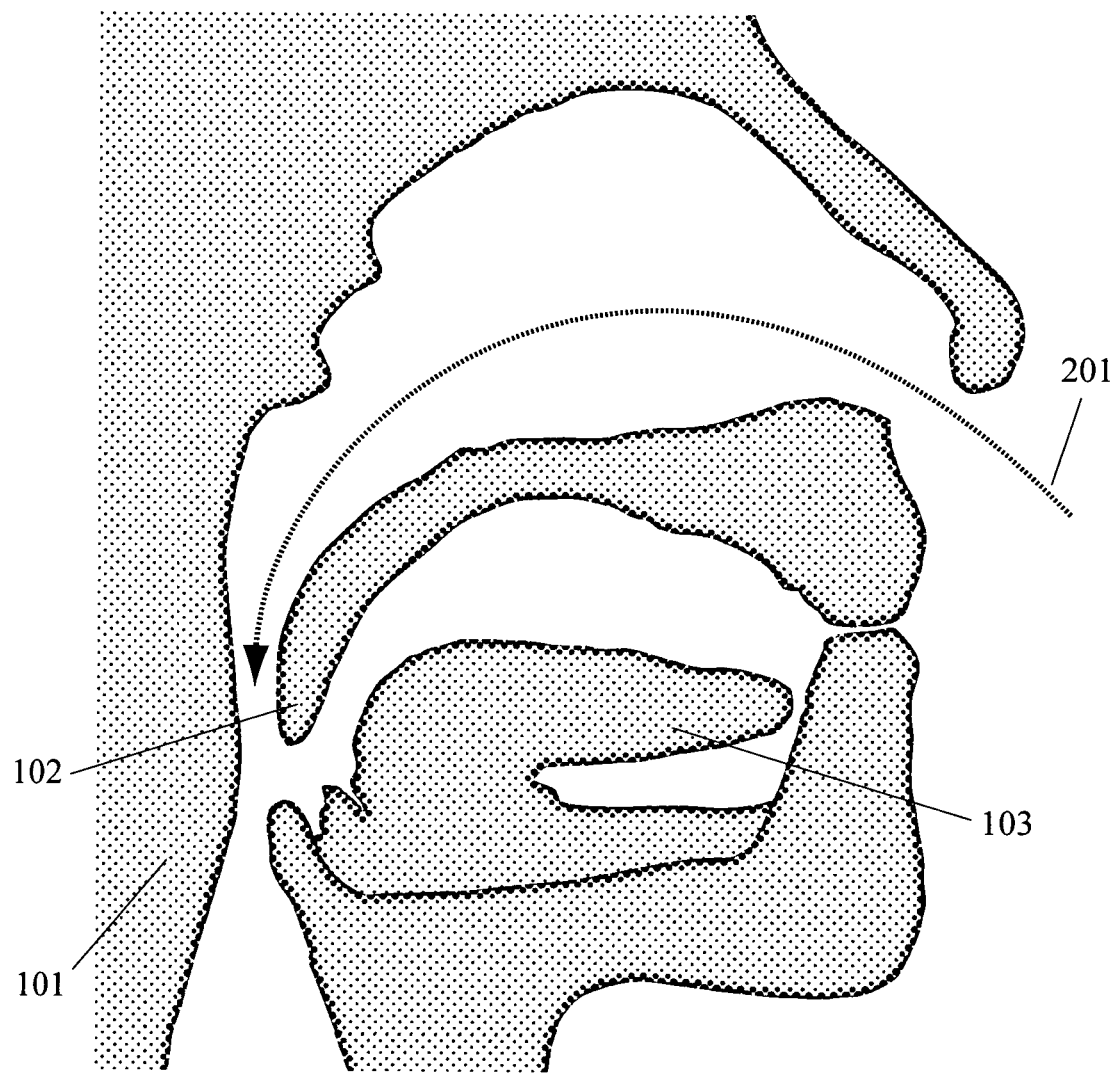
Figure 3:
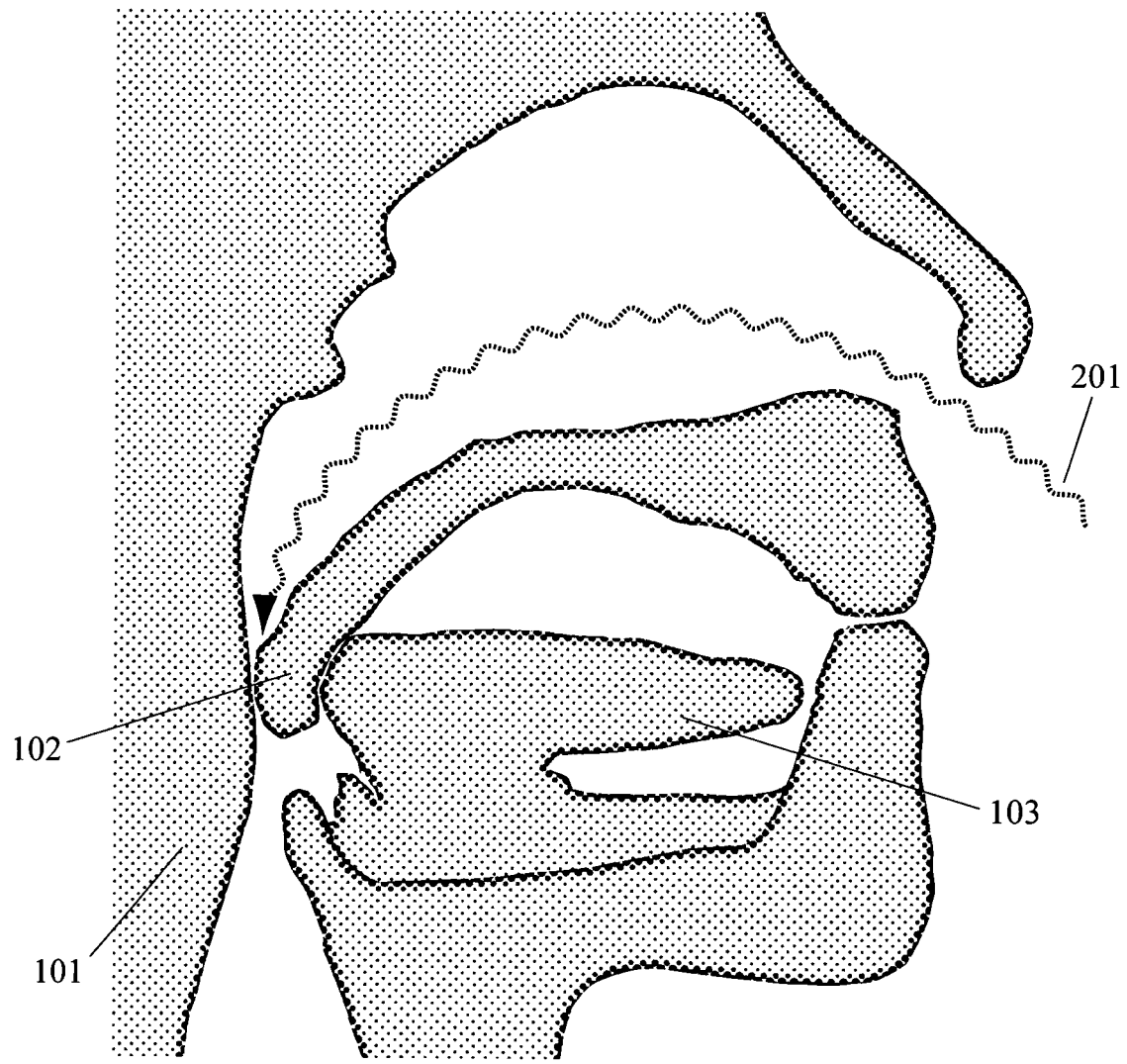

FIGS. 1-3 show a person's head during inhalation and exhalation, before the invention, in order to provide anatomical and physiological context for the invention that is shown in later figures.

FIG. 1 shows this person during unobstructed exhalation. FIG. 2 shows this person during unobstructed inhalation. FIG. 3 shows this person during inhalation that is obstructed by soft tissue pressing into the airway.

Figure 4:
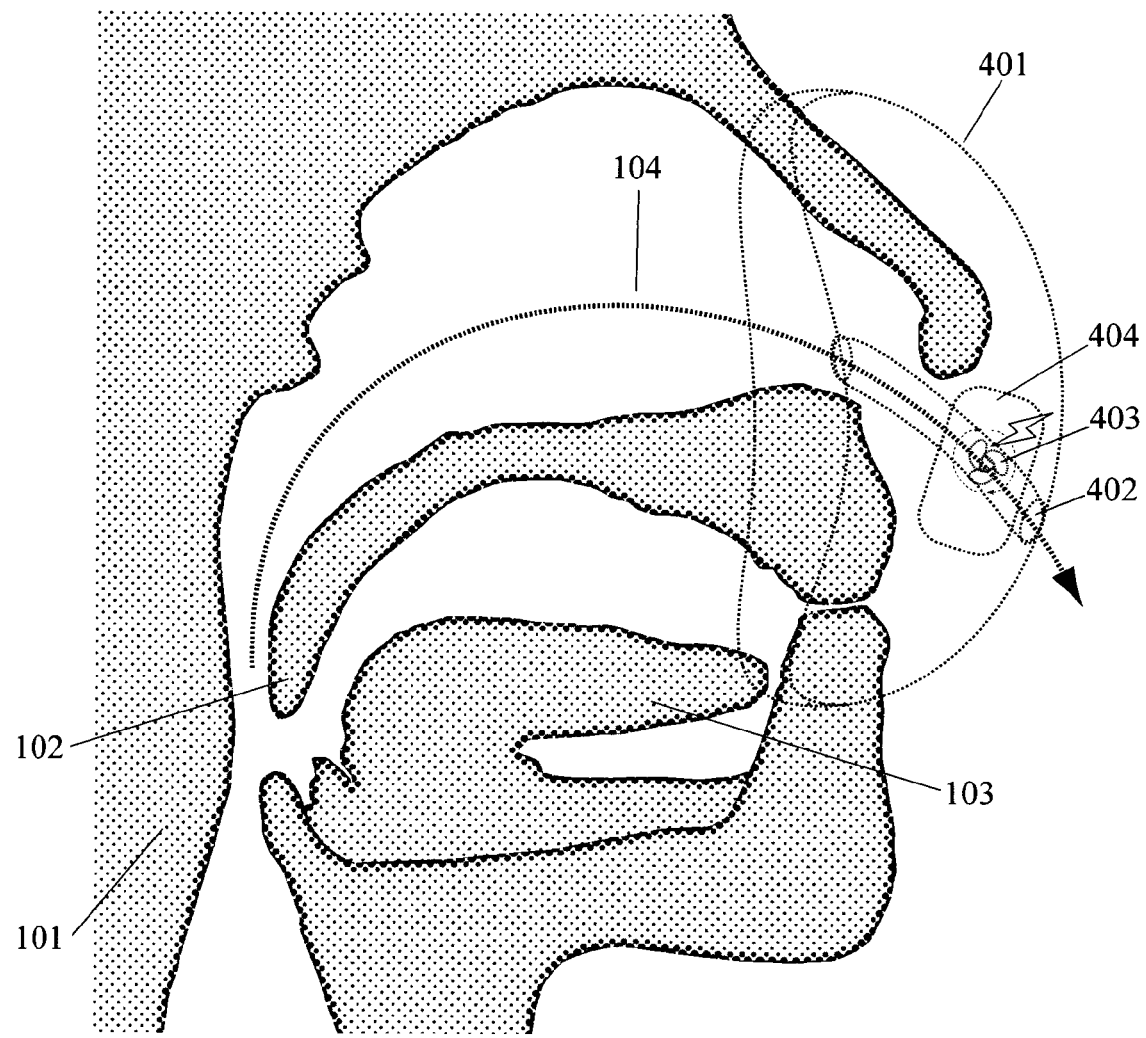
Figure 5:
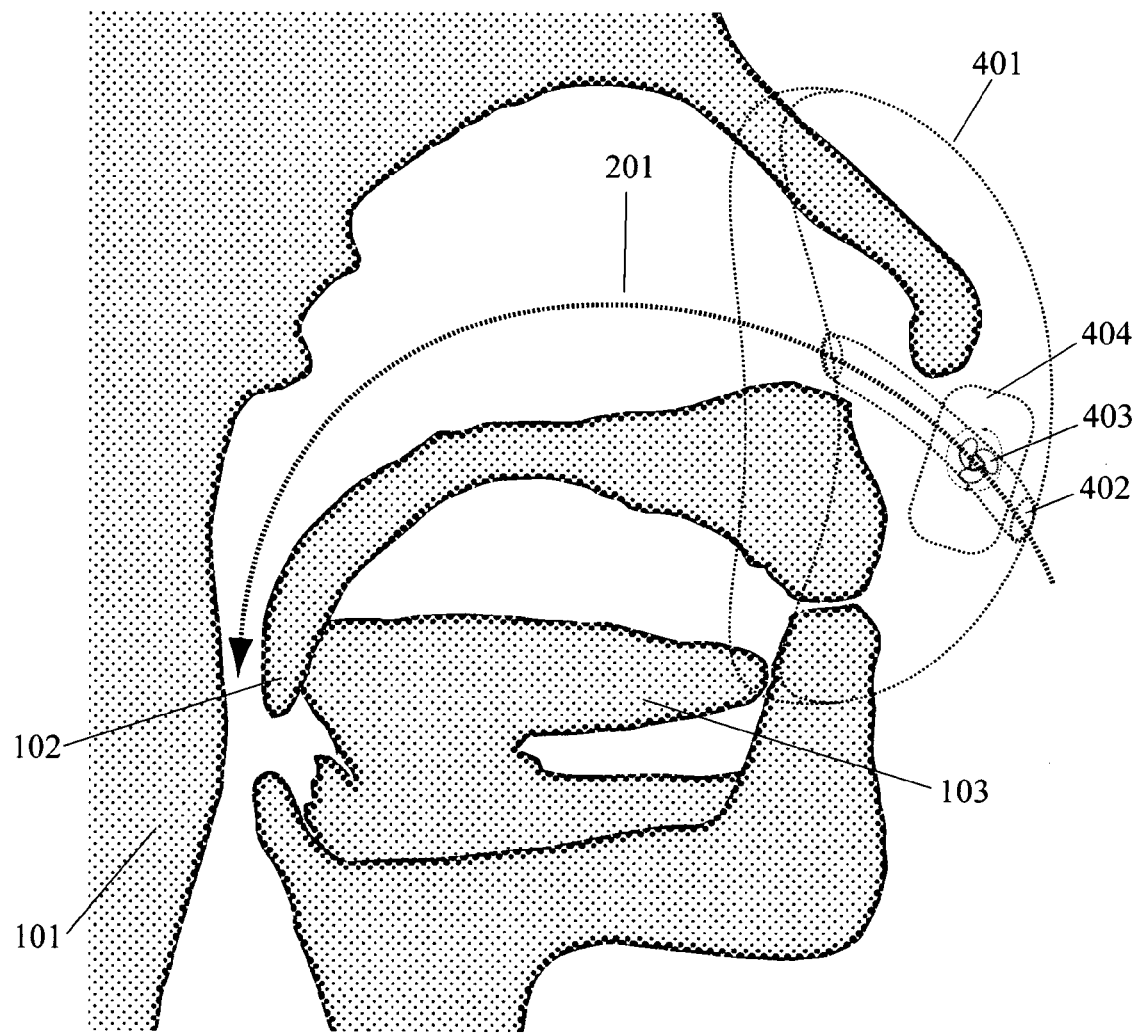

FIGS. 4-5 show this person's head with the addition of an example of the invention that is embodied as a self-contained energy-harvesting positive airway pressure mask. FIG. 4 shows this example while the mask is harvesting and storing energy from gas outflow during exhalation. FIG. 5 shows this example while the mask is using stored energy to increase gas inflow during inhalation.

FIGS. 6-19 show greater detail and more examples concerning how the energy-harvesting, energy-storing, and energy-using functions of this invention may be embodied.

Figure 6:
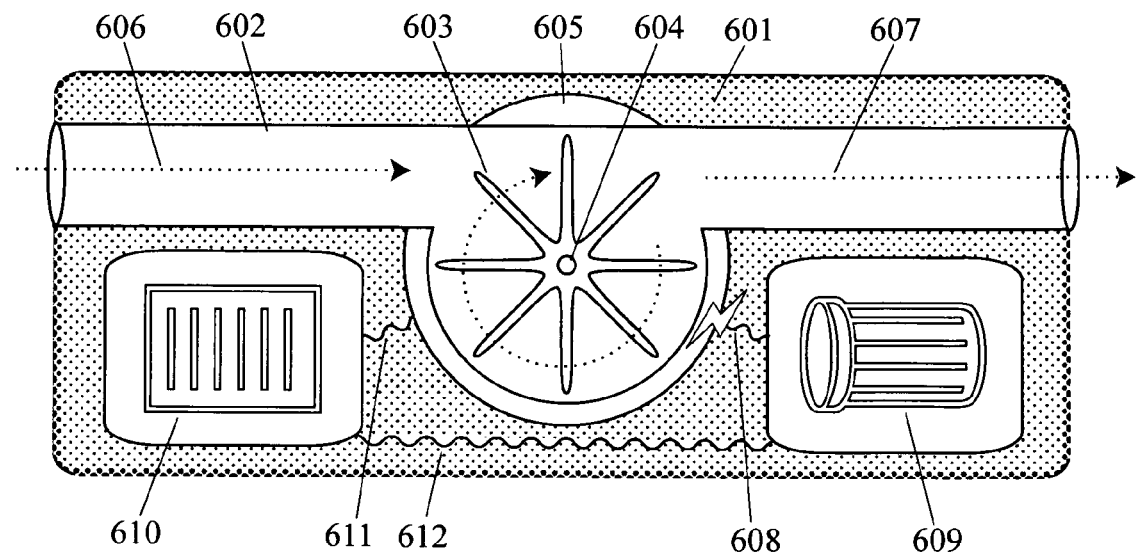
Figure 7:
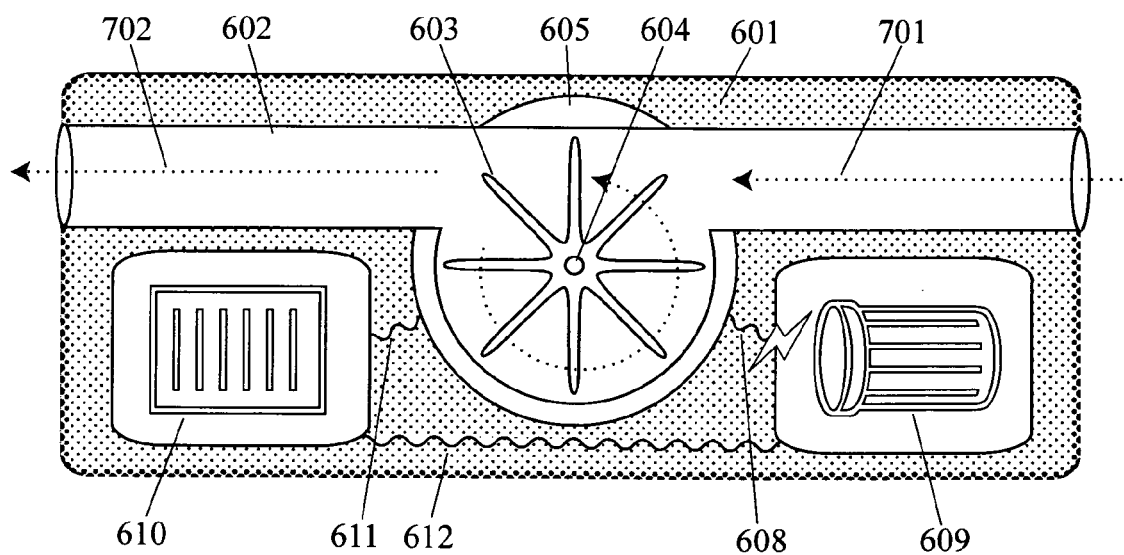

FIGS. 6-7 show an electricity-harvesting example of this invention comprising a housing with a single air-flow channel and a combined generator/actuator that can be integrated into a mask, nasal inserts, mouth appliance, or bedside unit. FIG. 6 shows this example during exhalation. FIG. 7 shows this example during inhalation.

Figure 8:
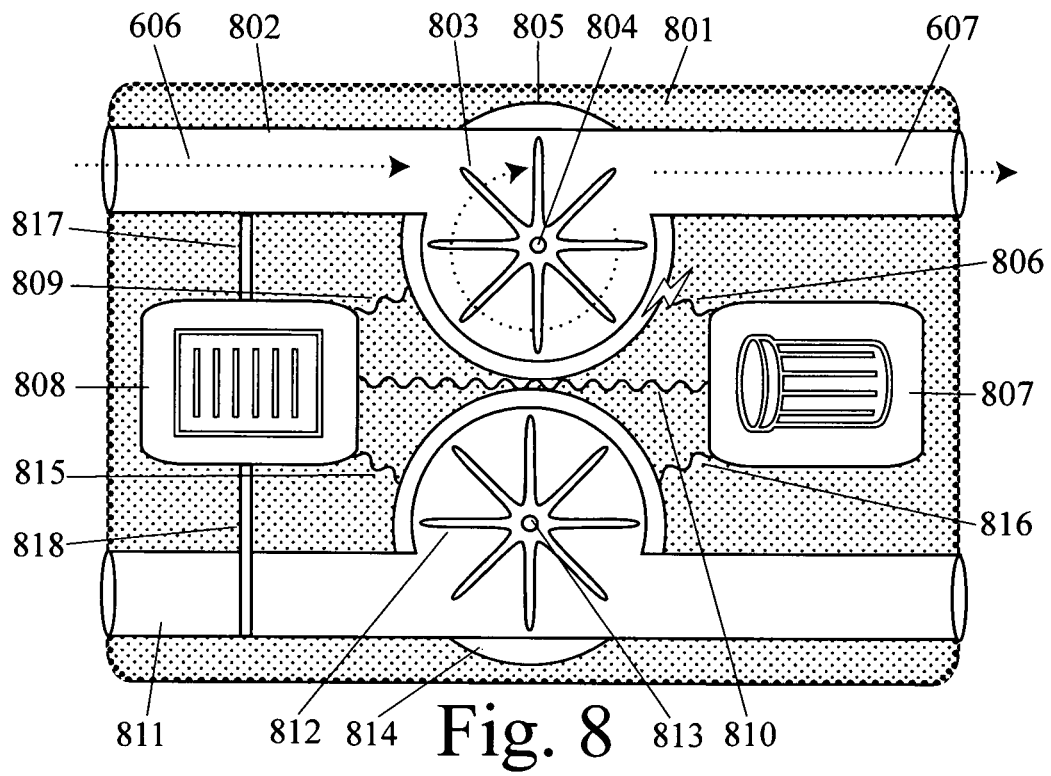
Figure 9:
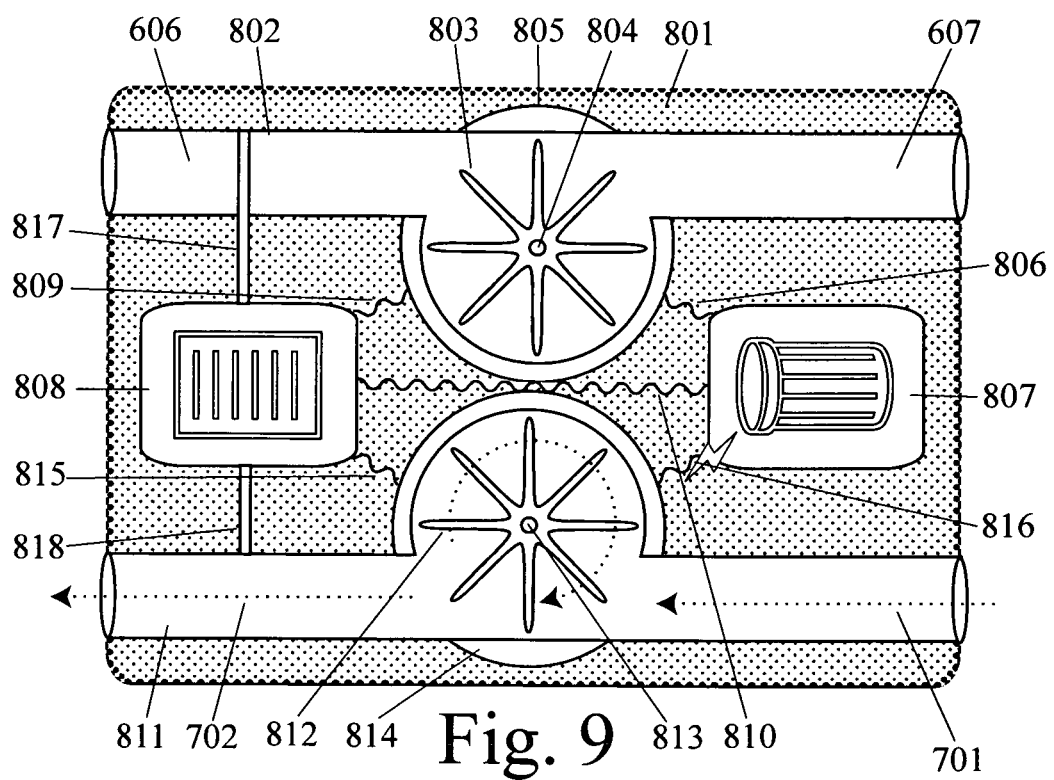

FIGS. 8-9 show an electricity-harvesting example comprising a housing with two air-flow channels and separate generator and actuator. FIG. 8 shows this example during exhalation. FIG. 9 shows this example during inhalation.

Figure 10:
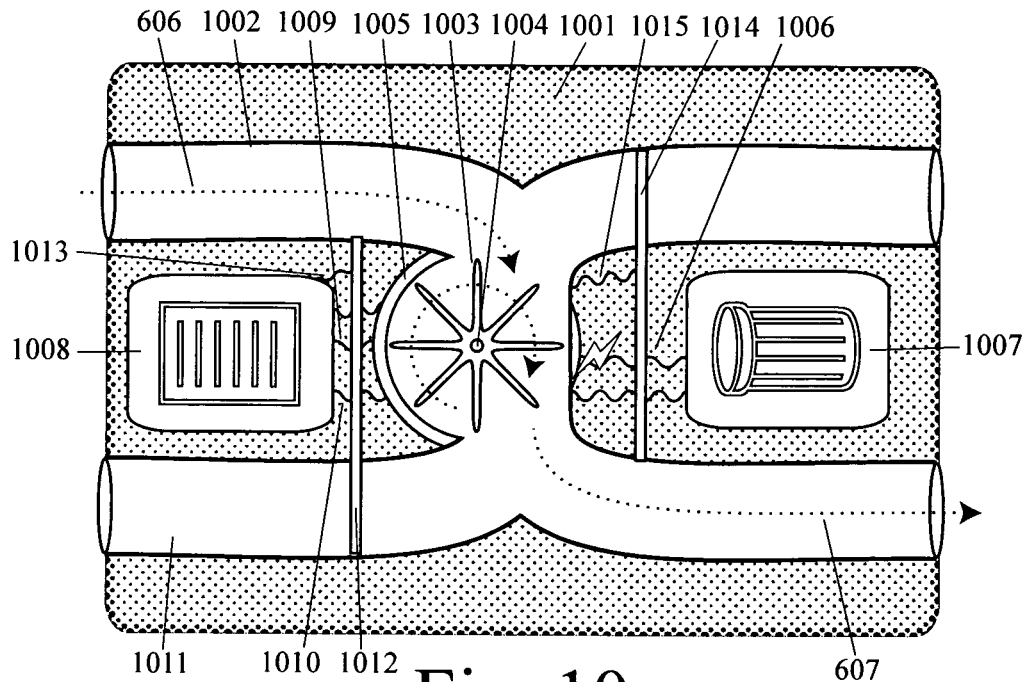
Figure 11:
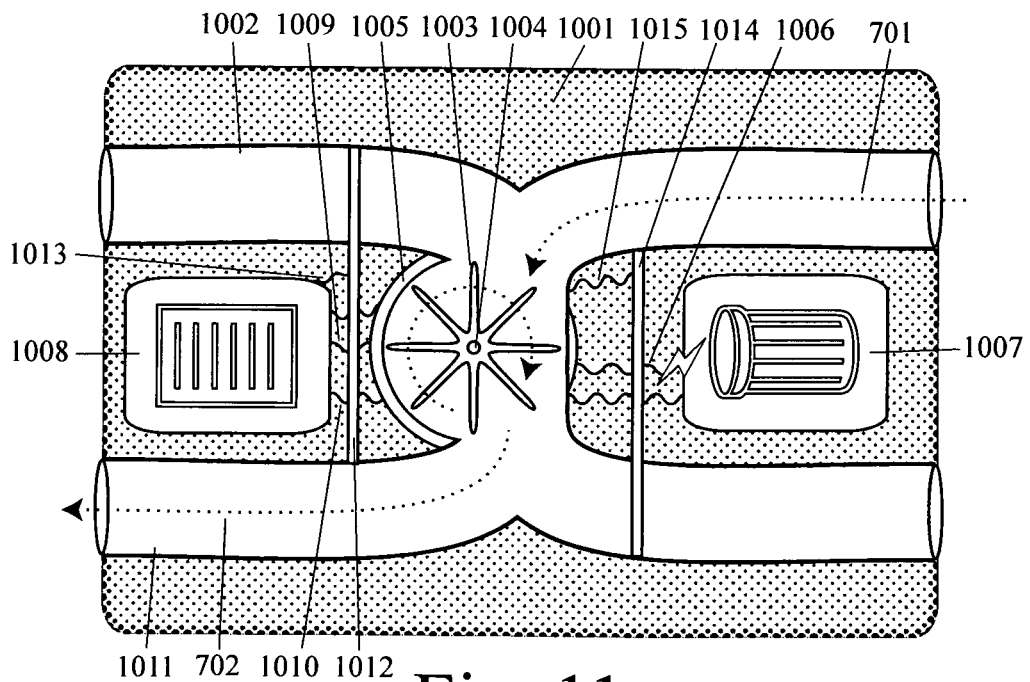

FIGS. 10-11 show an electricity-harvesting example comprising a housing with two air-flow channels and a combined generator/actuator. FIG. 10 shows this example during exhalation. FIG. 11 shows this example during inhalation.

Figure 12:
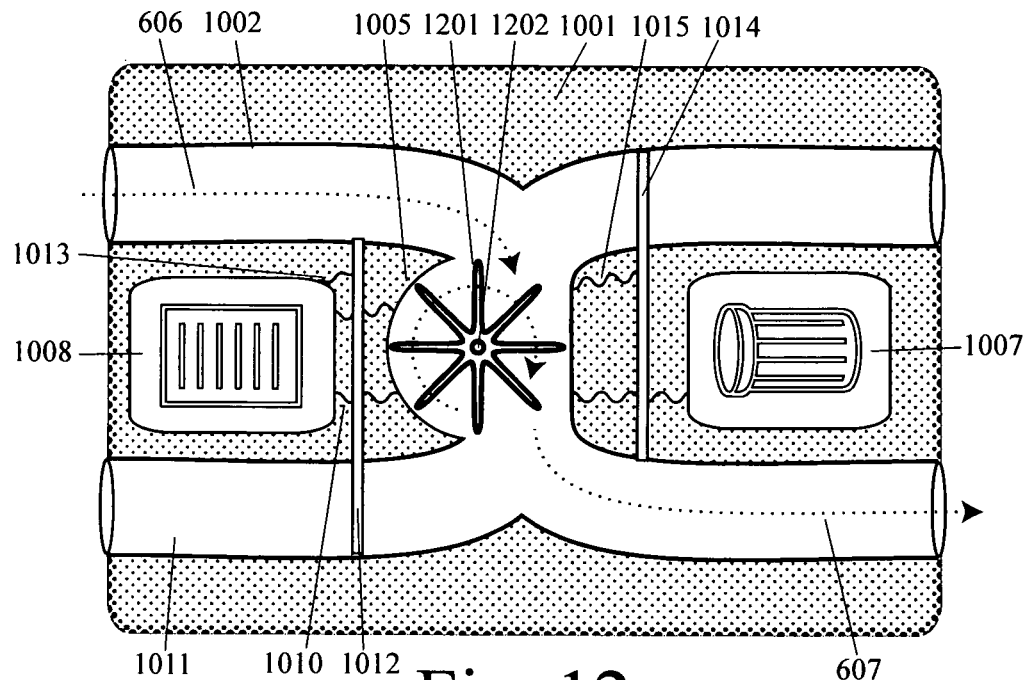
Figure 13:
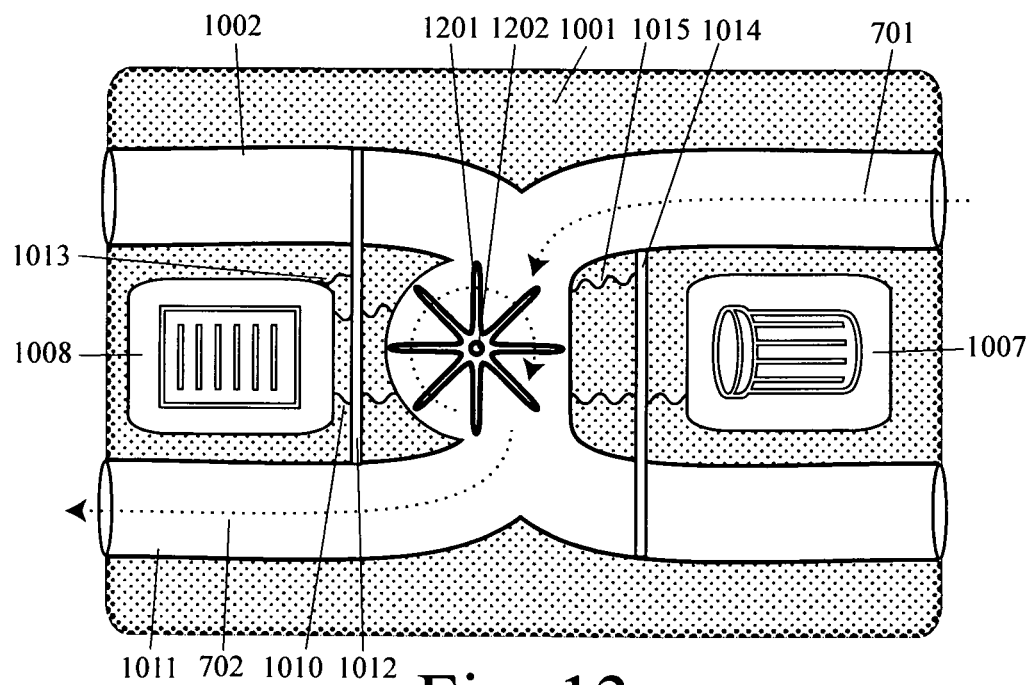

FIGS. 12-13 show a momentum-driven example comprising a housing with two air-flow channels and a common impeller that provides Positive End-Expiratory Pressure (PEEP). FIG. 12 shows this example during exhalation. FIG. 13 shows this example during inhalation.

Figure 14:
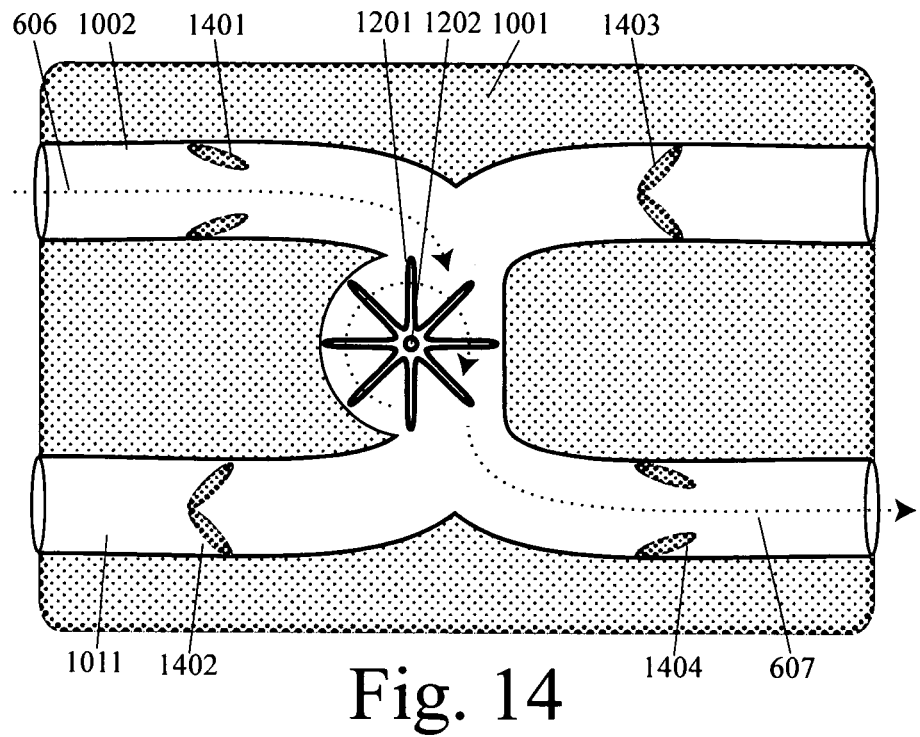
Figure 15:
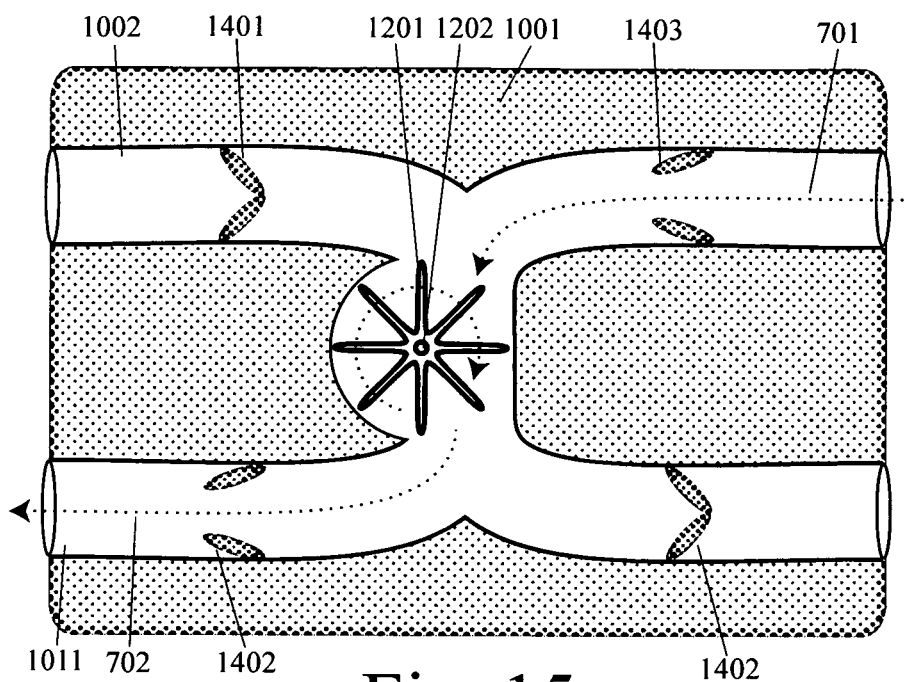

FIGS. 14-15 show a momentum-driven example comprising a housing with two air-flow channels and a common impeller that acts like a flywheel. FIG. 14 shows this example during exhalation. FIG. 15 shows this example during inhalation.

Figure 16:
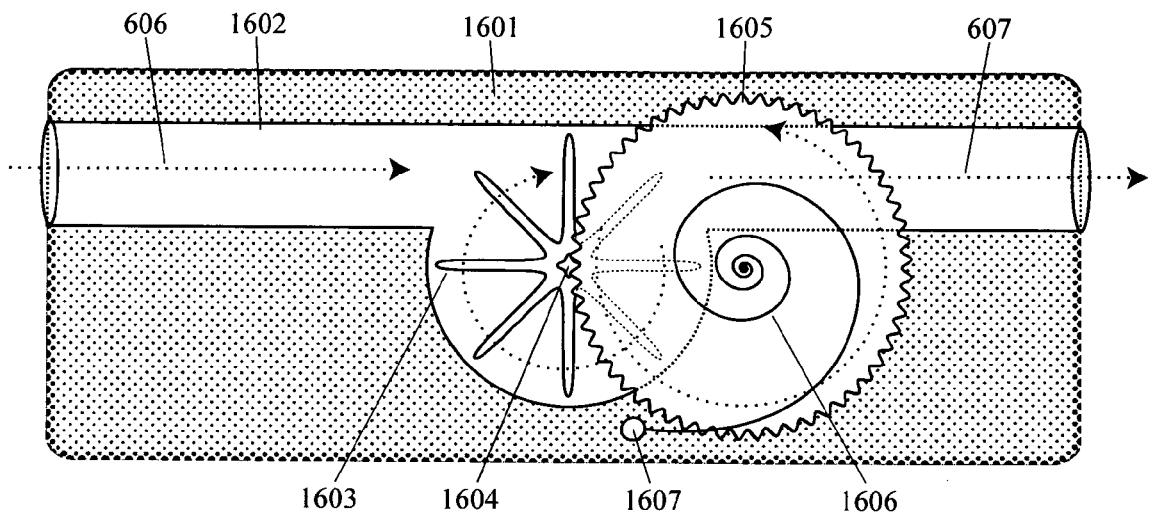
Figure 17:
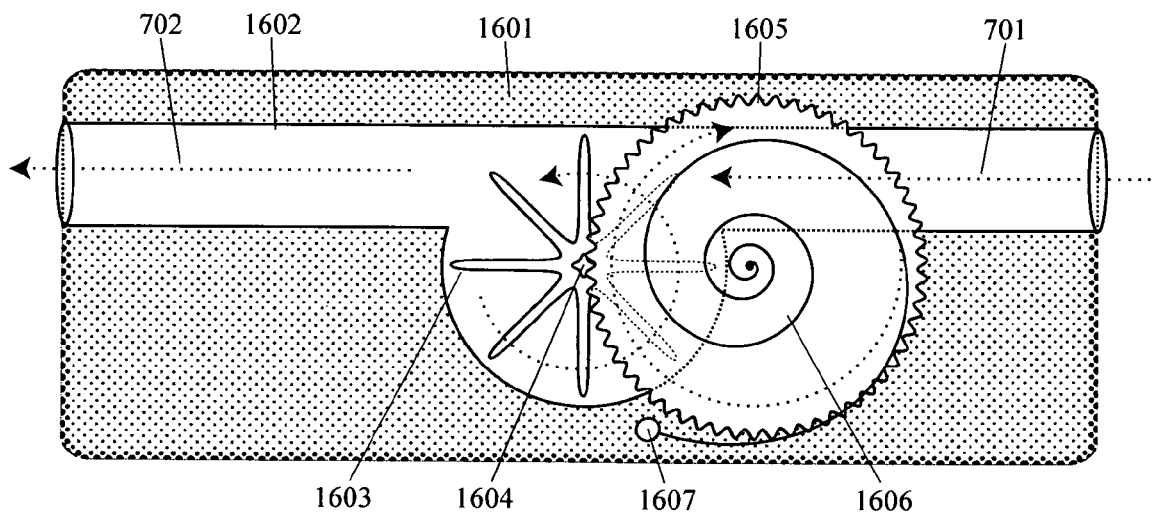

FIGS. 16-17 show an example in which energy from gas outflow during exhalation is stored in the form of tensile mechanical energy before it is used to increase gas inflow during inhalation. FIG. 16 shows this example during exhalation. FIG. 17 shows this example during inhalation.

Figure 18:
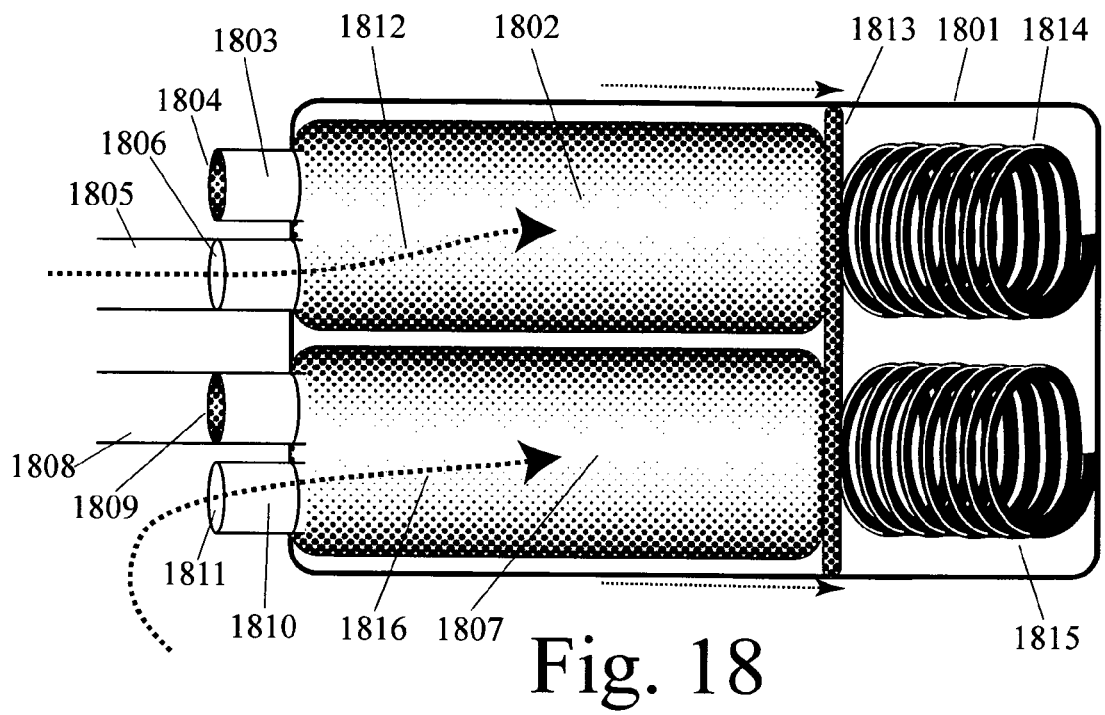
Figure 19:
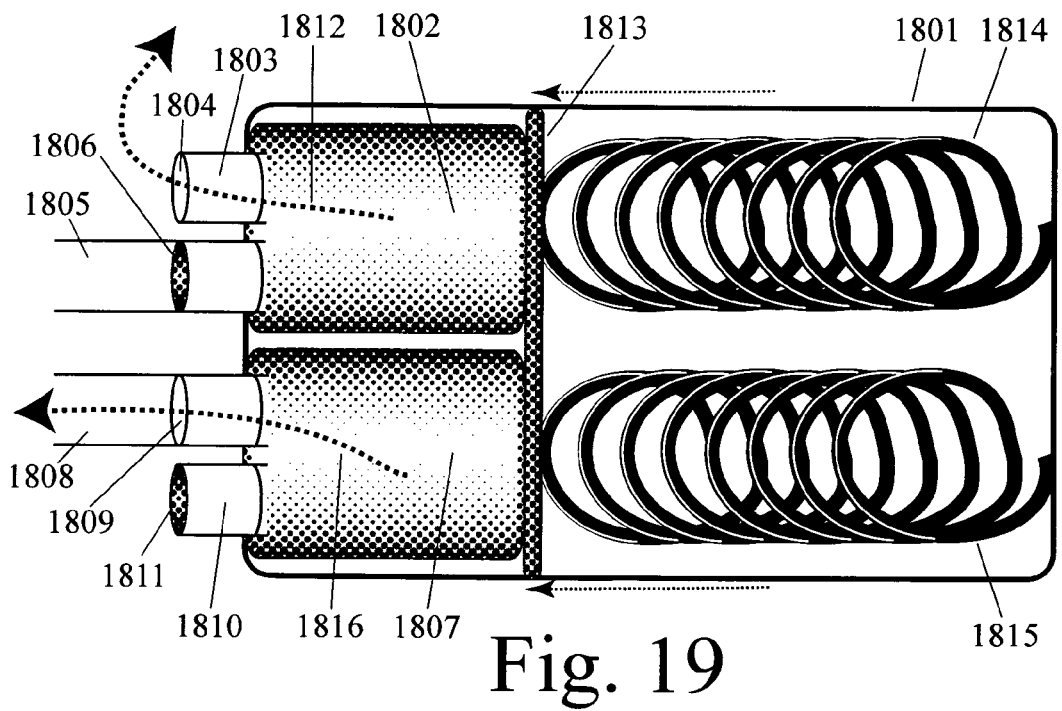

FIGS. 18-19 show an example in which energy from gas outflow during exhalation is stored in the form of pneumatic and tensile energy before it is used to increase gas inflow during inhalation. FIG. 18 shows this example during exhalation. FIG. 19 shows this example during inhalation.

DETAILED DESCRIPTION OF THE FIGURES

FIGS. 1-19 collectively show various examples of how this invention may be embodied as a method, a device, and a system to provide respiratory assistance to people with Obstructive Sleep Apnea (OSA) or other respiratory conditions. However, these examples are not exhaustive. These figures do not limit the full generalizability of the claims.

FIGS. 1-3 provide anatomical and physiological context for the invention that is shown in later figures. These three figures show a lateral cross-sectional view of the frontal/central portion of a person's head (101). FIG. 1 shows this person's head (101) during normal unobstructed exhalation. In FIG. 1, soft tissue (102) along the person's airway and the person's tongue (103) are in their proper positions and thus do not obstruct the airway. A stream of gas outflow during exhalation, represented by dotted line (104), travels through the airway and exits the body in an unobstructed manner. In these figures, the person's head (101) is shown as being upright with respect to the orientation of the page, which might imply that the person is standing. However, it is to be understood that this figure would apply to a person who is reclining and sleeping.

FIG. 2 shows this same lateral cross-sectional view of the person's head (101), but during normal unobstructed inhalation (instead of exhalation). In a manner similar to that shown in FIG. 1, FIG. 2 shows soft tissue (102) along the person's airway and the person's tongue (103) as being in their proper positions. They do not obstruct the person's airway. A stream of gas inflow during inhalation, represented by dotted line (201), travels through the airway and enters the lungs in an unobstructed manner. In this example, this gas inflow is an inflow of normal air. In another example, this gas inflow can be an inflow of oxygen-enriched air.

FIG. 3 shows this same lateral cross-sectional view of the person's head (101) when inhalation is obstructed by the collapse of the tongue and soft tissue into the airway while the person sleeps. In FIG. 3, soft tissue (102) along the person's airway, as well as the person's tongue (103), have moved from their proper positions and obstruct the airway. In this example, both soft tissue (102) and the tongue (103) have moved to obstruct the person's airway. In other examples, only one of these tissue structures may have moved to obstruct the person's airway. In other examples, airway collapse may occur at other locations closer to the lungs. In the example shown in FIG. 3, gas inflow during inhalation, represented by wavy dotted line (201), is obstructed and does not reach the lungs in the proper manner. This deprives the body of adequate oxygen. Although this oxygen deprivation is only temporary, it can happen repeatedly throughout the night to people who have Obstructive Sleep Apnea (OSA) and cause adverse health consequences over the long run.

The obstruction of the airway that is shown in FIG. 3 can be corrected, or avoided, by positive airway pressure. Positive airway pressure can move, and keep, the tongue and soft tissue out of the airway. This is particularly important during the beginning of the inhalation phase of respiration when airway obstruction is most likely to occur. Continuous Positive Airway Pressure (CPAP) increases pressure in the airway at all times. However, conventional CPAP systems require blower motors that run most or all of the time. This can be energy intensive. Even if a CPAP blower can run on battery power, battery life is limited by the energy demands of a motor that runs most or all of the time. The battery will have to be recharged relatively frequently. This is a problem in areas of the world without dependable access to electricity. Conventional CPAP devices also require that a person wears a mask with an air tube that effectively tethers the person to a bedside blower unit. This can be annoying, or even hazardous.

Many people with OSA who would benefit from positive airway pressure live in areas of the world that do not have access to dependable electrical power. Thus, they cannot use conventional CPAP devices. Even among people who live in areas which do offer dependable access to electrical power, many people who would benefit from positive airway pressure cannot tolerate current CPAP devices. Some of these people cannot tolerate CPAP devices because these devices require a person to be tethered by an air tube to a bedside blower unit. As they toss and turn in their sleep, they can become tangled up in this tube or this tube can become compressed. Also, people who sleep on their side often press their face against a pillow while they sleep. This exerts torque on the air tube and/or compresses the air tube, causing the mask to leak or restricting gas flow. This present invention can solve all of these problems—especially when it is embodied in a self-contained energy-self-sufficient mask (or nasal insert or mouth appliance) that is entirely powered by a person's own exhalation and does not require connection to an external blower unit.

FIG. 4 shows the same lateral cross-sectional view of the person's head (101) that was shown in FIGS. 1-3. However, now this figure also incorporates an example of how this invention may be embodied. This example of the invention is embodied in a self-contained, energy-self-sufficient positive airway pressure mask (401) that is worn on the face covering the nose and mouth. In this example, the mask forms a seal over both the nose and mouth. In other examples, this invention may be embodied as nasal inserts or a mouth appliance. In various examples, a mask, nasal insert, or a mouth appliance may be made from one or more materials selected from the group consisting of: an ethylene propylene diene monomer, latex, nylon, polycarbonate plastic, polyethylene, polypropylene, polystyrene, polyurethane, polyvinyl chloride, silicone, and vulcanized rubber.

In FIGS. 4-5, the self-contained positive airway pressure mask is shown as translucent so that a reader can see the interior gas channel and the energy-harvesting mechanism within the mask. In reality, the mask would likely be opaque. In an example, this mask may be held against the face by straps. In an example, a mask may be held against the face by a levered member that is attached to the head. In an example, a mask may be held against the face by connection with an appliance that is retained in the mouth. In an example, a mask may be held against the face by connection with members that are inserted into the nostrils. There are many alternative methods in the prior art for attaching a mask, nasal inserts, or mouth appliance to a person and the precise means of attachment is not central to this invention, so the precise means of attachment is not specified herein.

FIG. 4 shows a positive airway pressure mask embodiment of this invention during the exhalation phase of respiration. In this mask embodiment of the invention, there is a single gas channel (402) through the mask that allows gas to flow outwards during exhalation (from inside the mask to outside the mask) and allows gas to flow inwards during inhalation (from outside the mask to inside the mask). In other examples, there may be more than one gas flow channel. For example, there may be one gas flow channel for gas outflow during exhalation and a different gas flow channel for gas inflow during inhalation. In an example, gas inflow can be an inflow of normal air. In another example, gas inflow can be an inflow of oxygen-enriched air. In various examples, there may be one-way airflow valves to direct gas inflow and gas outflow. In various examples, there may be airflow valves in one or more gas channels that can be opened or closed by a control mechanism during different phases of the respiratory cycle.

FIG. 4 also shows a gas flow impeller (403) within gas channel (402). In other examples, there may be multiple gas flow impellers, or other means of transducing the kinetic motion of gas outflow into another form of energy that are located within one or more gas channels. In this example, the gas flow impeller (403) is connected to a component (404) that comprises a generator/actuator, a battery, and a control mechanism. In this example, the impeller rotates around an axis that is substantively parallel to the longitudinal axis of the gas channel. In another example, the impeller may rotate around an axis that is substantively perpendicular to the longitudinal axis of the gas channel. More details with respect to the different ways in which an impeller may be configured within a gas channel are shown in FIGS. 6-17.

In FIG. 4, when the person exhales, gas outflow from exhalation (104) spins the impeller clockwise. This rotation generates electricity through the generator/actuator. This electricity is then stored within the battery. In this example, there is a one-to-one ratio between the rate of rotation of the impeller and the rate of rotation of a central shaft of the electricity generator. In other examples, this invention may include a series of gears between the impeller and the generator shaft which either gear-up or gear-down this ratio. In an example, a series of gears may make this ratio greater than one to increase rotational torque for the generator. In another example, a series of gear may make this ratio less than one to increase rotational speed for the generator.

In this example, kinetic energy from rotation of the impeller is used directly, in real time, to drive the generator shaft. In another example, kinetic energy from rotation of the impeller may be accumulated and stored, in an intermediate step or mechanism, before being used to drive the generator. This accumulation function can be useful if there is a minimum rate of generator shaft rotation and/or torque that is required to generate electricity and if this minimum is difficult to achieve with direct, real time, rotation of the impeller. For example, kinetic energy from the rotation of the impeller, at a relatively slow rotation speed and/or with relatively low torque, may be accumulated and stored in a spring winding mechanism over multiple respiratory cycles. In an example, a spring winding mechanism may accumulate energy during multiple exhalation cycles using a clockwork catchment mechanism. Energy accumulated in the wound spring may then be released to rotate the generator shaft at a faster rate or with greater torque than would be possible with direct real-time rotation of the impeller.

In the example shown in FIG. 4, the impeller, generator/actuator, and battery comprise part of a method and means of energy-harvesting that transduces and stores some of the kinetic energy of gas outflow during exhalation. In various examples, an energy-harvesting method and means may be selected from one or more of the group consisting of: an impeller, a fan, a turbine, or some other member that is rotated by moving gas; a piston, a diaphragm, a balloon, a compressible chamber, or some other member that is displaced by moving gas; and a generator. FIG. 4 introduces a chain of energy-transducing members in order to show their overall operation as well as the anatomic and physiological context in which they function. Subsequent figures, including FIGS. 6-19, focus on the components in greater detail and show more specifics about the various ways in which a chain of energy-transducing members can be configured.

FIG. 5 shows the same lateral cross-sectional view of the person's head (101) and the same embodiment of this invention that was shown in FIG. 4, but now it is shown during the inhalation phase of the respiratory cycle. This figure shows how a chain of energy-transducing members can be used to cause a therapeutic increase in gas inflow during inhalation, or during the pause between exhalation and inhalation. In this example, electricity from the battery in component (404) powers the actuator function of the generator/actuator in component (404) which spins the impeller (403) counter-clockwise. This spinning motion increases gas inflow through the airway. (201) which provides positive airway pressure during inhalation. In another example, gas inflow may be increased immediately prior to the start of the inhalation phase of the respiratory cycle, such as during the pause after exhalation and before inhalation begins. In an example, gas inflow can be inflow of normal air. In another example, gas inflow can be inflow of oxygen-enriched air.

In the example of this invention that is shown in FIGS. 4-5, the same generator/actuator and impeller that is used to harvest energy from gas outflow during exhalation is also used as an energy-using means to increase gas inflow during inhalation. During inhalation, these same members use energy stored from energy-harvesting. In another example, a different mechanism, or series of energy-transducing members, may be used to increase gas inflow during inhalation. In various examples, an energy-transducing means for increasing gas inflow during inhalation may be selected from one or more of the group consisting of: a impeller, fan, turbine, or other member that moves gas by rotating; a piston, a diaphragm, a balloon, compression chamber, or some other member that moves gas by displacement; and an electric motor or actuator.

In various examples, there may be two gas channels, one channel for exhalation and one channel for inhalation, with different energy-transducing members in each channel. In an example, there may be one gas channel through the mask with an impeller connected to a generator to harvest energy from gas outflow during exhalation and a second gas channel through the mask with an impeller connected to an actuator to increase gas inflow during inhalation.

In this example, there is a control mechanism within component 404 that controls the timing of energy harvesting relative to the timing of energy expenditure. This control mechanism can adjust the time lag between when energy is harvested from gas outflow and when energy is used to increase gas inflow. In an example, this control mechanism may include a microchip or other microscale computing device. In an example, a microchip may be powered by the battery. In this example, the control mechanism creates a time delay between the time when the impeller stops spinning clockwise (as the rate of gas outflow during exhalation subsides) and the time that the actuator is activated to spin the impeller counter-clockwise (to accelerate gas inflow during inhalation, or just prior to inhalation). In an example with two gas channels, one for gas outflow during exhalation and one for gas inflow during inhalation, a control mechanism may alternately close one channel and open the other. In an example, the timing of which channel is open or closed can be determined by the phase of the respiratory cycle. In an example, the phase of the respiratory cycle may be identified within the control mechanism by analysis of the results from sensors that measure the direction of airflow or sounds received by a microphone.

In this example, energy harvested from exhalation is stored in the form of electricity in a battery. In this example, a method, device, and system for providing respiratory assistance comprises harvesting energy, wherein electrical energy is harvested from the kinetic energy of gas outflow during exhalation and is stored before it is used to increase gas inflow during inhalation. In various other examples, energy harvested from exhalation may be stored in a form selected from one or more of the group consisting of: electrical energy; mechanical energy; pneumatic energy; chemical energy; biological energy; thermal energy; and light energy. In various examples, energy from the energy-harvesting means may be stored in an energy-storing member selected from one or more of the group consisting of: a battery; an energy-storing microchip; a spring; an elastic member; an inflatable member; and a pressurized compartment.

A method, device, and system for providing respiratory assistance can involve storing energy, wherein energy is harvested and accumulated from gas outflow during exhalation over the span of multiple respiratory cycles. A method, device, and system for providing respiratory assistance can involve harvesting energy wherein energy is harvested and accumulated from gas outflow during exhalation over the span of multiple respiratory cycles. A method, device, and system for providing respiratory assistance can involve storing energy, wherein energy is stored and accumulated from the gas outflow of exhalation during multiple respiratory cycles.

In an example, a method, device, and system for providing respiratory assistance can involve storing energy that is accumulated from exhalation during multiple respiratory cycles, wherein this energy is used to increase airway pressure only during selected respiratory cycles or during selected respiratory events. In an example, a device may be used selectively to increase airway pressure only during certain cycles of inhalation when respiratory monitoring indicates that such action is needed to correct, or avoid, an acute episode of a respiratory condition. There is ongoing progress in the prior art concerning the development of sensors and algorithms that detect, or predict, occurrences of airway obstruction during sleep. Since the precise means of airway obstruction detection and prediction is not central to this invention and since good progress is being made along these lines in the prior art, we do not specify the precise means of obstruction detection or prediction here.

In an example, a pulse of pressurized gas may be administered only at certain times during certain respiratory cycles while a person is sleeping. Such a pulse can help to reverse, or avoid, airway obstruction in a person who has Obstructive Sleep Apnea (OSA). Such a pulse can also help to stop, or avoid, soft tissue vibration in a person who snores. Such selective use of positive gas pressure or gas pulsing, as opposed to provision of continuous positive pressure, can conserve energy. This can help to make this method, device, and system more energy-self-sufficient, more compact, and more portable.

In an example, this invention can be a method, a device, and a system for selectively providing positive airway pressure while a person sleeps. In addition to being embodied in a self-contained and self-powered mask as shown in FIGS. 4-5, this invention may also be embodied as self-contained, self-powered nasal inserts or as a mouth appliance that does not require any contact with the person's cheeks, nose exterior, chin, or forehead. Such an embodiment can benefit people for whom conventional CPAP masks cause marks on their face or cause their face to break out. More generally, such an embodiment can appeal to people with respiratory conditions that should be treated by positive pressure during sleep, but for whom conventional CPAP systems are too cumbersome, too constraining, too uncomfortable, and/or too immobile.

FIGS. 4-5 show an example of a method of providing respiratory assistance that can be used to help a person with Obstructive Sleep Apnea (OSA), a person who snores, or a person with Chronic Obstructive Pulmonary Disease (COPD). This method comprises: harvesting energy from gas outflow during exhalation; and using that energy to increase gas inflow during inhalation. With respect to Obstructive Sleep Apnea (OSA), this method can help to keep the person's airway open while they sleep by selectively increasing airway pressure during inhalation, during the period between exhalation and inhalation, or during selected respiratory events.

Continuous Positive Airway Pressure (CPAP) is a common therapeutic method for addressing Obstructive Sleep Apnea (OSA) by providing continuous positive airway pressure to help keep a person's airway open while they sleep. However, people in many areas of the world do not have access to dependable electrical power to use CPAP. Even for people in areas of the world who do have access to dependable electrical power, they may not be able to use CPAP while camping or traveling.

There are also many people who have access to dependable electrical power, but who cannot tolerate wearing a CPAP mask because it tethers them to bedside blower unit. As they toss and turn in their sleep, they can become tangled up in the air tube that connects the CPAP mask to a beside blower unit. The air tube can also become compressed, depriving the person of air. Further, for people who sleep on their side and press their face against a pillow, this behavior can dislodge or compress the air tube that connects a CPAP mask to a bedside blower unit. For all of these reasons, a self-contained energy-self-sufficient method, device, and system that provides positive airway pressure to treat obstructive sleep apnea addresses an important unmet clinical need.

Airway collapse associated with Obstructive Sleep Apnea (OSA) is particularly common during the onset of inhalation. Besides the positive clinical evidence for Continuous Positive Airway Pressure (CPAP) as a means of treating Obstructive Sleep Apnea (OSA), there is also evidence that non-continuous positive airway pressure, applied in selective manner, can also be therapeutic for addressing OSA. For example, Positive End-Expiratory Pressure (PEEP) can be therapeutic for treating OSA. Non-continuous airway pressure can provide therapeutic benefit without requiring as much energy as continuous airway pressure. This can have advantages in terms of achieving partial or total energy self-sufficiency for an OSA method, device, and system.

It is possible that a high energy-efficiency version of this invention may one day be able to harvest enough energy from exhalation in order to provide Continuous Positive Airway Pressure (CPAP) without the need for any supplemental power from an external power source. However, for the near future, it is likely that this invention will at least be able to harvest enough energy from exhalation to provide non-continuous but therapeutic Positive End-Expiratory Pressure (PEEP). In an example, this invention can provide PEEP with minimal need for an external power source. Ideally, this invention will be completely energy self-sufficient—harvesting enough energy from exhalation to provide PEEP without any need for a supplemental external power source.

An energy self-sufficient method, device, and system for treating obstructive sleep apnea offers tremendous advantages over technology in the prior art in terms of access, portability, and freedom of movement in sleep. Such a method, device, and system can be used virtually anywhere in the world to treat sleep apnea. It is not dependent on access to an external power source to directly power the device or to recharge batteries. Even batteries need to be recharged, especially with energy-intensive continuous positive pressure CPAP blowers. An energy self-sufficient method, device, and system for providing positive airway pressure, such as the invention disclosed herein, can extend the benefits of positive airway pressure treatment for OSA to millions of people around the world for whom such treatment is not currently possible.

Even for people with OSA who live in countries where access to continuous power is generally available, a truly portable and energy self-sustaining positive airway pressure device can provide these people with the freedom to travel and to go camping without having to give up the benefits of positive airway pressure treatment for their OSA. Such a device can also be invaluable in emergency conditions caused by hurricanes, earthquakes, ice storms, or other causes of large-scale extended loss of electrical power.

There are even benefits of such a method, device, and system in circumstances wherein unlimited external power is available. In examples of this invention wherein the energy-harvesting and gas inflow accelerating components are part of a mask, nasal insert, or other self-contained device that is worn on the head, there is no longer any need for an air tube that tethers a sleeping person to a bedside blower unit. This frees the sleeping person from having to deal with being tethered to an external unit while they sleep. This person can now toss and turn to their heart's content, without having to worry about becoming tangled or compressing an air tube. Also, for people who sleep on their side (which is generally better for sleep apnea than sleeping on one's back) this invention offers new freedom for a person to press their face against a pillow without having to worry about torquing or compressing an air tube.

The example shown in FIGS. 4-5 can also be described as a method of providing respiratory assistance, while a person sleeps, comprising: transducing and storing energy from gas outflow during exhalation; and using that stored energy to increase gas inflow during inhalation, or during the period between exhalation and inhalation. Energy is transduced when it is changed from one form of energy to another. In this example, a portion of the kinetic energy of gas outflow during exhalation is transduced into rotational kinetic energy by an impeller. This rotational energy, in turn, powers a generator that generates electricity. This electricity is stored in a battery. Then this stored electricity is used to increase gas inflow during inhalation.

The example of this invention that is shown in FIGS. 4-5 can also be viewed as the embodiment of a device and a system, not just a method, for providing respiratory assistance to a person with Obstructive Sleep Apnea (OSA), a person who snores, or a person with Chronic Obstructive Pulmonary Disease (COPD). It can be viewed as a relatively self-contained positive airway pressure device and system. For example, FIGS. 4-5 show a device and a system for providing respiratory assistance while a person sleeps comprising: one or more energy-harvesting members that harvest energy from gas outflow during exhalation; and one or more energy-using members that use the harvested energy to increase gas inflow during inhalation or during the period between exhalation and inhalation. With respect to OSA, this device may be worn while a person sleeps to keep their airway open.

FIGS. 4-5 show an example of this invention in which "an increase in gas inflow" is operationalized as an increase in the rate of gas inflow. In various examples, "an increase gas inflow" may be selected from the group consisting of: an increase in the rate of gas inflow; an increase in the pressure of gas inflow; an increase in the volume of gas inflow; and an increase in the duration of gas inflow. Although these parameters of gas inflow are related by the laws of physics and the equations of fluid dynamics, different variations in gas inflow rate, pressure, volume, and duration may be optimally therapeutic in different clinical situations. Also, different variations in gas inflow rate, gas pressure, gas volume and gas flow duration may require different amounts of energy. Certain combinations may achieve therapeutic efficacy with lower energy requirements. In various examples, minimal energy combinations may be chosen for embodiment of this method, device, and system of respiratory support.

FIGS. 4-5 show an example of this invention in which energy is harvested from gas outflow during exhalation using an impeller as an energy-transducing member. In various examples, energy may be harvested from gas outflow during exhalation using one or more energy-transducing members selected from the group consisting of: an impeller, turbine, fan, pinwheel, flywheel, or other member that is rotated by gas outflow; an electricity-producing generator; a motor; an actuator; a spring; a diaphragm, balloon, piston or other member that is displaced by gas outflow; and a piezoelectric member. In an example, the force of gas outflow during exhalation can cause the impeller to spin, which rotates the central shaft of an electricity generator, which generates electricity, which is stored in a battery, which is applied in the other direction to use the generator as an electric motor during inhalation, which rotates the impeller, which then therapeutically increases the rate of gas inflow during inhalation.

In the example of this invention that is shown in FIGS. 4-5, energy that is harvested during exhalation is used to increase gas inflow during inhalation, or during the period between exhalation and inhalation, using an impeller as an energy-transducing member. In other example, energy may be used to increase gas inflow during inhalation, or during the period between exhalation and inhalation, using one or more energy-transducing members selected from the group consisting of: an impeller, turbine, fan, pinwheel, flywheel, or other member that is rotated by gas outflow; an electricity-producing generator; a motor; an actuator; a spring; a diaphragm, balloon, piston or other member that is displaced by gas outflow; and a piezoelectric member.

FIGS. 4-5 show an example of this invention embodied as a method, a device, and a system for providing respiratory assistance wherein an energy-harvesting member and an energy-using member are both located in a mask that covers a person's nasal and oral openings. This example shows a method and device and system for providing respiratory assistance wherein harvesting energy from gas outflow and using energy to increase gas inflow are functions that are part of a mask that covers a person's nasal and/or oral openings.

In an example, harvesting energy from gas outflow may provide at least 50% of the energy that is required to increase gas inflow during inhalation, or during the period between exhalation and inhalation. In an example, harvesting energy from gas outflow during multiple respiratory cycles may provide 100% of the energy that is required to increase gas inflow during inhalation, or during the period between exhalation and inhalation, for selected respiratory cycles.

In an example, this invention may be embodied in a device that provides respiratory assistance comprising: one or more energy-harvesting members that harvest energy from gas outflow during exhalation; and one or more energy-using members that use the harvested energy to increase gas inflow during inhalation or during the period between exhalation and inhalation, wherein the energy-harvesting and energy-using members are incorporated into a mask that covers a person's nasal openings or oral openings or both nasal and oral openings, and wherein the energy-harvesting members provide at least 50% of the energy required by the energy-using members. In an example, this invention may be embodied in a device wherein the energy-harvesting and energy-using members are incorporated into a mask that covers a person's nasal openings or oral openings or both nasal and oral openings, and wherein these energy-harvesting and energy-using members are part of an energy self-sufficient system to provide respiratory assistance.

In various other examples, this invention may also be embodied in a method wherein harvesting energy from gas outflow, use of energy to increase gas inflow, or both occur in a member selected from the group consisting of: a nasal insert inserted into a person's nasal passageways; a mouth appliance inserted into person's mouth; a unit attached to the upper portion of a person's head and connected via gas tube to a mask or insert that covers or fills the person's nasal and/or oral openings; a unit attached to the person's torso that connects via gas tube to a mask or insert that covers or fills the person's nasal and/or oral openings; a unit implanted within the person's airway; and a unit unattached to the person apart from a gas tube connected to a mask or insert that covers or fills the person's nasal and/or oral openings.

In various other examples, this invention may also be embodied in a device wherein energy-harvesting members, energy-using members, or both occur in a member selected from the group consisting of: a nasal insert inserted into a person's nasal passageways; a mouth appliance that is inserted into person's mouth; a unit attached to the upper portion of a person's head and connected via gas tube to a mask or insert that covers or fills the person's nasal and/or oral openings; a unit attached to the person's torso that connects via gas tube to a mask or insert that covers or fills the person's nasal and/or oral openings; a unit implanted within the person's airway; and a unit unattached to the person apart from a gas tube connected to a mask or insert that covers or fills the person's nasal and/or oral openings.

FIGS. 4-5 show an example of this invention in which the sequence of energy transduction involved in energy harvesting and energy use is as follows. Kinetic energy in gas outflow is transduced into rotational kinetic energy, rotational kinetic energy is transduced into electrical energy, electrical energy is transduced into rotational kinetic energy, and then rotational kinetic energy is transduced into kinetic energy in gas inflow.

FIGS. 6-19 show various examples that provide greater detail concerning how the energy-harvesting, energy-storing, and energy-using members and functions of this invention may be embodied and configured. These examples show different configurations of the energy-harvesting and gas inflow accelerating functions that comprise the core of a method, device, and system of providing respiratory support. These various examples form the core elements of this invention. These core elements can be integrated into a mask, such as the mask shown in FIGS. 4-5. These various examples may also be incorporated into nasal inserts, a mouth appliance, or even a bedside unit. The precise manner in which such configurations may be incorporated into a gas channeling interface (such as a mask, nasal inserts, or mouth appliance) is not central to this invention. There are many different types of masks, nasal inserts, mouth appliances, or bedside units into which such energy-harvesting configurations can be incorporated.

FIG. 6 shows one example of how these core functions and members may be configured within a housing, wherein this housing can be integrated into a mask, nasal inserts, mouth appliance, or bedside unit. FIG. 6 shows a lateral cross-sectional view of a housing (601) that contains energy-harvesting, energy-storing, and energy-using members. These members roughly correspond to the gas flow channel, impeller, generator/actuator, battery, and control mechanism members that were discussed in the context of the mask in FIGS. 4-5. In various examples, housing 601 may be made from one or more materials selected from the group consisting of: ethylene propylene diene monomer (EPDM), latex, nylon, polycarbonate plastic, polyethylene, polypropylene, polystyrene, polyurethane, polyvinyl chloride, silicone, and vulcanized rubber.

In an example, housing 601 can be incorporated into a mask that covers a person's nose and mouth to provide respiratory assistance while they sleep. In an example, the left side of housing 601 would face toward the interior of the person's airway (towards the person's lungs) and be in fluid communication with the inside of a mask covering the person's nose and mouth. The right side of housing 601 would face away from the person's airway and be in fluid communication with environmental air. In another example, the right side of housing 601 could face away from the person's airway and be in fluid communication with a source of oxygen-enriched air.

In another example, housing 601 can be integrated into one or more nasal inserts. In that case, the left side of housing 601 would be in fluid communication with the person's nasal passages. The right side of housing 601 would be in fluid communication with environmental air. In this case, the configuration of elements within housing 601 could be altered so that the gas flow channel extends into the nasal passages and the other components are in a portion of the housing that is outside the nose. In another example, housing 601 may be integrated into a mouth appliance. In that case, the left side of housing 601 would be in fluid communication with the inside of the person's mouth and the right side of housing 601 would be in fluid communication with environmental air. Embodiment of this invention in self-contained, self-powered nasal inserts or in a mouth appliance would likely require miniaturization of the energy-harvesting and gas inflow accelerating components.

In another example, housing 601 may be incorporated into a unit that attaches elsewhere to a person's head or body. In another example, although less preferred, housing 601 may be incorporated into a bedside blower unit that is attached to a mask via an air tube. A bedside unit embodiment of this invention would require less miniaturization of energy-harvesting and gas inflow accelerating components. If entirely self-powered, it would also still have the advantage of offering positive airway therapy in areas of the world where people do not have access to dependable external power. However, a bedside unit embodiment is less preferred because it does not free a sleeping person from being tethered to a bedside unit by an air tube.

FIG. 6 shows one example of how the energy-transducing members of this invention may be configured. This example includes a generally-tubular gas flow channel (602) with right and left tubular sections and a central (partial disk shape) bulging section. The gas flow channel (602) extends longitudinally, left-to-right, through the upper portion of the housing (601). The central (partial disk shape) section of the gas flow channel (602) closely conforms to the outer perimeter of a paddle-wheel-style impeller (603) in its center.

In this example, the paddle-wheel-style impeller (603) has eight relatively-straight arms. These eight arms extend outwards in a radially-symmetric manner from a central axle (604) around which the impeller rotates. In other examples, impeller arms may be curved. In other examples, impeller arms may be radially-asymmetric. In other examples, there may a lesser or greater number of impeller arms. In other examples, there may be between 2 and 20 impeller arms. In other examples, the impeller may have a spiral shape, a fan blade shape, or some other shape other than that of a paddle wheel. In other examples, there may be two or more impellers in parallel sharing a single axle.

In the example shown in FIG. 6 the axle (604) of impeller (603) is perpendicular to the longitudinal axis of the gas flow channel (602). In other examples, the gas flow channel may be curved and the impeller axle may be substantively parallel to the axis of the gas flow channel in which it is located. In this example, the tubular portions of the gas flow channel on either side of the central partial-disk mid-section are linearly aligned. In another example, these tubular portions may not be linearly aligned. In an example, the left-side tubular portion of the gas flow channel may connect with the top of the central partial-disk section and the right-side tubular portion of the gas flow channel may connect with the bottom of the central disk section. In this example, both tubular end portions of the gas flow channel are parallel to each other. In another example, the tubular end portions may be perpendicular to each other, with one tube connecting to the central partial-disk section in a parallel manner and the other tube connecting to the center of the partial-disk section in a perpendicular manner.

FIG. 6 shows a generator/actuator (605) that is connected to impeller 603 by means of axle 604. From the lateral cross-sectional perspective shown in FIG. 6, the generator/actuator (605) is parallel to, and behind, the impeller (603). In this example, generator/actuator (605) is directly connected to the impeller (603) by the axle (604) of the impeller. Rotation of the impeller axle (604) directly rotates a central shaft of generator/actuator (605) in real time and thus generates electricity. In other examples, there may be an intermediate energy-transducing and/or energy-storing member between the impeller axle and the generator/actuator. In the later case, energy from rotation of the impeller can be accumulated and stored before being released to the generator/actuator to generate electricity. In an example of such an intermediate member, a winding spring with a clockwork mechanism may be an intermediate energy transducing, storing, and releasing member between the impeller and generator/actuator.

In FIG. 6, the left side of housing 601 is oriented toward the interior of a person's airway (toward their lungs). When housing 601 is integrated into a mask, the left side of the housing is in fluid communication with the mask interior. In this case, the right side of housing 601 is oriented away from the interior of the person's airway (away from their lungs) and is in fluid communication with environmental air. In another example, the right side may be in fluid communication with a source of oxygen-enriched air. This left and right orientation corresponds to the orientation of energy-harvesting components shown in the mask in FIGS. 4-5. In an example, housing 601 may be understood as being integrated into this mask. In this case, FIGS. 6-7 may be understood as showing greater detail of the internal components that were introduced in FIGS. 4-5. However, it should also be understood that housing 601 may also be integrated into nasal inserts, a mouth appliance, or a bedside unit. The precise means by which gas is channeled into the left side of this example (eg. mask, nasal inserts, mouth appliance, or other means) is not central to this invention.

In FIG. 6, gas outflow during exhalation is represented by dotted-line arrow 606 and dotted-line arrow 607. These dotted line arrows follow the outflow of gas from the left to right through gas flow channel (602) inside housing 601. Gas outflow during exhalation, from a person's lungs, enters gas flow channel 602 on the left side of FIG. 6 where it is represented by dotted-line arrow 606. This gas outflow (606) then hits the arms of impeller 603 in the central section which causes the impeller to spin in a clockwise manner. This gas outflow then continues through right-side portion of gas channel 602 where it is represented by dotted-line arrow 607. Gas outflow 607 then exits gas flow channel 602, coming out of the right side of housing 601.

When gas outflow 606 from exhalation hits impeller 603, it causes impeller 603 to spin in a clockwise direction. Although gas outflow 606 ultimately continues past impeller 603 and exits the housing 601, as represented by dotted-line arrow 607, a portion of gas outflow 606 rotates around impeller 603 before merging into outflow 607 exiting housing 601. This interaction is similar to the interaction between the paddle wheel of a paddle-wheel boat and the body of water in which the paddle boat travels, except that energy transduction occurs in the opposite direction (for exhalation). In the case of the paddle-wheel boat the rotational energy of the paddle-wheel exerts force on water, which moves the boat. In the example shown in FIG. 6 the movement of flowing gas exerts force on the impeller, which causes the impeller to rotate.

FIG. 6 also shows a battery (609). Battery (609) stores electricity that is generated by the generator/actuator (605) during exhalation for later use. Electricity is conducted from the generator/actuator (605) to the battery (609) via a wire (608). The "lightning symbol" shown over wire 608 where it connects to generator/actuator (605) symbolically represents generation of electricity by the generator during exhalation. In this example, electricity is stored in a battery. In another example, electricity may be stored in an electricity-storing member that would not be conventionally called a battery. For example, electricity may be stored in an energy-storing microchip.

In various examples, there are other types and configurations of energy-transducing members which can transduce kinetic energy from gas outflow during exhalation into rotational energy that can be used to generate electricity. In other examples, there are alternative ways to harvest and store energy that do not involve electricity. In an example, energy may be stored within a wound spring. In an example, energy may be stored in an inflatable member. In an example, energy may be stored in a fixed-size compression chamber. In other examples, energy may be stored in a chemical or biological fuel cell.

FIG. 6 also shows a control mechanism (610). Control mechanism (610) is connected to generator/actuator 605 by wire 611 and connected to battery 609 by wire 612. In the example shown in FIG. 6, the control mechanism (610) is powered by the battery (609). In an example, this control mechanism may be a microchip or other microscale computing device. In an example, control mechanism (610) controls the operation of the generator/actuator, impeller, and battery. Control mechanism 610 may switch the impeller from an energy-harvesting function that harvests energy from gas outflow during inhalation to an energy-using function that increases gas inflow during inhalation. In an example, the control mechanism may set the time lag between when the impeller stops spinning clockwise due to exhalation and when the impeller is driven counter-clockwise by the actuator. In an example, the control mechanism may control the duration of positive airway pressure at the end of exhalation or the beginning of inhalation. In an example, the control mechanism may reserve power until a respiratory cycle in which positive airway pressure is needed to correct a detected, or predicted, adverse respiratory event.

In various examples, this invention can comprise a method, device, and system to provide respiratory support that includes providing a control mechanism that allows someone to adjust one or more of the following: the timing, duration, efficiency, amount, degree, mechanism, or form of energy harvesting during a respiratory cycle; the timing, duration, efficiency, amount, degree, mechanism, or form of energy harvesting and accumulation over the span of multiple respiratory cycles; the timing, duration, efficiency, amount, degree, mechanism, or form of energy use to increase gas inflow; the timing, duration, efficiency, amount, degree, mechanism, or form of energy use and depletion over the span of multiple respiratory cycles; the timing, duration, efficiency, amount, degree, mechanism, or form of energy use to correct an actual adverse respiratory event; and the timing, duration, efficiency, amount, degree, mechanism, or form of energy use to prevent a predicted adverse respiratory event. In various examples, the person making these adjustments may be the person receiving respiratory support, a health care provider, and/or someone else assisting with care.

In an example, control mechanism (610) may be in wireless communication with a remote control mechanism. In an example, control mechanism (610) may receive wireless signals from one or more sensors that monitor respiratory activity. In various examples, a control mechanism may communicate wirelessly with a remote control mechanism that is operated by the person using the device, by a health care provider, or both.

In an example, a remote control mechanism that is in wireless communication with internal control mechanism (610) may have a visual interface. The person receiving respiratory support may be able to adjust parameters of respiratory support before they sleep. In an example, this remote control mechanism may have a touch-screen interface that enables to the person to adjust various parameters of energy-harvesting and gas inflow acceleration. In an example, the control mechanism may also communicate with a health care provider. In an example, a health care provider may monitor output from the control mechanism, with or without supplemental results from respiratory monitoring, and adjust parameters of energy-harvesting and gas inflow acceleration in real time. In an example, a health care provider may review data from the control mechanism retrospectively and adjust the operation of the device over time in response to observed respiratory patterns and events.

In various examples, this invention can comprise a method, device, and system to provide respiratory support that includes providing a wireless remote control mechanism that allows someone to adjust one or more of the following: the timing, duration, efficiency, amount, degree, mechanism, or form of energy harvesting during a respiratory cycle; the timing, duration, efficiency, amount, degree, mechanism, or form of energy harvesting and accumulation over the span of multiple respiratory cycles; the timing, duration, efficiency, amount, degree, mechanism, or form of energy use to increase gas inflow; the timing, duration, efficiency, amount, degree, mechanism, or form of energy use and depletion over the span of multiple respiratory cycles; the timing, duration, efficiency, amount, degree, mechanism, or form of energy use to correct an actual adverse respiratory event; and the timing, duration, efficiency, amount, degree, mechanism, or form of energy use to prevent a predicted adverse respiratory event. In various examples, the person making these adjustments may be the person receiving respiratory support, a health care provider, and/or someone else assisting with care.

FIG. 7 shows the same embodiment of this invention that was shown in FIG. 6, except that now it shows how this embodiment operates during inhalation. In FIG. 7, there is an inflow of gas during inhalation that enters gas channel 602 on the right side of housing 601. This gas inflow entering the gas channel 602 is represented by dotted-line arrow 701. In an example, gas inflow 701 may be normal air. In another example, gas inflow 701 may be oxygen-enriched air.

In FIG. 7, control mechanism 610 has switched generator/actuator 605 from its function as a generator to its function as an actuator. Rather than generating electricity for storage in battery 609, as it did during exhalation, generator/actuator 605 now receives electricity from battery 609 and, functioning as an actuator, transduces that electrical energy into counter-clockwise rotation of impeller 603. Counter-clockwise rotation of impeller 603 accelerates gas inflow 701 and increases the rate of gas inflow 702. This causes therapeutic positive airway pressure. In an example, this therapeutic positive airway pressure may be Positive End-Expiratory Pressure (PEEP). This interaction is similar to the interaction between the paddle wheel of a paddle-wheel boat and a body of water. In the case of a paddle-wheel boat the rotational energy of the paddle-wheel exerts force on water, which moves the boat. In the example shown in FIG. 7 the rotational energy of the impeller exerts force on the gas inflow, which increases the rate of inflow.

The example of this invention that is shown in FIGS. 6-7 comprises a method, device, and system of providing respiratory assistance wherein an energy-harvesting member is the same member as an energy-using member, but wherein this member is used in a different ways for energy-harvesting vs. energy-using. In this example, one or more energy-harvesting members are the same as one or more energy-using members. In this example, the same member (the impeller) rotates clockwise for energy-harvesting from gas outflow and then rotates counter-clockwise for energy-using to increase gas inflow. In this example, energy-harvesting involves clockwise rotation of an impeller which generates electricity that is stored in a battery. In this example, energy-using involves counter-clockwise rotation of the same impeller using electrical energy from the battery.

The example of this invention that is shown in FIGS. 6-7 comprises a method, device, and system of providing respiratory assistance that can provide respiratory assistance to a person with Obstructive Sleep Apnea (OSA), a person who snores, or a person with Chronic Obstructive Pulmonary Disease (COPD). With respect to Obstructive Sleep Apnea (OSA), Continuous Positive Airway Pressure (CPAP) is therapeutic in helping to keep a person's airway open during sleep. Although it is possible that a highly-efficient embodiment of this invention could provide CPAP someday, this invention is not likely to provide enough energy for CPAP from harvesting energy from outflow during exhalation in the near future. However, it is likely to be able to provide sufficient energy for Positive End-Expiratory Pressure (PEEP). PEEP can be therapeutic for treating OSA, but requires much less energy than CPAP.

This present invention may be able to provide Positive End-Expiratory Pressure (PEEP) with a high percentage, or even all, of the energy required for PEEP being harvested from gas outflow during exhalation. A goal of this invention is to create a self-contained energy-self-sufficient method, device, and system for treating OSA. In an example, this method, device, and system can provide PEEP during critical respiratory cycles or, with a highly-efficient energy-harvesting system, during all respiratory cycles. In an example, this invention can comprise a method, device, and system for providing respiratory assistance wherein the energy harvested from gas outflow during exhalation reduces by over 50% the need for energy from an external power source in order to increase gas inflow, as needed, during inhalation or during the period between exhalation and inhalation, during a plurality of respiratory cycles.

FIGS. 6-7 show an example of this invention embodied in a method, device, and system for providing respiratory assistance wherein energy is stored as electrical energy in a rechargeable battery. Electricity is stored between the time that it is harvested from gas outflow during exhalation and the time that it is used to increase gas inflow during inhalation or during the period between exhalation and inhalation.

In various examples, this invention may be embodied in a method, device, and system for providing respiratory assistance wherein energy is stored, between the time that it is harvested from gas outflow during exhalation and the time that it is used to increase gas inflow during inhalation; wherein energy is stored in a form selected from the group consisting of electrical energy, kinetic energy, tensile energy, pneumatic energy, thermal energy, chemical energy, biological energy, and light energy; and wherein energy is stored in a member selected from the group consisting of rechargeable battery, energy-storing microchip, rotating flywheel, coiled spring, elastic and/or stretchable member, balloon or other inflatable member, pressurized compartment, chemical solution, and plurality of microorganisms.

FIGS. 8-9 show another example of how this invention may be embodied. This example is similar to the one shown in FIGS. 6-7, except that this example has two gas flow channels (one for exhalation and one for inhalation) and separate generator vs. actuator members that are attached to two separate impellers. In particular, FIG. 8 shows a housing (801) that contains two gas flow channels (802 and 811). Gas flow channel 802 contains impeller 803 which is connected to generator 805 by axle 804. Gas outflow during exhalation 606 hits the arms of impeller 803 which causes impeller 803 to spin clockwise which generates electricity in generator 805. This electricity then flows through wire 806 to battery 807 where it is stored until used to increase gas inflow during inhalation, or during the period between exhalation and inhalation.

FIG. 9 shows how this same embodiment works during inhalation. During inhalation, electricity from battery 807 flows to actuator 814 which causes impeller 812 to spin clockwise which increases the flow of gas inflow between gas inflow 701 to gas inflow 702. This provides therapeutic positive airway pressure during inhalation, or during the period between exhalation and inhalation. FIGS. 8-9 also show a control mechanism (808) that controls the operation of generator 805 and actuator 814. In an example, internal control unit 808 may be in wireless communication with a remote control mechanism that is operated by the person receiving respiratory support and/or by a health care professional.

One potential advantage of the example shown in FIGS. 8-9 over the example shown in FIGS. 6-7 is that in FIGS. 8-9 the impeller does not have to change rotational direction (clockwise vs. counter-clockwise) when the respiratory cycle changes from exhalation to inhalation. Since changing rotational direction can require additional energy to overcome rotational momentum, the example shown in FIGS. 8-9 can be more energy efficient. Further, if there is enough momentum in rotation of one or both impellers, then momentum may even be harnessed to help increase gas inflow during inhalation. Another potential advantage of the example shown in FIGS. 8-9 is that having a separate generator vs. actuator may allow more precise control over the energy-harvesting and gas inflow acceleration functions than is possible with a single combined generator/actuator.

The example of this invention that is shown in FIGS. 8-9 comprises a method, device, and system of providing respiratory assistance wherein an energy-harvesting member is a different member than an energy-using member. Expressing this functionality in different wording, the example shown in FIGS. 8-9 comprises a method, device, and system of providing respiratory assistance wherein an energy-transducing member for collecting and storing energy from gas outflow is different than an energy-transducing member for using stored energy to increase gas inflow. An energy-transducing member is a member that converts energy from one form to another. For example, an energy-transducing member may convert the kinetic energy of a moving gas flow into the kinetic energy of a rotating impeller. In another example, an energy-transducing member may convert the kinetic energy of a rotating impeller into electrical energy via an electrical generator.

FIGS. 10-11 show another example of how this invention may be embodied. Like the example shown in FIGS. 6-7, this example comprises a method, device, and system of providing respiratory assistance wherein the energy-harvesting member is the same as the energy-using member. However, unlike the example in FIGS. 6-7, in the example in FIGS. 10-11 this member rotates clockwise for energy-harvesting from gas outflow and also rotates clockwise for energy-using to increase gas inflow. This avoids having to reverse the direction of rotation between exhalation and inhalation. This can be more efficient in terms of converting kinetic energy to electrical energy. This is accomplished through the use of a series of air valves that channel gas outflow and gas inflow in the same direction past a central impeller.

In particular, FIGS. 10-11 show an example of this invention in which two gas channels (1002 and 1011) curve together and intersect in a common channel in the middle of a housing (1001). In the middle of this common channel is an impeller (1003) that rotates around an axle (1004). This axle (1004) is connected to a generator/actuator (1005) that is, in turn, connected to a battery (1007) by a wire (1006). FIGS.

10-11 also show air valves (1014 and 1012) that open or close portions of the two gas channels. These air valves are controlled by a control mechanism (1008).

FIG. 10 shows this example during exhalation wherein gas outflow 606 enters the left portion of upper tubular gas channel 1002, hits and spins impeller 1003 clockwise, and then exits housing 1001 through the right portion of lower tubular gas channel 1011 as gas outflow 607. The gas flow takes this circuitous route during exhalation because the right portion of upper tubular gas channel 1002 is closed by air valve 1014 and the left portion of lower tubular gas channel 1011 is closed by air valve 1012. The opening and closing of these air valves is controlled by control mechanism 1008 that is connected to battery 1007 by wire 1010. This is one example of the energy-harvesting function of this invention.

FIG. 11 shows this same example during inhalation. During inhalation gas inflow 701 enters the right portion of upper tubular gas channel 1002 and comes to impeller 1003. The control mechanism engages generator/actuator 1005 (as an actuator) to use energy from battery 1007 to spin impeller 1003 clockwise. The clockwise spinning of impeller 1003 accelerates gas inflow 701, increases the rate of gas inflow 702, and provides therapeutic positive airway pressure. The gas flow takes this circuitous route during inhalation because the left portion of upper tubular gas channel 1002 is closed by air valve 1012 and the right portion of lower tubular gas channel 1011 is closed by air valve 1014. This is one example of the gas inflow acceleration function of this invention.

As noted above, in this example the opening and closing of air valves is controlled by control mechanism 1008. In an example, control mechanism 1008 can be informed of the different phases of the respiratory cycle by the results of sensor monitoring, such as sensor monitoring of respiratory sounds. In an example, these results may be wirelessly communicated to control mechanism 1008. In another example, control mechanism 1008 may be informed of different phases of the respiratory cycle by changes in the rotational speed of impeller 1003. For example, when impeller 1003 slows down and stops, then this may signal the end of the exhalation phase of respiration.

The embodiment of this invention that is shown in FIGS. 10-11 changes impeller momentum from a problem into an asset. Since the impeller turns in the same clockwise direction during both exhalation and inhalation, any residual momentum that the impeller has at the end of the exhalation cycle helps to increase the rate of gas inflow at the start of inhalation. The example of this invention that will be shown in FIGS. 12-13 takes even greater advantage of impeller momentum to make this method, device, and system even more energy efficient.

The example shown in FIGS. 12-13 is like the example shown in FIGS. 10-11 except that the impeller is now heavier and has greater rotational momentum. In this example, the impeller acts like a flywheel. Such an impeller more completely transduces the kinetic energy of gas outflow into rotational momentum. The example shown in FIGS. 12-13 relies solely on the rotational momentum of the heavier impeller to provide a pulse of positive air pressure at the start of inhalation. Electrical power (from a battery) may be needed to power the control mechanism and air valves, but this example does not use electrical power for an actuator to increase gas inflow as was done in previous examples. For this reason, this example of the invention will probably not provide positive airway pressure throughout all of inhalation. However, this example is likely to generate a pulse of air immediately after exhalation that can provide therapeutic Positive End-Expiratory Pressure (PEEP). Advantages of this example include lower complexity and likely lower manufacturing cost.

FIGS. 4-13 show various examples of how this invention may be embodied in a device for providing respiratory assistance comprising: one or more energy-harvesting members that generate electrical energy from gas outflow during exhalation; and one or more energy-using members that use the harvested electrical energy to increase gas inflow during inhalation or during the period between exhalation and inhalation. In an example, this invention may be embodied in a method of providing respiratory assistance while a person sleeps comprising: transducing energy from gas outflow during exhalation; accumulating this energy over the span of several respiratory cycles; and using energy after it has been accumulated over the span of several respiratory cycles in order to increase gas inflow to correct or avoid airway closure in a particular respiratory cycle.

FIGS. 14-15 shown an example of this invention in which energy is harvested from gas outflow during exhalation and stored in the form of rotational kinetic energy. This example differs from examples in prior figures in that it does not have any electrical components. Gas flow is directed by a series of one-way air valves and gas inflow is accelerated by the momentum of a impeller. The kinetic energy of gas outflow during exhalation causes the impeller to spin. The spinning impeller then increases gas inflow during inhalation. FIGS. 14-15 show an example of this invention in which the sequence of energy transduction involved in energy harvesting and energy use is as follows—kinetic energy of gas outflow is transduced into rotational kinetic energy and then rotational kinetic energy is transduced into kinetic energy in gas inflow.

Specifically, FIG. 14 shows a housing (1001) which may be incorporated into a mask, nasal insert, or mouth appliance. In other examples, housing 1001 may be incorporated into a bedside blower unit. In FIG. 14, there are two gas flow channels, 1002 and 1011, that travel longitudinally through housing 1001. There are four one-way gas flow valves (1401, 1402, 1403, and 1404) in these two gas flow channels. These one-way valves serve to direct gas outflow during exhalation and gas inflow during inhalation in the same direction across central impeller 1201. Central impeller 1201, with eight radially-extending arms, rotates around axle 1202.

FIG. 14 shows this example of the invention during exhalation. During exhalation, exhaled gas outflow 606 enters the left side of gas flow channel 1002 and passes through one-way air valve 1401. This gas outflow then hits and spins central impeller 1201 clockwise. This gas outflow then passes through one-way air valve 1404 and exits the right side of gas flow channel 1011 as gas outflow 607. Due to momentum, central impeller continues to spin after exhalation ends. In an example, impeller 1201 may act as a flywheel.

FIG. 15 shows this same embodiment of the invention during inhalation. During inhalation, gas inflow 701, which may come from environmental air or from a source of oxygen-enriched air, enters the right side of gas flow channel 1002 and passes through one-way air valve 1403. This gas inflow is then accelerated by the clockwise spinning of central impeller 1201. This spinning is due to momentum from the spinning that was caused by gas outflow during exhalation. This gas inflow then passes through one-way air valve 1402 and exits the left side of gas flow channel 1011 as gas inflow 702. In various examples, gas inflow 702 then enters a person's airway via a mask, nasal insert, or mouth appliance.

In this example, impeller 1201 acts as a simple flywheel itself. In other examples, impeller 1201 may be attached, via axle 1202, to a series of gears which gear up, or gear down, the rotational energy into a separate flywheel. In various examples, different gear ratios may help to better store the kinetic energy of gas outflow in the rotation of a flywheel in order to better accelerate gas inflow.

FIGS. 16-17 show an example of this invention in which energy from gas outflow is stored in the form of tensile mechanical energy in a spiral spring. FIGS. 16-17 show an example of this invention in which the sequence of energy transduction involved in energy harvesting and energy use is as follows—kinetic energy of gas outflow is transduced into rotational kinetic energy, rotational kinetic energy is transduced into tensile energy, tensile energy is transduced into rotational kinetic energy, and then rotational kinetic energy is transduced into kinetic energy in gas inflow.

FIG. 16 shows this example during exhalation. FIG. 16 shows a gas flow channel 1602 that travels longitudinally through housing 1601. Housing 1601 may be incorporated into a mask, nasal insert, or mouth appliance. In FIG. 16, gas outflow 606 during exhalation enters gas flow channel 1602 on the left side. Gas outflow 606 then hits and spins impeller 1603 clockwise around axle 1604. Axle 1604, in turn, is engaged, via gear teeth, with gear 1605. The rotation of impeller 1603 rotates axle 1604 which rotates gear 1605 which winds spiral spring 1606. The inner end of spiral spring 1606 is attached to gear 1605 and the outer end of spiral spring 1606 is attached to fastener 1607.

As impeller 1603 rotates during exhalation, spiral spring 1606 is wound tighter and resistance to exhalation via impeller 1603 increases. This resistance, in itself, could be sufficient to create PEEP. However, in order to not only resist exhalation, but also increase inhalation, this example uses the unwinding action of spring 1606 to accelerate inhalation—at least the start thereof. In an example, this device provides an initial acceleration of gas inflow at the start of inhalation.

FIG. 17 shows this example of the invention during inhalation, or during the period between exhalation and inhalation. In FIG. 17, gas inflow 701 enters the right side of air flow channel 1602. Gas inflow 701 may come from environmental air or from a source of oxygen-enriched air. Gas inflow 701 is accelerated by impeller 1603 spinning in a counter-clockwise direction. This counter-clockwise spinning is powered by the unwinding action of spiral spring 1606 after it has been wound up during exhalation. In an example, accelerated gas flow then exits the left side of air flow channel 1602 and enters the person's airway via a mask, nasal insert, or mouth appliance.

FIGS. 18-19 show an example of this invention in which the sequence of energy transduction involved in energy harvesting and energy use is as follows. Kinetic energy of gas outflow is transduced into pneumatic and tensile energy. Then pneumatic and tensile energy is transduced into kinetic energy in gas inflow.

FIGS. 18-19 show a housing (1801) that contains two expandable gas-containing chambers (1802 and 1807) that are linked by a sliding member (1813) in housing 1801 so that they expand or contract in tandem. Springs (1814 and 1815) within housing 1801 resist expansion of the expandable gas-containing chambers (1802 and 1807).

The two gas-containing chambers each have gas flow tubes in fluid communication with their interiors. Gas-containing chamber 1802 receives gas flow via tube 1805 that is in fluid communication with a person's airway when gas valve 1806 is open. Gas-containing chamber 1802 expels gas flow via tube 1803 that is in fluid communication with the environment when gas valve 1804 is open. Gas-containing chamber 1807 receives gas flow via tube 1810 that is in fluid communication with the environment when gas valve 1811 is open. Gas-containing chamber 1807 expels gas flow via tube 1808 that is in fluid communication with a person's airway when gas valve 1809 is open. In an example, gas valves 1804, 1806, 1809, and 1811 may be opened or closed by a control unit.

FIG. 18 shows this example of the invention during exhalation. During exhalation, gas valves 1804 and 1809 are closed, while gas valves 1806 and 1811 are open. In an example, gas valve opening and closing are determined by a control unit. In FIG. 18, exhaled gas flow 1812 enters and expands chamber 1802. Since chamber 1802 is linked in tandem to chamber 1807 by sliding member 1813, chamber 1807 also expands. However, while chamber 1802 is filled with stale air from exhalation, chamber 1807 is filled with fresh air from the environment. Expansion of the two chambers compresses springs 1814 and 1815, which store some of the energy from gas outflow during exhalation in the form of tensile mechanical energy.

FIG. 19 shows this example of the invention during inhalation. During inhalation, gas valves 1806 and 1811 are closed, while gas valves 1804 and 1809 are open. In an example, gas valve opening and closing are determined by a control unit. In FIG. 19, springs 1814 and 1815 are no longer compressed by the pressure of exhalation. Accordingly, springs 1814 and 1815 push back on, and compress, the two air chambers (1802 and 1807). Stale exhaled air from chamber 1802 is released into the environment. Fresh air from chamber 1807 is released into the person's airway.

The condition of having too much carbon dioxide in the blood is called hypercapnia. Hypercapnia can cause: confusion; dyspnoea; extrasystoles; flushed skin; headache; increased blood pressure; muscle twitches; reduced neural activity; tachypnea; and other, more severe, outcomes. Hypercapnia can be caused by too much recycling of stale exhaled gas outflow into gas inflow. For example, rebreathing the same air (for example, in and out of a closed bag) can cause hypercapnia. Also, offering too much resistance to gas outflow during exhalation, without accelerating gas inflow during inhalation, may cause mild hypercapnia. Methods and devices that resist gas outflow during exhalation but do not accelerate gas inflow during inhalation may cause mild hypercapnia. The energy-harvesting function of this invention can involve resisting gas outflow during exhalation. However, this invention avoids causing hypercapnia because it uses the energy harvested from gas outflow during exhalation to increase gas inflow during inhalation. This invention also does not substantively recycle exhaled air into inhaled air.

FIGS. 4-19 show examples of a method, device, and system for providing respiratory assistance in which energy is harvested from gas outflow during exhalation and used to increase gas inflow during inhalation, while providing fresh air during inhalation. In an example, the percentage of gas inhaled during inhalation that is comprised of gas that was exhaled during exhalation may be called the "rebreathing percentage." In various examples, this method, device, and system for providing respiratory assistance may be comprised so that the "rebreathing percentage" is below a target percentage. In various examples, this target percentage may be between 5% and 50%.

In an example, a method, device, and system for providing respiratory assistance that involves harvesting energy from gas outflow during exhalation may be comprised to provide sufficient fresh air during inhalation to avoid hypercapnia. In an example, a method, device, and system for providing respiratory assistance that involves harvesting energy from gas outflow during exhalation may be comprised to provide sufficient fresh air during inhalation to avoid a high blood gas carbon dioxide level. In an example, this invention can comprise a method, device, and system for providing respiratory assistance that involves harvesting energy from gas outflow during exhalation that provides sufficient fresh air during inhalation to avoid causing a person's blood gas carbon dioxide to increase above a target maximum level. In various examples, this target maximum can be between 30 mmHg and 60 mmHg.

FIGS. 4-19 show examples of a method and device for providing respiratory assistance in which energy is harvested from gas outflow during exhalation and used to increase gas inflow during inhalation, without substantively recirculating gas outflow from exhalation back into the person in gas inflow during inhalation.

In an example, this invention can comprise a method and device of providing respiratory assistance that, in addition to including energy-harvesting and energy-using members, also includes a control mechanism. In an example, this control mechanism can selectively control the manner in which energy is harvested from gas outflow during exhalation and used to increase gas inflow during inhalation.

In an example, this control mechanism can selectively control the manner in which energy from gas outflow during exhalation is transduced and stored for subsequent use during inhalation.

In an example, this invention can include a remote control mechanism that communicates with components of a device by wireless means. In an example, this invention can comprise a method and device wherein this method and device includes a control mechanism that selectively controls the timing and/or amount of energy harvesting during exhalation and energy use during inhalation and wherein this control mechanism can be remotely adjusted by wireless communication. In an example, this remote control mechanism may include a graphic user interface which enables the person benefiting from the device to monitor and adjust parameters of energy-harvesting and energy use. In an example, this remote control mechanism may include a graphic user interface which enables a care provider, other than the person benefiting from the device, to remotely monitor and adjust parameters of energy-harvesting and energy use.

In an example, this invention may include a control mechanism that selectively controls the timing and amount of energy harvesting from gas outflow during exhalation and/or the timing and amount of energy used to increase gas inflow during inhalation. In an example, energy harvested from gas outflow during exhalation may be used to temporarily increase the pressure, or the flow rate, of gas within the airway immediately prior to inhalation. In an example, energy harvested from gas outflow during exhalation may be used to increase the pressure, or flow rate, of gas inflow throughout the entire inhalation phase of the respiratory cycle.

In an example, energy may be harvested and accumulated from gas outflow during multiple respiratory cycles in order to accumulate enough energy to provide a therapeutic level of increase in gas inflow during one specific respiratory cycle, or during a particular type of respiratory event, when acute clinical need is indicated by clinical monitoring. In various examples, such clinical monitoring may include: monitoring respiratory sounds, monitoring respiratory gas flow rates, monitoring blood oxygen level, monitoring EEG signals, or monitoring EKG signals.

In an example, kinetic energy may be harvested from gas outflow over the span of a certain number "X" of normal respiratory cycles before sufficient energy is accumulated in an energy storage device to provide a therapeutic level of increase in gas inflow during inhalation. In various examples, this number "X" of normal respiratory cycles may be between 5 and 500. In various examples, this number may vary based on the actual power generated in successive respiratory cycles.

In an example, this invention may be embodied in a method and device in which energy is accumulated during the gas outflow of exhalation during multiple respiratory cycles before this energy is used to increase gas inflow to open the airway at a time when the results of respiratory, sound, blood, or other monitoring indicate that airway closure has occurred or is likely to occur. In an example, gas inflow during inhalation may be increased when the results of clinical monitoring indicate that airway constriction has occurred. In another example, gas inflow during inhalation may be increased in a prophylactic manner when analysis of clinical monitoring suggests that airway constriction is likely to occur.

In various examples, this invention may be embodied in a method and device and system for providing respiratory assistance wherein the sequence of energy transduction involved in energy harvesting and energy use is selected from the following group of four sequences: (a) kinetic energy of gas outflow is transduced into rotational kinetic energy, rotational kinetic energy is transduced into electrical energy, electrical energy is transduced into rotational kinetic energy, and then rotational kinetic energy is transduced into kinetic energy in gas inflow; (b) kinetic energy of gas outflow is transduced into rotational kinetic energy, rotational kinetic energy is transduced into tensile energy, tensile energy is transduced into rotational kinetic energy, and then rotational kinetic energy is transduced into kinetic energy in gas inflow; (c) kinetic energy of gas outflow is transduced into rotational kinetic energy and then rotational kinetic energy is transduced into kinetic energy in gas inflow; and (d) kinetic energy of gas outflow is transduced into pneumatic energy and then pneumatic energy is transduced into kinetic energy in gas inflow.

I claim:

1. A device for providing respiratory assistance comprising:
   one or more sensors that monitor respiratory activity;
   a microchip or microscale computer which receives signals from the one or more sensors;
   an energy-harvesting impeller or turbine which is rotated by gas outflow during exhalation;
   a generator which is driven by rotation of the energy-harvesting impeller or turbine, wherein electricity generated by the generator is accumulated and stored over the span of X normal respiratory cycles, and wherein X is greater than 5;
   an energy-using impeller or turbine which increases gas inflow during inhalation; and
   an actuator which drives the rotation of the energy-using impeller or turbine, wherein this actuator is controlled by the microchip or other microscale computer so as to use the electricity which was accumulated and stored over the span of X normal respiratory cycles to drive the rotation of the energy-using impeller or turbine during a specific respiratory cycle when signals from the one or more sensors indicate that gas inflow is needed to correct, or avoid, an acute episode of a respiratory condition, and wherein the generator and the actuator are separate energy-transducing members.

2. A device for providing respiratory assistance comprising:
   one or more sensors that monitor respiratory activity;
   a microchip or microscale computer which receives signals from the one or more sensors;

an energy-harvesting impeller or turbine which is rotated by gas outflow during exhalation;

a generator which is driven by rotation of the energy-harvesting impeller or turbine, wherein electricity generated by the generator is accumulated and stored over the span of X normal respiratory cycles, and wherein X is greater than 5;

an energy-using impeller or turbine which increases gas inflow during inhalation; and an actuator which drives the rotation of the energy-using impeller or turbine, wherein this actuator is controlled by the microchip or other microscale computer so as to use the electricity which was accumulated and stored over the span of X normal respiratory cycles to drive the rotation of the energy-using impeller or turbine during a specific respiratory cycle when signals from the one or more sensors indicate that gas inflow is needed to correct, or avoid, an acute episode of a respiratory condition, and wherein there are two gas flow channels, a first channel for exhalation and a second channel for inhalation, and wherein the energy-harvesting impeller or turbine is in the first channel and the energy-using impeller or turbine is in the second channel.

3. The device in claim 2 wherein this device further comprises a wireless remote control mechanism.

* * * * *